US007893197B2

(12) United States Patent
Bonaventure et al.

(10) Patent No.: US 7,893,197 B2
(45) Date of Patent: Feb. 22, 2011

(54) RELAXIN-3 CHIMERIC POLYPEPTIDES AND THEIR PREPARATION AND USE

(75) Inventors: Pascal Bonaventure, San Diego, CA (US); Chester Kuei, San Diego, CA (US); Changlu Liu, San Diego, CA (US); Timothy W. Lovenberg, San Diego, CA (US); Steven W. Sutton, Carlsbad, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 329 days.

(21) Appl. No.: 11/660,883

(22) PCT Filed: Aug. 25, 2005

(86) PCT No.: PCT/US2005/030257

§ 371 (c)(1), (2), (4) Date: Feb. 23, 2007

(87) PCT Pub. No.: WO2006/026355

PCT Pub. Date: Mar. 9, 2006

(65) Prior Publication Data
US 2008/0051336 A1 Feb. 28, 2008

(51) Int. Cl.
*A61K 38/00* (2006.01)
*C07K 14/64* (2006.01)
(52) U.S. Cl. .................. 530/300; 530/325; 530/350
(58) Field of Classification Search ............... None
See application file for complete search history.

(56) References Cited

U.S. PATENT DOCUMENTS

| 4,366,241 | A | 12/1982 | Tom et al. |
|---|---|---|---|
| 4,376,110 | A | 3/1983 | David et al. |
| 4,517,288 | A | 5/1985 | Giegel et al. |
| 4,837,168 | A | 6/1989 | de Jaeger et al. |
| 4,873,316 | A | 10/1989 | Meade et al. |
| 5,223,409 | A | 6/1993 | Ladner et al. |
| 5,272,071 | A | 12/1993 | Chappel |
| 5,571,698 | A | 11/1996 | Ladner et al. |
| 5,955,309 | A | 9/1999 | Ellis et al. |
| 2003/0113798 | A1 | 6/2003 | Burmer et al. |
| 2005/0059089 | A1 | 3/2005 | Kuei et al. |
| 2005/0074814 | A1 | 4/2005 | Chen et al. |
| 2007/0004619 | A1* | 1/2007 | Del Borgo et al. ............ 514/9 |

FOREIGN PATENT DOCUMENTS

| EP | 0264166 | 8/1996 |
|---|---|---|
| WO | WO 91/06667 | 5/1991 |
| WO | WO 00/23111 | 4/2000 |
| WO | WO 01/36471 | 5/2001 |
| WO | WO 01/62797 | 8/2001 |
| WO | WO 01/68862 | 9/2001 |
| WO | WO 01/74904 | 10/2001 |
| WO | WO 01/75164 | 10/2001 |
| WO | WO 01/85791 | 11/2001 |
| WO | WO 02/00719 | 1/2002 |
| WO | WO 2004/082598 | 9/2004 |
| WO | WO 2005/014616 | 2/2005 |

OTHER PUBLICATIONS

Bathgate et al., JBC, 2002; 277: 1148-1157.*
Liu and Lovenberg, Results Probl Cell Differ. 2008; 46: 213-237.*
Adams et al., "Tactile stimulation activates dopamine release in the lateral septum", *Brain Research*, 2000, vol. 858, pp. 177-180.
Adham et al., "Cloning of a cDNA for a novel insulin-like peptide of the testicular Leydig cells", *J Biol Chem.*, 1993, vol. 268(35), pp. 26668-26672.
Akerstrom et al., "Protein G: a powerful tool for binding and detection of monoclonal and polyclonal antibodies", *J Immunol.*, 1985, vol. 135(4), pp. 2589-2592.
Altschul et al., "Basic local alignment search tool", *J Mol Biol.*, 1990, vol. 215, pp. 403-410.
Altschul et al., "Gapped BLAST and PSI-BLAST: a new generation of protein database search programs", *Nucleic Acids Res.*, 1997, vol. 25(17), pp. 3389-3402.
Amann et al., "Tightly regulated tac promoter vectors useful for the expression of unfused and fused proteins in *Escherichia coli*", *Gene*, 1988, vol. 69, pp. 301-315.
Baccari et al., "Relaxin: new functions for an old peptide", *Curr Protein Pept Sci.*, 2004, vol. 5, pp. 9-18.
Baldari et al., "A novel leader peptide which allows efficient secretion of a fragment of human interleukin 1 beta in *Saccharomyces cerevisiae*", *EMBO J.*, 1987, vol. 6(1), pp. 229-234.
Banerji et al., "A lymphocyte-specific cellular enhancer is located downstream of the joining region in immunoglobulin heavy chain genes", *Cell*, 1983, vol. 33, pp. 729-740.
Bani, "Relaxin: a pleiotropic hormone", *Gen Pharmacol.*, 1997, vol. 28(1), pp. 13-22.
Bathgate et al., "Human relaxin gene 3 (H3) and the equivalent mouse relaxin (M3) gene. Novel members of the relaxin peptide family", *J Biol Chem.*, 2002, vol. 277(2), pp. 1148-1157.
Bell et al., "Sequence of the human insulin gene", *Nature*, 1980, vol. 284, pp. 26-32.
Bell et al., "Sequence of a cDNA clone encoding human preproinsulin-like growth factor II", *Nature*, 1984, vol. 310, pp. 775-777.
Benjannet et al., "PC1 and PC2 are proprotein convertases capable of cleaving proopiomelanocortin at distinct pairs of basic residues", *Proc Natl Acad Sci USA.*, 1991, vol. 88, pp. 3564-3568.
Boels et al., "Identification and characterisation of GPR100 as a novel human G-protein-coupled bradykinin receptor", *Br J Pharmacol.*, 2003, vol. 140, pp. 932-938.
Bogatcheva et al., "GREAT/LGR8 is the only receptor for insulin-like 3 peptide", *Mol Endocrinol.*, 2003, vol. 17(12), pp. 2639-2646.
Brummelkamp et al., "A system for stable expression of short interfering RNAs in mammalian cells", *Science*, 2002, vol. 296, pp. 550-553.

(Continued)

*Primary Examiner* — Bridget E Bunner
*Assistant Examiner* — Christina Borgeest

(57) ABSTRACT

Chimeric polypeptides of relaxin-3, prepropolypeptides thereof, polynucleotides encoding such polypeptides, and associated expression vectors and host cells are described. The polypeptides may be used to prepare receptor-ligand complexes with GPCR135 or GPCR142, which may be used in assay methods.

2 Claims, 12 Drawing Sheets

OTHER PUBLICATIONS

Bullesbach et al., "The receptor-binding site of human relaxin II. A dual prong-binding mechanism", *J Biol Chem.*, 1992, vol. 267(32), pp. 22957-22960.

Bullesbach et al., "Tryptophan B27 in the relaxin-like factor (RLF) is crucial for RLF receptor-binding", *Biochemistry*, 1999, vol. 38, pp. 3073-3078.

Bullesbach et al., "The relaxin receptor-binding site geometry suggests a novel gripping mode of interaction", *J Biol Chem.*, 2000, vol. 275(45), pp. 35276-35280.

Burazin et al., "Restricted, but abundant, expression of the novel rat gene-3 (R3) relaxin in the dorsal tegmental region of brain", *J Neurochem.*, 2002, vol. 82, pp. 1553-1557.

Byrne et al., "Multiplex gene regulation: a two-tiered approach to transgene regulation in transgenic mice", *Proc. Natl. Acad. Sci. USA*, 1989, vol. 86, pp. 5473-5477.

Calame et al., "Transcriptional controlling elements in the immunoglobulin and T cell receptor loci", *Adv Immunol.*, 1988, vol. 43, pp. 235-275.

Camper et al., "Postnatal repression of the alpha-fetoprotein gene is enhancer independent", *Genes Dev.*, 1989, vol. 3, pp. 537-546.

Carrillo et al., "The multiple sequence alignment problem in biology", *SIAM J Appl Math*, 1988, vol. 48(5), pp. 1073-1082.

Chalmers et al., "Localization of novel corticotropin-releasing factor receptor (CRF2) mRNA expression to specific subcortical nuclei in rat brain: comparison with CRF1 receptor mRNA expression", *J Neurosci.*, 1995, vol. 15(10), pp. 6340-6350.

Chen et al., "Pharmacological characterization of relaxin-3/INSL7 receptors GPCR135 and GPCR142 from different mammalian species", *J Pharmacol Exp Ther.*, 2005, vol. 312(1), pp. 83-95.

Civelli et al., "Novel neurotransmitters as natural ligands of orphan G-protein-coupled receptors", *Trends Neurosci.*, 2001, vol. 24(4), pp. 230-237.

Claasz et al., "Relaxin-like bioactivity of ovine Insulin 3 (INSL3) analogues", *Eur J Biochem.*, 2002, vol. 269, pp. 6287-6293.

Conklin et al., "Identification of INSL5, a new member of the insulin superfamily", *Genomics*, 1999, vol. 60, pp. 50-56.

Cull et al., "Screening for receptor ligands using large libraries of peptides linked to the C terminus of the lac repressor", *Proc. Natl. Acad. Sci. USA*, 1992, vol. 89, pp. 1865-1869.

Devereux et al., "A comprehensive set of sequence analysis programs for the VAX", *Nucleic Acids Res.*, 1984, vol. 12(1), pp. 387-395.

Edlund et al., "Cell-specific expression of the rat insulin gene: evidence for role of two distinct 5' flanking elements", *Science*, 1985, vol. 230, pp. 912-916.

Eigenbrot et al., "X-ray structure of human relaxin at 1.5 A. Comparison to insulin and implications for receptor binding determinants", *J Mol Biol.*, 1991, vol. 221, pp. 15-21.

Elbashir et al., "RNA interference is mediated by 21- and 22-nucleotide RNAs", *Genes Dev.*, 2001, vol. 15, pp. 188-200.

Fire et al., "Potent and specific genetic interference by double-stranded RNA in *Caenorhabditis elegans*", *Nature*, 1998, vol. 391, pp. 806-811.

Fodor et al., "Multiplexed biochemical assays with biological chips", *Nature*, 1993, vol. 364, pp. 555-556.

Goto et al., "Connections of the nucleus incertus", *J Comp Neurol.*, 2001, vol. 438, pp. 86-122.

Gudermann et al., "Evidence for dual coupling of the murine luteinizing hormone receptor to adenylyl cyclase and phosphoinositide breakdown and Ca2+ mobilization. Studies with the cloned murine luteinizing hormone receptor expressed in L cells", *J Biol Chem.*, 1992, vol. 267(7), pp. 4479-4488.

Haase et al., "Detection of viral nucleic acids by in situ hybridization", *Methods in Virology*, 1984, vol. VII, pp. 189-226.

Hammond et al., "An RNA-directed nuclease mediates post-transcriptional gene silencing in *Drosophila* cells", *Nature*, 2000, vol. 404, pp. 293-296.

Hampson et al., "Probing the ligand-binding domain of the mGluR4 subtype of metabotropic glutamate receptor", *J Biol Chem.*, 1999, vol. 274(47), pp. 33488-33495.

Hosaka et al., "Arg-X-Lys/Arg-Arg motif as a signal for precursor cleavage catalyzed by furin within the constitutive secretory pathway", *J Biol Chem.*, 1991, vol. 266(19), pp. 12127-12130.

Houghten et al., "The use of synthetic peptide combinatorial libraries for the identification of bioactive peptides", *Biotechniques*, 1992, vol. 13(3), pp. 412-421.

Howard et al., "Orphan G-protein-coupled receptors and natural ligand discovery", *Trends Pharmacol Sci.*, 2001, vol. 22(3), pp. 132-140.

Hsu et al., "The three subfamilies of leucine-rich repeat-containing G protein-coupled receptors (LGR): identification of LGR6 and LGR7 and the signaling mechanism for LGR7", *Mol Endocrinol.*, 2000, vol. 14(8), pp. 1257-1271.

Hsu et al., "Activation of orphan receptors by the hormone relaxin", *Science*, 2002, vol. 295, pp. 671-674.

Hsu, "New insights into the evolution of the relaxin-LGR signaling system", *Trends Endocrinol Metab.*, 2003, vol. 14(7), pp. 303-309.

Hsu et al., "Relaxin signaling in reproductive tissues", *Mol Cell Endocrinol.*, 2003, vol. 202, pp. 165-170.

Hudson et al., "Structure of a genomic clone encoding biologically active human relaxin", *Nature*, 1983, vol. 301, pp. 628-631.

Hudson et al., "Relaxin gene expression in human ovaries and the predicted structure of a human preprorelaxin by analysis of cDNA clones", *EMBO J.*, 1984, vol. 3(10), pp. 2333-2339.

Huse et al., "Generation of a large combinatorial library of the immunoglobulin repertoire in phage lambda", *Science*, 1989, vol. 246, pp. 1275-1281.

Ivell et al., "Reproductive biology of the relaxin-like factor (RLF/INSL3)", *Biol Reprod.*, 2002, vol. 67, pp. 699-705.

Karlin et al., "Methods for assessing the statistical significance of molecular sequence features by using general scoring schemes", *Proc Natl Acad Sci USA*, 1990, vol. 87, pp. 2264-2268.

Karlin et al., "Applications and statistics for multiple high-scoring segments in molecular sequences", *Proc Natl Acad Sci USA*, 1993, vol. 90, pp. 5873-5877.

Kaufman et al., "Translational efficiency of polycistronic mRNAs and their utilization to express heterologous genes in mammalian cells", *EMBO J.*, 1987, vol. 6(1), pp. 187-193.

King et al., "The superior colliculus", *Curr Biol.*, 2003, vol. 14(9), pp. R335-R338.

Kohler et al., "Continuous cultures of fused cells secreting antibody of predefined specificity", *Nature*, 1975, vol. 256, pp. 495-497.

Kohler et al., "Derivation of specific antibody-producing tissue culture and tumor lines by cell fusion", *Eur J Immunol.*, 1976, vol. 6, pp. 511-519.

Koman et al., "Molecular characterization and in vitro biological activity of placentin, a new member of the insulin gene family", *J Biol Chem.*, 1996, vol. 271(34), pp. 20238-20241.

Krajnc-Franken et al., "Impaired nipple development and parturition in LGR7 knockout mice", *Mol Cell Biol.*, 2004, vol. 24(2), pp. 687-696.

Kronvall, "A surface component in group A, C, and G *streptococci* with non-immune reactivity for immunoglobulin G", *J Immunol.*, 1973, vol. 111(5), pp. 1401-1406.

Kumagai et al., "INSL3/Leydig insulin-like peptide activates the LGR8 receptor important in testis descent", *J Biol Chem.*, 2002, vol. 277(35), pp. 31283-31286.

Kurjan et al., "Structure of a yeast pheromone gene (MF alpha): a putative alpha-factor precursor contains four tandem copies of mature alpha-factor", *Cell*, 1982, vol. 30, pp. 933-943.

Lam, "Application of combinatorial library methods in cancer research and drug delivery", *Anti-cancer drug des.*, 1997, vol. 12, pp. 145-167.

Laugwitz et al., "The human thyrotropin receptor: a heptahelical receptor capable of stimulating members of all four G protein families", *Proc Natl Acad Sci USA*, 1996, vol. 93, pp. 116-120.

Liu et al., "Cloning and pharmacological characterization of a fourth histamine receptor (H4) expressed in bone marrow", *Mol Pharmacol.*, 2001, vol. 59(3), pp. 420-426.

Liu et al., "Comparison of human, mouse, rat, and guinea pig histamine H4 receptors reveals substantial pharmacological species variation", *J Pharmacol Exp Ther.*, 2001, vol. 299(1), pp. 121-130.

Liu et al., "Identification of relaxin-3/INSL7 as a ligand for GPCR142", *J Biol Chem.*, 2003 vol. 278(50), pp. 50765-50770.

Liu et al., "Identification of relaxin-3/INSL7 as an endogenous ligand for the orphan G-protein-coupled receptor GPCR135", *J Biol Chem.*, 2003, vol. 278(50), pp. 50754-50764.

Liu et al., "INSL5 is a high affinity specific agonist for GPCR142 (GPR100)", *J Biol Chem.*, 2005, vol. 280(1), pp. 292-300.

Liu et al., "Relaxin-3/insulin-like peptide 5 chimeric peptide, a selective ligand for G protein-coupled receptor (GPCR)135 and GPCR142 over leucine-rich repeat-containing G protein-coupled receptor 7", *Mol Pharmacol.*, 2005, vol. 67(1), pp. 231-240.

Lok et al., "Identification of INSL6, a new member of the insulin family that is expressed in the testis of the human and rat", *Biol Reprod.*, 2000, vol. 62, pp. 1593-1599.

Maguire, "Discovering orphan receptor function using human in vitro pharmacology", *Curr Opin Pharmacol.*, 2003, vol. 3, pp. 135-139.

Matsumoto et al., "The novel G-protein coupled receptor SALPR shares sequence similarity with somatostatin and angiotensin receptors", *Gene*, 2000, vol. 248, pp. 183-189.

Montminy et al., "Regulation of cAMP-inducible genes by CREB", *TINS*, 1990, vol. 13(5), pp. 184-188.

Moss, "RNA interference: it's a small RNA world", *Curr Biol.*, 2001, vol. 11, pp. R772-R775.

Myers et al., "Optimal alignments in linear space", *CABIOS*, 1988, vol. 4(1), pp. 11-17.

O'Hara et al., "The ligand-binding domain in metabotropic glutamate receptors is related to bacterial periplasmic binding proteins", *Neuron*, 1993, vol. 11, pp. 41-52.

Osheroff et al., "Preparation of biologically active 32P-labeled human relaxin. Displaceable binding to rat uterus, cervix, and brain", *J Biol Chem.*, 1990, vol. 265(16), pp. 9396-9401.

Osheroff et al., "Autoradiographic localization of relaxin binding sites in rat brain", *Proc Natl Acad Sci USA*, 1991, vol. 88, pp. 6413-6417.

Pinkert et al., "An albumin enhancer located 10 kb upstream functions along with its promoter to direct efficient, liver-specific expression in transgenic mice", *Genes Dev.*, 1987, vol. 1, pp. 268-276.

Potter et al., "Distribution of corticotropin-releasing factor receptor mRNA expression in the rat brain and pituitary", *Proc Natl Acad Sci USA*, 1994, vol. 91, pp. 8777-8781.

Queen et al., "Immunoglobulin gene transcription is activated by downstream sequence elements", *Cell*, 1983, vol. 33, pp. 741-748.

Rattan et al., "Protein synthesis, posttranslational modifications, and aging", *Ann N Y Acad Sci.*, 1992, vol. 663, pp. 48-62.

Rinderknecht et al., "The amino acid sequence of human insulin-like growth factor I and its structural homology with proinsulin", *J Biol Chem.*, 1978, vol. 253(8), pp. 2769-2776.

Schultz et al., "Expression and secretion in yeast of a 400-kDa envelope glycoprotein derived from Epstein-Barr virus", *Gene*, 1987, vol. 54, pp. 113-123.

Scott et al., "Searching for peptide ligands with an epitope library", *Science*, 1990, vol. 249, pp. 386-390.

Seed, "An LFA-3 cDNA encodes a phospholipid-linked membrane protein homologous to its receptor CD2", *Nature*, 1987, vol. 329, pp. 840-842.

Seidah et al., "Proprotein and prohormone convertases: a family of subtilases generating diverse bioactive polypeptides", *Brain Res.*, 1999, vol. 848, pp. 45-62.

Seifter et al., "Analysis for protein modifications and nonprotein cofactors", *Methods Enzymol.*, 1990, vol. 182, pp. 626-646.

Shenker et al., "A constitutively activating mutation of the luteinizing hormone receptor in familial male precocious puberty", *Nature*, 1993, vol. 365, pp. 652-654.

Sherwood, "Relaxin's physiological roles and other diverse actions", *Endocr Rev.*, 2004, vol. 25(2), pp. 205-234.

Shimomura et al., "Identification of neuropeptide W as the endogenous ligand for orphan G-protein-coupled receptors GPR7 and GPR8", *J Biol Chem.*, 2002, vol. 277(39), pp. 35826-35832.

Simmons et al., "A complete protocol for in situ hybridization of messenger RNAs in brain and other tissues with radio-labeled single-stranded RNA probes", *J Histotech.*, 1989, vol. 12(3), pp. 169-181.

Singer et al., "Optimization of in situ hybridization using isotopic and non-isotopic detection methods", *Biotechniques*, 1986, vol. 4(3), pp. 230-246.

Smith et al., "Single-step purification of polypeptides expressed in *Escherichia coli* as fusions with glutathione S-transferase", *Gene*, 1988, vol. 67, pp. 31-40.

Somberg, "Digitalis: neurally mediated arrhythmogenic and coronary vasoconstrictor properties", *J Clin Pharmacol.*, 1985, vol. 25, pp. 529-539.

Studier et al., "Use of T7 RNA polymerase to direct expression of cloned genes", *Methods Enzymol.*, 1990, vol. 185, pp. 60-89.

Sudo et al., "H3 relaxin is a specific ligand for LGR7 and activates the receptor by interacting with both the ectodomain and the exoloop 2", *J Biol Chem.*, 2003, vol. 278(10), pp. 7855-7862.

Sunn et al., "Circulating relaxin acts on subfornical organ neurons to stimulate water drinking in the rat", *Proc Natl Acad Sci USA*, 2002, vol. 99(3), pp. 1701-1706.

Sutton et al., "Distribution of G-protein-coupled receptor (GPCR)135 binding sites and receptor mRNA in the rat brain suggests a role for relaxin-3 in neuroendocrine and sensory processing", *Neuro-endocrinology*, 2004, vol. 80, pp. 298-307.

Tan et al., "Quantitative autoradiographic studies of relaxin binding in rat atria, uterus and cerebral cortex: characterization and effects of oestrogen treatment", *Br J Pharmacol.*, 1999, vol. 127, pp. 91-98.

Tan et al., "Structural requirements for the interaction of sheep insulin-like factor 3 with relaxin receptors in rat atria", *Eur J Pharmacol.*, 2002, vol. 457, pp. 153-160.

Thomas et al., "Kex2-like endoproteases PC2 and PC3 accurately cleave a model prohormone in mammalian cells: evidence for a common core of neuroendocrine processing enzymes", *Proc Natl Acad Sci USA*, 1991, vol. 88, pp. 5297-5301.

Ullrich et al., "Human insulin receptor and its relationship to the tyrosine kinase family of oncogenes", *Nature*, 1985, vol. 313, pp. 756-761.

Ullrich et al., "Insulin-like growth factor I receptor primary structure: comparison with insulin receptor suggests structural determinants that define functional specificity", *EMBO J.*, 1986, vol. 5(10), pp. 2503-2512.

Vale et al., "Epidermal growth factor receptors on PC12 cells: alteration of binding properties by lectins", *J Cell Biochem.*, 1983, vol. 22, pp. 99-109.

Van Pett et al., "Distribution of mRNAs encoding CRF receptors in brain and pituitary of rat and mouse", *J Comp Neurol.*, 2000, vol. 428, pp. 191-212.

Ward et al., "Binding activities of a repertoire of single immunoglobulin variable domains secreted from *Escherichia coli*", *Nature*, 1989, vol. 341, pp. 544-546.

Weintraub et al., "Anti-sense RNA as a molecular tool for genetic analysis", *TIG*, 1985, pp. 22-25.

Wilson et al., "Orphan G-protein-coupled receptors: the next generation of drug targets?", *Br J Pharmacol.*, 1998, vol. 125, pp. 1387-1392.

Winoto et al., "A novel, inducible and T cell specific enhancer located at the 3' end of the T cell receptor alpha locus", *EMBO J.*, 1989, vol. 8(3), pp. 729-733.

Zakova et al., "Shortened insulin analogues: marked changes in biological activity resulting from replacement of TyrB26 and N-methylation of peptide bonds in the C-terminus of the B-chain", *Biochemistry*, 2004, vol. 43, pp. 2323-2331.

Zamore et al., "RNAi: double-stranded RNA directs the ATP-dependent cleavage of mRNA at 21 to 23 nucleotide intervals", *Cell*, 2000, vol. 101, pp. 25-33.

Zhao et al., "Mice without a functional relaxin gene are unable to deliver milk to their pups", *Endocrinology*, 1999, vol. 140(1), pp. 445-453.

Zuckerman et al., "Discovery of nanomolar ligands for 7-transmembrane G-protein-coupled receptors from a diverse N-(substituted)glycine peptoid library", *J Med Chem.*, 1994, vol. 37, pp. 2678-2685.

* cited by examiner

Figure 2

| | B-chain | | A-chain | |
|---|---|---|---|---|
| Relaxin-3 | RAAPYGVRLCGREFIRAVIFTCGGSRW | (SEQ ID NO:89) | DVLAGLSSSCCKWGCSKSEISSLC | (SEQ ID NO:90) |
| R3/R1 | RAAPYGVRLCGREFIRAVIFTCGGSRW | (SEQ ID NO:89) | RPYVALFEKCCLIGCTKRSLAKYC | (SEQ ID NO:91) |
| R3/R2 | RAAPYGVRLCGREFIRAVIFTCGGSRW | (SEQ ID NO:89) | QLYSALANKCCHVGCTKRSLARFC | (SEQ ID NO:92) |
| R3/I3 | RAAPYGVRLCGREFIRAVIFTCGGSRW | (SEQ ID NO:89) | ATNPARYCCLSGCTQQDLLTLC | (SEQ ID NO:93) |
| R3/I4 | RAAPYGVRLCGREFIRAVIFTCGGSRW | (SEQ ID NO:89) | FDPFCCEVICDDGTSVKLC | (SEQ ID NO:94) |
| R3/I5 | RAAPYGVRLCGREFIRAVIFTCGGSRW | (SEQ ID NO:89) | DLQTLCCTDGCSMTDLSALC | (SEQ ID NO:95) |
| R3/I6 | RAAPYGVRLCGREFIRAVIFTCGGSRW | (SEQ ID NO:89) | GYSEKCCLTGCTKEELSIAC | (SEQ ID NO:96) |
| R3/I | RAAPYGVRLCGREFIRAVIFTCGGSRW | (SEQ ID NO:89) | GIVEQCCTSICSLYQLENYC | (SEQ ID NO:97) |
| R3/A | RAAPYGVRLCGREFIRAVIFTCGGSRW | (SEQ ID NO:89) | GLYENCCLSICDDYEIEKAC | (SEQ ID NO:98) |

Figure 6

|  | | B-chain | A-chain |
|---|---|---|---|
| Relaxin Subfamily | Relaxin-1: | KWKDDVIKLCGRELVRAQIAICGMSTWS | RPYVALFEKCCLIGCTKRSLAKYC |
| | Relaxin-2: | DSWMEEVIKLCGRELVRAQIAICGMSTWS | QLYSALANKCCHVGCTKRSLARFC |
| | Relaxin-3: | RAAPYGVRLCGREFIRAVIFTCGGSRW | DVLAGLSSSCCKWGCSKSEISSLC |
| | INSL3: | PTPEMREKLCGHHFVRALVRVCGGPRWSTEA | NPARYCCLSGCTQQDLLTLC |
| | *INSL4: | ESLAAELRGCGPRFGKHLLSYCPMPEK | SGRHRFDPFCCEVICDDGTSVKLCT |
| | *INSL5: | KESVRLCGLEYIRTVIYICASSRW | QDLQTLCCTDGCSMTDLSALC |
| | *INSL6: | ISSARKLCGRYLVKEIEKLCGHANWSQF | GYSEKCCLTGCTKEELSIACLPYIDFKRL |
| Insulin Subfamily | Insulin: | FVNQHLCGSHLVEALYLVCGERGFFYTPKT | GIVEQCCTSICSLYQLENYCN |
| | IGF1: | GPETLCGAELVDALQFVCGDRGFYFNKPTGYGSSSRRAPQTGIVDECCFRSCDLRRLEMYCAPLKPAKSA |  |
| | IGF2: | AYRPSETLCGGELVDTLQFVCGDRGFYFSRP-ASRVSRRSR---GIVEECCFRSCDLALLETYCATPAKSE |  |

RELAXIN-3 CHIMERIC POLYPEPTIDES AND THEIR PREPARATION AND USE

FIELD OF THE INVENTION

The invention generally relates to biologically active relaxin-3 chimeric polypeptides and their preparation and use, e.g., as assay reagents.

BACKGROUND OF THE INVENTION

Relaxin-3 (also known as INSL7) has been found to be a ligand for the G-protein coupled receptors (GPCRs) GPCR135 and GPCR142. See U.S. Provisional Application No. 60/493,941, filed 7 Aug. 2003, and International Application No. PCT/US2004/005666, filed 25 Feb. 2004, the disclosures of which are incorporated by reference herein.

GPCRs are transmembrane receptor proteins that are responsible for the transduction of a diverse array of extracellular signals, including hormones, neurotransmitters, peptides, lipids, ions, light, odorants, nucleotides, fatty acid derivatives, and other chemical mediators. See, e.g., WIPO Publication No. WO 02/00719. GPCRs are of particular importance to drug discovery because they have been established as excellent drug targets: they are the targets of 50% of marketed drugs. An increasing number of diseases have been found to be associated with GPCRs. Drugs targeting GPCRs have been used to treat a wide range of disorders from cardiovascular to gastrointestinal to CNS and others (Wilson et al., 1998, British J. of Pharmacology, 125:1387-1392).

The GPCR-mediated signal transduction event is often initiated upon binding of a specific ligand to the GPCR. Each GPCR is composed of an extracellular N-terminal domain, seven distinct transmembrane segments, and an intracellular C-terminal domain. Binding of the ligand to an extracellular N-terminal domain, transmembrane domain, or intracellular loop of a GPCR results in a conformational change that leads to activation of intracellular heterotrimeric GTP-binding proteins (G proteins) associated with the GPCR. These activated G proteins in turn mediate a variety of intracellular responses that regulate cell physiology. Therefore, the ligand provides means of elucidating the physiological function of the GPCR as well as methods of screening for compounds that regulate the signal transduction activity of the GPCR.

At present, only about 200 GPCRs are classified as known GPCRs that are activated by around 70 known ligands. Through sequence analyses, it was discovered that GPCRs belong to one of the largest superfamilies of the human genome: evaluated at over 1000 genes encoding GPCRs (Civelli et al., 2001, Trends in Neurosciences, 24:230-237). A large number of putative GPCRs are described as orphan receptors because their natural ligands are unknown. Some of these uncharacterized orphan GPCRs may be useful as therapeutic targets. The identification of the specific ligand to a GPCR is the key to harnessing the potential therapeutic benefits of these orphan GPCRs (Howard et al., 2001, Trends in Pharmacological Sciences, 22:132-140).

As noted above, relaxin-3 (also known as INSL7) has been found to be a ligand for GPCR135 as well as for GPCR142. See Liu et al., 2003, Journal of Biological Chemistry, 278: 50754-50764; and Liu et al., 2003, Journal of Biological Chemistry, 278:50765-50770. Relaxin-3 is a member of the insulin/relaxin superfamily. Members in this family are characterized by peptide subunits (A-chain and B-chain) linked by three disulfide bonds. Two of the three disulfide bonds are inter-subunit bonds and another one is an intra-chain bond in the A-chain. In the family, insulin, IGF1, and IGF2 have been reported to be involved in the regulation of glucose metabolism and signal through tyrosine kinase/growth factor receptors, which are single transmembrane receptors. Another member of the relaxin/insulin superfamily is Insulin-Like (INSL) 5 (Conklin et al. 1999, Genomics, 60(1):50-56), which is believed to be a selective ligand for GPCR142 (see, e.g., U.S. Provisional Application No. 60/580,083, the disclosure of which is incorporated by reference herein). Two other members in the family are relaxin and INSL3, ligands for LGR7 and/or LGR8, which are GPCRs with leucine-rich repeats at the N-terminal extra-cellular domain. Relaxin-3 was also reported to be an additional ligand for LGR7.

The GPCR142 expression pattern is distinct from that of GPCR135 and relaxin-3 with an abundant peripheral tissue distribution in addition to expression in the brain (Liu et al., 2003, Journal of Biological Chemistry, 278(50):50765-50770)). We have found that GPCR142 is highly conserved among human, monkey, cow, and pig, but is less conserved in the mouse, and a pseudo-gene exists in the rat despite a fair degree of conservation of relaxin-3 genes in both rodent species, suggesting that GPCR142 has a distinct function from GPCR135 and diminished function in the rodents. All the physiological functions of GPCR135 and GPCR142 remain to be fully elucidated. In vivo administration of relaxin-3 also activates LGR7, which is expressed in both the brain and periphery (Hsu et al., 2000, Mol. Endocrinol., 14:1257-1271; Hsu et al., 2002, Science, 295:671-674; Tan et al., 1999, Br. J. Pharmacol., 127:91-98). Thus, in vivo study of GPCR135 or GPCR142 functions has been confounded by the lack of selective pharmacological tools for these two receptor subtypes.

SUMMARY OF THE INVENTION

Biologically active chimeric polypeptides of relaxin-3 have now been discovered.

Thus, in one general aspect, the invention relates to a biologically active relaxin-3 chimeric polypeptide comprising a relaxin-3 B-chain and a relaxin/insulin polypeptide family member A-chain. In preferred embodiments, the A-chain is a relaxin-1 A-chain, a relaxin-2 A-chain, an insulin-like 3 A-chain, an insulin-like 4 A-chain, an insulin-like 5 A-chain, or an insulin-like 6 A-chain. More preferably, the A-chain is an insulin-like 5 A-chain. Even more preferably, the chimeric peptide is human relaxin-3 A-chain/human INSL5 B-chain having an amino acid sequence as set forth in SEQ ID NO:23.

The invention is also directed to polynucleotides encoding the above polypeptides. Thus, in one general aspect the invention relates to a relaxin-3 chimeric pre-propolypeptide comprising a relaxin B-chain joined by a first peptide linkage to a relaxin C-chain, the C-chain further joined by a second peptide linkage to a relaxin/insulin family member A-chain, and a protease cleavage site inserted at at least one location selected from the second peptide linkage between the A-chain and C-chain and the first peptide linkage between the C-chain and the B-chain of the relaxin-3 chimeric pre-propolypeptide. In a preferred embodiment, the protease cleavage site, preferably a furin cleavage site, is inserted at the peptide linkage joining the C-chain and A-chain. Preferably, the polynucleotide has a nucleotide sequence selected from the polynucleotide having a nucleotide sequence as set forth in SEQ ID NO:7 and complements thereof which hybridize under stringent conditions to such polynucleotide.

In another aspect, the invention is directed to pre-propolypeptides encoded by such polynucleotides.

In yet another aspect, the invention relates to expression vectors suitable for expression in recombinant host cells, the vector comprising the above-mentioned polynucleotides.

Another aspect of the invention relates to host cells comprising the expression vectors.

An additional general aspect of the invention relates to a receptor-ligand complex comprising a receptor component comprising GPCR135 or GPCR142, the receptor component bound to a ligand component comprising a biologically active relaxin-3 chimeric polypeptide. In preferred embodiments, the polypeptide corresponds to SEQ ID NO:23 and bears a radioisotope label. In other preferred embodiments, the receptor component comprises GPCR135 and/or GPCR142 associated with isolated cell membranes or lipid vesicles. Preferably, the receptor and ligand components are each in a substantially pure form.

In a further general aspect, the invention relates to a process of producing a mature relaxin-3 chimeric polypeptide from a recombinant cell, comprising: (a) transforming or transfecting a host cell with a first expression vector as described above and a second vector expressing a protease for cleaving a relaxin-3 chimeric pre-propolypeptide at an inserted protease cleavage site; and growing the host cell so that both the relaxin-3 chimeric pre-propolypeptide and the protease are expressed, whereby the protease cleaves a peptide linkage at the inserted protease cleavage site on the relaxin-3 chimeric pre-propolypeptide, yielding a mature relaxin-3 chimeric polypeptide. Preferably the process further comprises: expressing a receptor component on the cell surface of a host cell that has been transformed or transfected with an expression vector encoding GPCR135 or GPCR142; and complexing the receptor component with the relaxin-3 chimeric polypeptide.

The invention also generally relates to a method of identifying a compound that modulates a biological activity of GPCR135 and/or GPCR142, comprising: (a) contacting a test sample comprising a compound with an assay reagent comprising the receptor and a biologically active relaxin-3 chimeric polypeptide; (b) then determining the biological activity of the receptor; and (c) comparing the biological activity determined with a control measurement obtained by contacting a control sample not containing the compound with the assay reagent. Preferably, the receptor is a component of a biological sample derived from a rat or a human. Determination of the biological activity may comprise identifying the formation of a receptor-ligand complex (e.g., using autoradiography) or measuring a second messenger response (e.g., by intracellular calcium ion concentration or intracellular cAMP concentration). For example, the receptor may be associated with isolated cell membranes from a GPCR135 host cell or a GPCR142 host cell, and the biological activity may be determined by measuring the amount of protein phosphorylation of the isolated membranes using a γ-phosphate labeled GTP molecule such as $^{35}$S-GTPγS, $^{33}$P-GTPγP, or $^{32}$P-GTPγP.

In another aspect, the invention provides a method of identifying a compound that binds to at least one receptor selected from GPCR135 and GPCR142, comprising: (a) contacting the receptor with a test compound and with a labeled relaxin-3 chimeric polypeptide; (b) determining the amount of the labeled relaxin-3 chimeric polypeptide that binds to the receptor; and (c) comparing the amount determined in step (b) with a control measurement obtained by contacting the receptor with the labeled relaxin-3 chimeric polypeptide in the absence of the test compound.

Other aspects, features and advantages of the invention will be apparent from the following disclosure, including the detailed description of the invention and its preferred embodiments and the appended claims.

BRIEF DESCRIPTION OF THE DRAWINGS

In FIG. 1A, SK-N-MC/β-gal cells expressing human GPCR135 were stimulated with relaxin-3, relaxin-3 B-chain, porcine relaxin, or INSL3 at various concentrations to inhibit the forskolin stimulated β-galactosidase expression. Forskolin was added to cells at a final concentration of 5 μM to stimulate the β-galactosidase expression. FIG. 1B depicts results for SK-N-MC/β-gal cells expressing human GPCR142 stimulated as in FIG. 1A. In FIG. 1C, SK-N-MC/β-gal cells expressing human LGR7 were stimulated with relaxin-3, relaxin-3 B-chain, porcine relaxin, and INSL3 at various concentrations to induce the β-galactosidase expression. The intracellular β-galactosidase activities were measured by a colorimetric assay using CRGP as the substrate and reading the absorbance at a wavelength of 570 nm. For FIG. 1D, SK-N-MC/β-gal cells expressing human LGR8 were stimulated as in FIG. 1C.

FIG. 2 shows the amino acid sequences of human relaxin-3 and relaxin-3 chimeric polypeptides. A chimeric polypeptide is a hybrid molecule containing specific units from different proteins or polypeptides. All chimeric polypeptides depicted have the identical B-chain from human relaxin-3 (SEQ ID NO: 89). The chimeric polypeptides $R_3/R_1$, $R_3/R_2$, $R_3/I_3$, $R_3/I_4$, $R_3/I_5$, $R_3/I_6$, and $R_3/I$ possess A-chain sequences from human relaxin-1 (SEQ ID NO: 91), relaxin-2 (SEQ ID NO: 92), INSL3 (SEQ ID NO: 93), INSL4 (SEQ ID NO: 94), INSL5 (SEQ ID NO: 95), INSL6 (SEQ ID NO: 96), and insulin (SEQ ID NO: 97), respectively. R3/A possesses an A-chain (SEQ ID NO: 98) in which the conserved cysteine residues are retained and the remainder of the amino acid sequence is arbitrarily assigned.

Figure 5A:
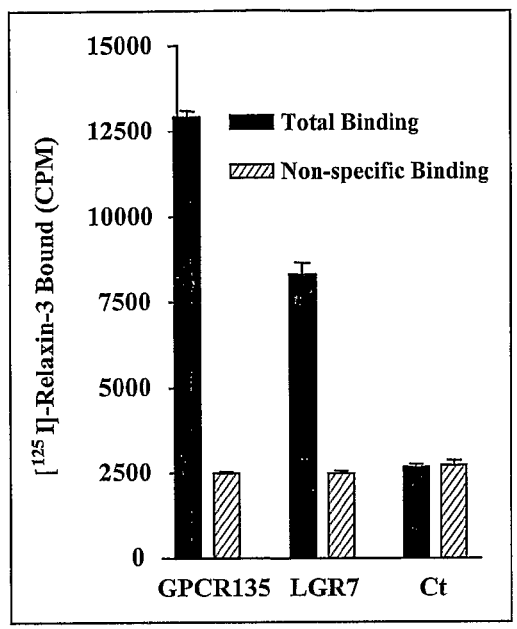
Figure 5B:
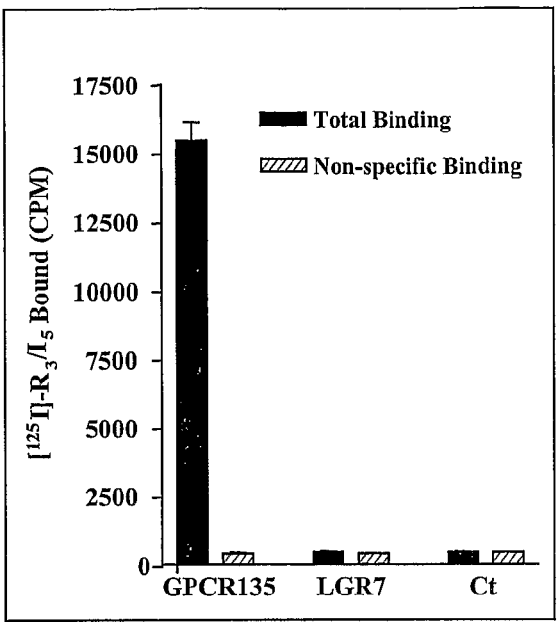
Figure 5C:
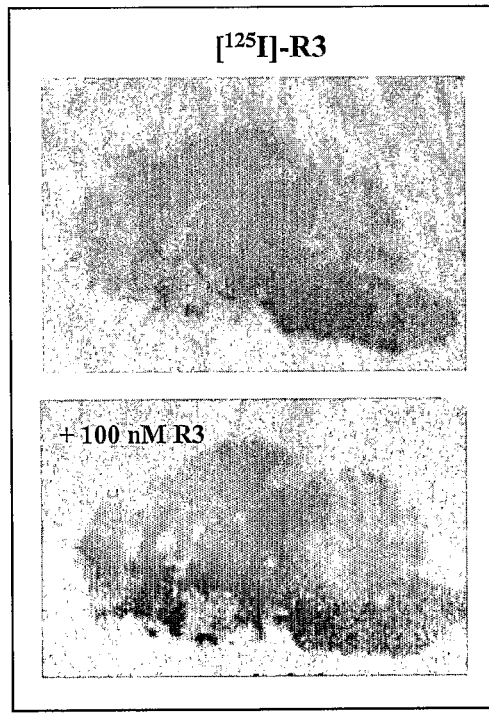
Figure 5D:
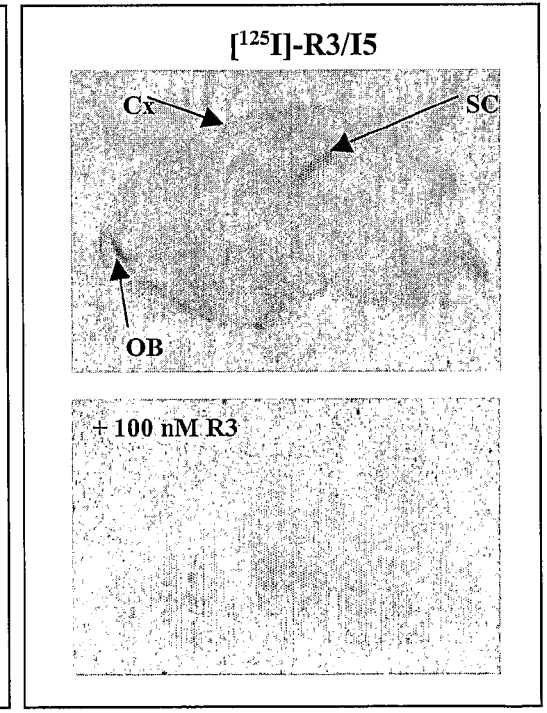

FIGS. 5A-5D illustrate a comparative analysis of the binding specificities of [$^{125}$I]-relaxin-3 and [$^{125}$I]-$R_3/I_5$ for GPCR135 and LGR7. COS-7 cells in 6-well culture dishes were transfected with human GPCR135 and LGR7, respectively. Mock transfected COS-7 cells were used as the negative controls. [$^{125}$I]-relaxin-3 (FIG. 5A) or [$^{125}$I]-$R_3/I_5$ (FIG. 5B) was added to cells at a final concentration of 100 pM either in the absence or presence of 1 uM of unlabeled relaxin-3 to determine total binding and non-specific binding, respectively. FIG. 5C depicts an autoradiogram of [$^{125}$]-relaxin-3 binding in rat brain sagittal section. FIG. 5D depicts an autoradiogram of non-specific binding of [$^{125}$]-relaxin-3 as determined in the presence of 100 nM of unlabeled relaxin-3. FIG. 5E depicts an autoradiogram of [$^{125}$]-$R_3/I_5$ binding in rat brain sagittal section. FIG. 5E depicts non-specific binding of [$^{125}$]-$R_3/I_5$ as determined in the presence of 100 nM of unlabeled relaxin-3. CX=Cortex, OB=Olfactory Bulb, SC=Superior Colliculus.

FIG. 6 provides an amino acid sequence comparison of members of the insulin/relaxin family. The two conserved positively charged amino acids in the B-chains of relaxin-1 (SEQ ID NO:80), relaxin-2 (SEQ ID NO:81), relaxin-3 (SEQ ID NO:28), INSL3 (SEQ ID NO:82), INSL4 (SEQ ID NO:83), INSL5 (SEQ ID NO:84), and INSL6 (SEQ ID NO:85) are highlighted in bold letters. The asterisk (*) denotes that B-chain and A-chain termini for INSL4, INSL5, and INSL6 are based on predictions. The amino acid sequences of insulin (SEQ ID NO:86), insulin-like growth factor (IGF) I (SEQ ID NO:87), and IGF2 (SEQ ID NO:88) are also provided.

Figure 7A:
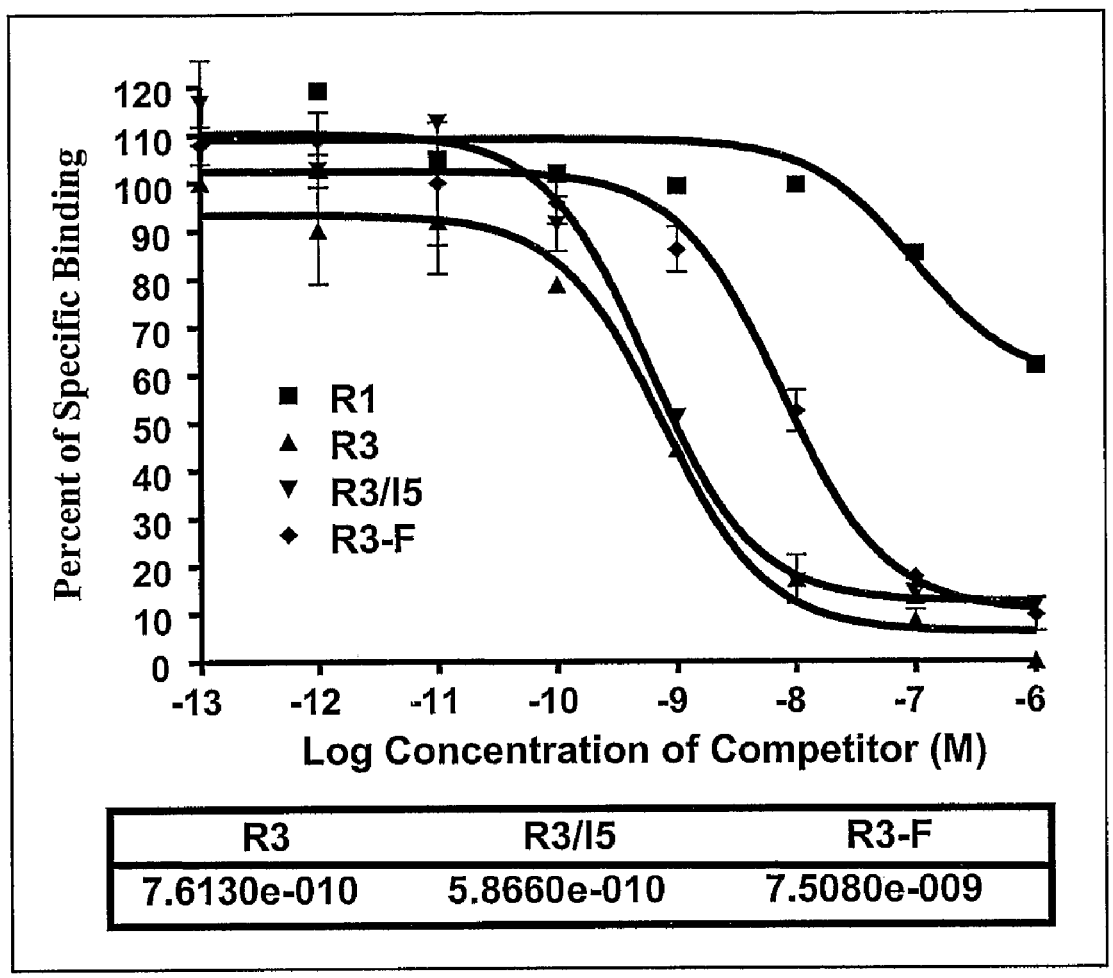
Figure 7B:
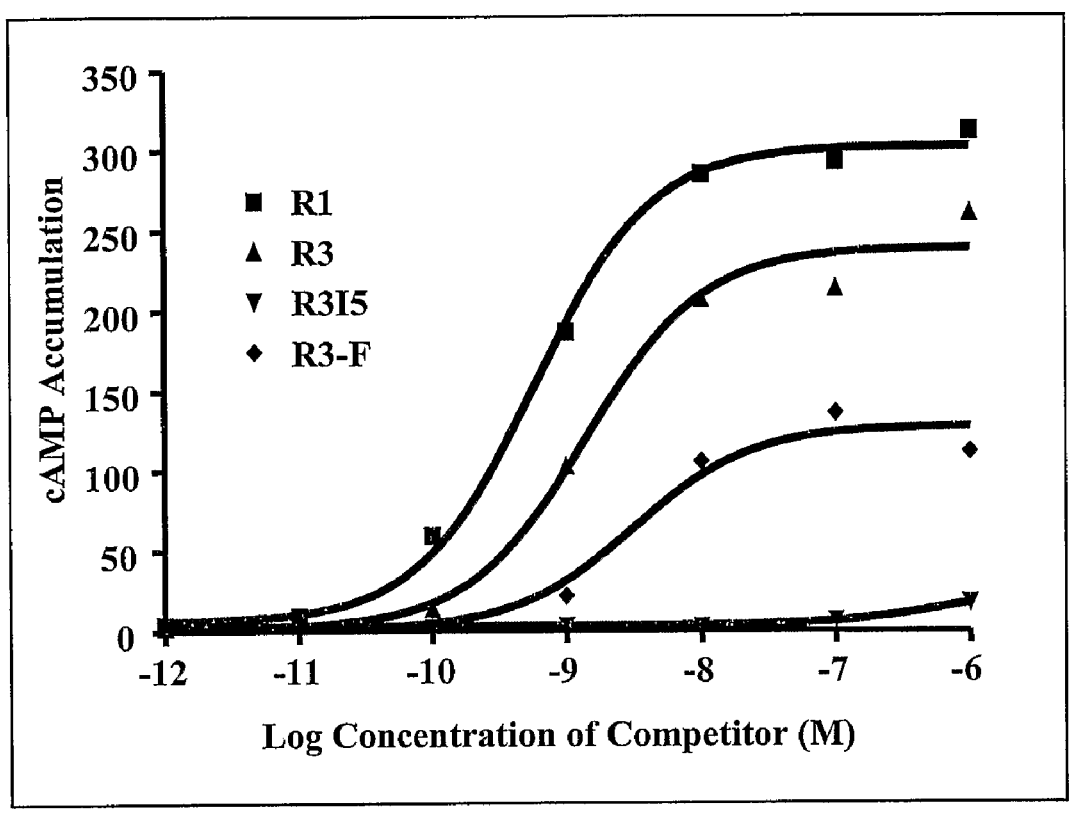

FIGS. 7A-7B illustrate a characterization of the selectivity of the R3/I5 chimera as a ligand for rat GPCR135 receptors compared to rat LGR7 in recombinant cells. The R3/I5 chimera was characterized for its receptor binding properties for rat recombinant GPCR135 (FIG. 7A) or LGR7 (FIG. 7B) receptors. [$^{125}$I]-R3 was used as tracer (100 pM). Data shown are the mean values±SEM of triplicate experiments.

Figure 8:
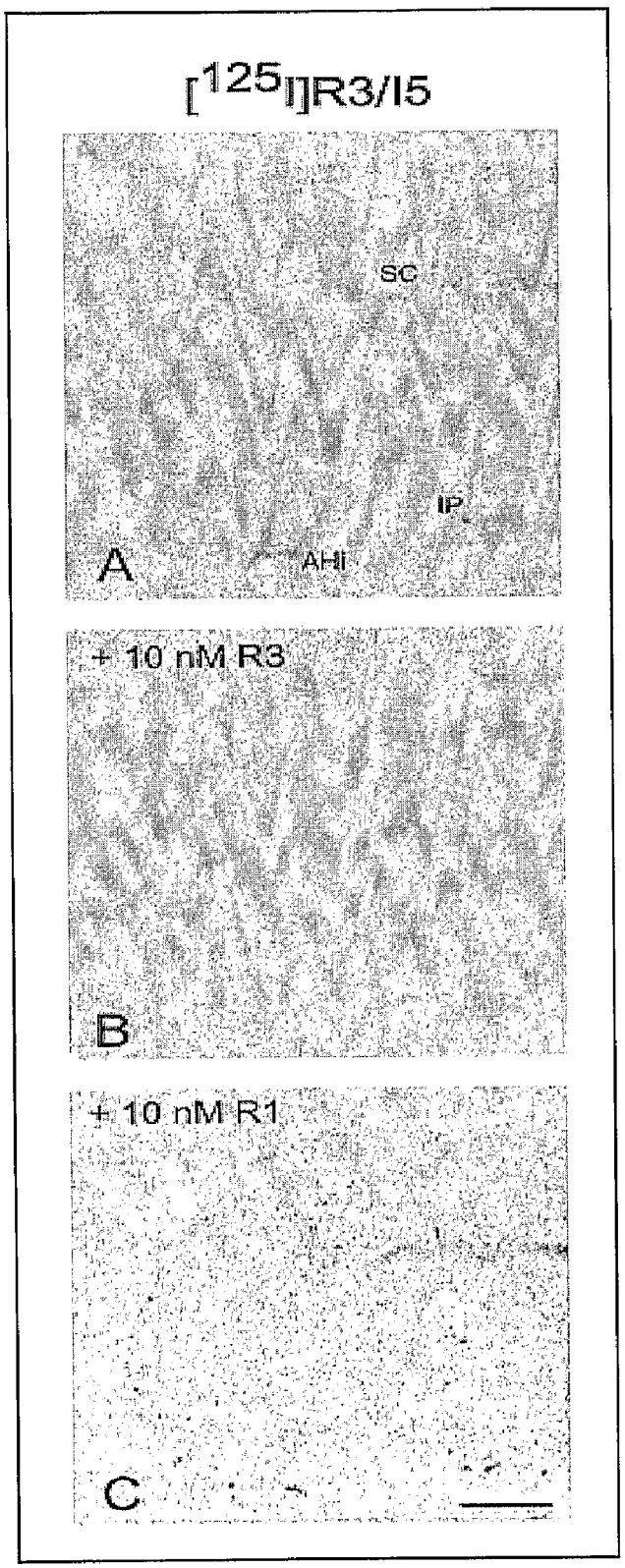

FIGS. 8A-8C depict a pharmacological characterization of [$^{125}$I]-R3/I5 binding sites in autoradiograms from a series of coronal sections at the level of the rat superior colliculus (left hemisphere): 7 pM [$^{125}$I]-R3/I5 (FIG. 8A) was competed with 10 nM R3 (FIG. 8B) or 100 nM Relaxin (FIG. 8C). In the figures, SC=superior colliculus; I.P.=interpeduncular nucleus; AHi=amygdalohippocampal area.

Figure 9:
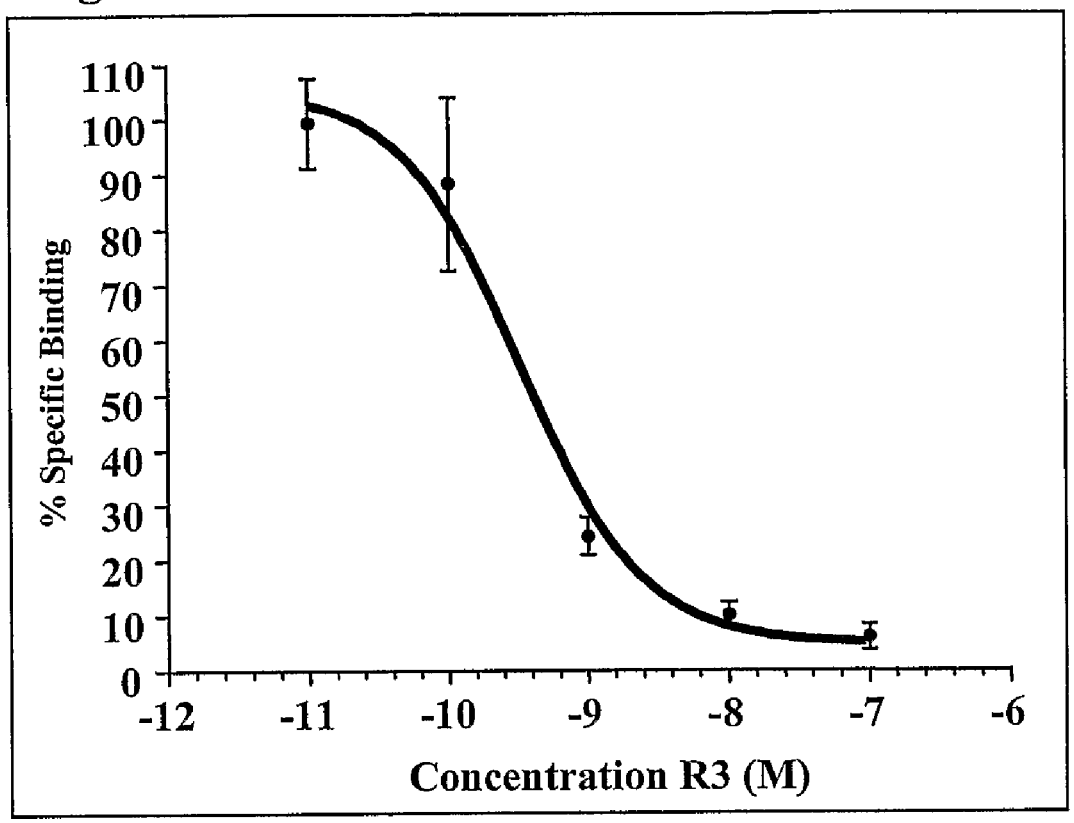

FIG. 9 shows displacement of [$^{125}$I]-R3/I5 binding sites to the rat superior colliculus by unlabeled R3 as determined by quantitative autoradiography. Consecutive coronal sections were incubated with 7 pM of [$^{125}$I]-R3/I5 in the presence of increasing concentrations of R3. Data are the means±SEM of triplicate experiments.

FIGS. 10A-10F'' illustrate a rostro-caudal distribution of GRPC135 mRNA (FIGS. 10A, 10B, 10C, 10D, 10E, and 10F) and [$^{125}$I]-R3/I5 binding sites (FIGS. 10A', 10B', 10C', 10D', 10E', and 10F') in autoradiograms from a series of coronal sections through rat front and mid brain (left hemisphere). Non-specific binding was determined in the presence of 100 nM R3 (FIGS. 10A'', 10B'', 10C'', 10D'', 10E'', and 10F''). In the figures, Amyg=amygdala; BNST=bed nucleus of stria terminalis; CA3=field of CA3 of hippocampus; CM=central thalamic nucleus; DG=dentate gyrus; Ha=habenula; LH=lateral hypothalamus; MCx=motor cortex; OB=olfactory bulb; ON=olfactory nucleus; PVA=paraventricular thalamic nucleus; PVN=paraventricular hypothalamic nucleus; S=septum; SCx=somatosensory cortex; SO=supraoptic nucleus.

FIGS. 11A-11F'' illustrate a rostro-caudal distribution of GRPC135 mRNA (FIGS. 11A, 11B, 11C, 11D, 11E, 11F) and [$^{125}$I]-R3/I5 binding sites (FIGS. 11A', 11B', 11C', 11D', 11E', 11F') in autoradiograms from a series of coronal section through the rat hind brain (left hemisphere). Non-specific binding was determined in the presence of 100 nM R3 (11A'', 11B'', 11C'', 11D'', 11E'', 11F''). AHi=amygdalohippocampal area; DG=dentate gyrus; DRD=dorsal raphe dorsal part; IC=inferior colliculus; IP=interpeduncular nucleus; NI=nucleus incertus; PAG=periaqueductal gray area; SC=superior colliculus; Sol=nucleus of solitary tract; Sp5=Spinal trigeminal tract; TCx=temporal cortex; VCx=visual cortex.

DETAILED DESCRIPTION OF THE INVENTION AND ITS PREFERRED EMBODIMENTS

The disclosures of all publications cited herein, or corresponding to accession numbers cited herein, are hereby incorporated by reference. Unless defined herein or otherwise indicated below, all technical and scientific terms used herein have the same meaning as commonly understood in the art.

As used herein, the terms "comprising", "including", and "containing" are used in their open, non-limiting sense.

The following are abbreviations that may at times be used in this specification:
bp=base pair
$Ca^{2+}$=calcium ion
cAMP=cyclic adenosine monophosphate
cDNA=complementary DNA
CNS=central nervous system
kb=kilobase; 1000 base pairs
kDa=kilodalton; 1000 dalton
GPCR=G protein coupled receptor
G protein=GTP-binding protein
GTP=guanosine 5'-triphosphate
nt=nucleotide
PAGE=polyacrylamide gel electrophoresis
PCR=polymerase chain reaction
SDS=sodium dodecyl sulfate
SiRNA=small interfering RNA
UTR=untranslated region As noted above, certain general embodiments of the invention relate to isolated biologically active relaxin-3 chimeric polypeptides, polynucleotides that encode immature pre-propolypeptides from which the relaxin-3 chimeric polypeptides are derived, expression vectors comprising such polynucleotides, and recombinant host cells transfected or transformed by such vectors.

Exemplary relaxin-3 polypeptides include relaxin-3 orthologs that have been identified in human (GenBank protein Accession No.: NP_543140), rat (SEQ ID NO:51) (Burazin et al., 2002, *J. Neurochem.*, 82: 1553-1557; GenBank protein Accession No. NP_733767; 76.4% sequence identity to that of human), mouse (SEQ ID NO: 49)(Bathgate et al., 2002, *J. Biol. Chem.*, 277: 1148-1157; GenBank protein accession number XP_146603; 78.7% sequence identity to that of human), and other animals, including pig and monkey. These polypeptides can be used as sources of relaxin-3 units to form suitable chimera.

A "relaxin-3 chimeric polypeptide", or "ligand component" means a mature relaxin-3 chimeric polypeptide, or active fragment thereof, which is a secreted protein containing a relaxin-3 polypeptide B-chain and a relaxin/insulin family member A-chain, linked by disulfide bridges or bonds, or a functionally equivalent fragment of such mature polypeptide or secreted protein.

A "relaxin/insulin family member" is, in reference to a specified polypeptide, a polypeptide that bears functional homology (e.g., has similar biological activity, such as association with similar types of receptors) or amino acid sequence homology. Exemplary relaxin/insulin family member polypeptides include relaxin polypeptides, such as relaxin-1, relaxin-2, relaxin-3, and insulin-like polypeptides, also termed INSLs, such as insulin-like 3 (INSL3), insulin-like 4 (INSL4), insulin-like 5 (INSL5), and insulin-like 6 (INSL6). Exemplary orthologs of relaxin/insulin family members include orthologs identified in the accompanying Sequence Listing. Thus, in exemplary embodiments, the relaxin-3 chimeric polypeptides are derived from a relaxin-3 component and a relaxin/insulin family member component from any of the relaxin/insulin family member orthologs described above.

A "relaxin-3 chimeric pre-propolypeptide" means a precursor of a relaxin-3 chimeric polypeptide.

Preferred embodiments of a relaxin-3 chimeric pre-propolypeptides and polypeptides include, e.g., (1) pre-propolypeptides and mature polypeptides that have at least 50% more preferably at least 60%, more preferably at least 70%, more preferably at least 80%, more preferably at least 90%, and even more preferably 100% amino acid sequence identity to the following chimera (B-chain/A-chain): human relaxin-3/relaxin-1 pre-propolypeptide (SEQ ID NO:11) and mature polypeptide (SEQ ID NO:19), a human relaxin-3/relaxin-2 pre-propolypeptide (SEQ ID NO:12) and mature polypeptide (SEQ ID NO:20), a human relaxin-3/INSL3 pre-propolypeptide (SEQ ID NO:13) and mature polypeptide (SEQ ID NO:21), a human relaxin-3/INSL4 pre-propolypeptide (SEQ ID NO:14) and mature polypeptide (SEQ ID NO:22), a human relaxin-3/INSL5 pre-propolypeptide (SEQ ID NO:15) and mature polypeptide (SEQ ID NO:23), or a human relaxin-3/INSL6 pre-propolypeptide (SEQ ID NO:16) and mature polypeptide (SEQ ID NO:24); or (2) pre-propolypeptides or polypeptides that are capable of binding to antibodies, e.g., polyclonal or monoclonal antibodies, raised against such relaxin-3 chimeric polypeptides.

A polypeptide or polynucleotide that is "biologically active" exerts a biological activity as determined in vivo or in vitro. Such activities can be a direct activity, such as an association with or an enzymatic activity on a second protein, or an indirect activity, such as a cellular signaling activity mediated by interaction of the protein with a second protein. Biological activities may be measured according to standard techniques, such as the exemplary techniques described below.

For example, a biological activity possessed by a preferred relaxin-3 chimeric polypeptide described below is its ability to bind with high affinity to a GPCR135 or a GPCR142, while not binding to an LGR7 or LGR8, thereby selectively stimulating either GPCR135 or GPRC142 and signal transduction events governed therewith. An exemplary biological activity of GPCR135 or GPCR142 is that, upon binding to a relaxin-3 chimeric polypeptide, the GPCR135 or GPCR142 activates a chain of events that alters the concentration of intracellular signaling molecules (second messenger molecule), such as cyclic AMP (cAMP) and calcium via activating a G-protein, which has a high affinity for GTP. These intracellular signaling molecules in turn alter the physiology and behavior of the cell.

As used herein, "GPCR135" and "GPCR142" each refers to a polypeptide that: (1) has greater than about 60% sequence identity to the human receptor protein (GPCR135 or GPCR142, as the case may be); (2) is capable of binding to antibodies, e.g., polyclonal or monoclonal antibodies, raised against the human protein; or (3) is encoded by a polynucleotide that specifically hybridizes under stringent hybridization conditions to a nucleic acid molecule having a sequence that has greater than about 60% nucleotide sequence identity to the human receptor cDNA.

A "receptor component" refers to either GPCR135 or a GPCR142, or an active fragment of either a GPCR135 or a GPCR142.

In preferred embodiments, the receptor component is a biologically active polypeptide having greater than 65, 70, 75, 80, 85, 90, or 95 percent, even more preferably having 100%, amino acid sequence identity either to human GPCR135 or human GPCR142. In other preferred embodiments, the receptor component is a polypeptide encoded by a polynucleotide that specifically hybridizes under stringent hybridization conditions to a nucleic acid molecule having a sequence that has greater than 65, 70, 75, 80, 85, 90, or 95 percent nucleotide sequence identity to human GPCR135 cDNA or human GPCR142 cDNA.

GPCR135 is also called SALPR (Matsumoto et al., 2000, *Gene*, 248:183-189; GenBank Protein Accession No.: BAA93001; GenBank nucleotide Accession No.: D88437 for cDNA). Exemplary GPCR135 molecules include orthologs that have been identified in human (SEQ ID NO:25, GenBank Accession Numbers: BAA93001, Q9NSD7, and NP_057652), rat (SEQ ID NO:46, and SEQ ID NO:47, 85.9% sequence identity to that of human), mouse (SEQ ID NO:45, 86.4% sequence identity to that of human), and other animals, including pig and monkey. An active fragment of a receptor GPCR135 means any fragment of the receptor protein that maintains its biological activity, such as binding to a mammalian relaxin3 and activating a G-protein. The protein or cDNA sequence of human GPCR135 has been disclosed in WIPO Publication Nos. WO00/23111, WO00/24891, WO01/48189, WO01/62797, WO01/74904, and WO01/85791.

Preferred GPCR142 orthologs include human GPCR142 (SEQ ID NO:27), mouse GPCR142 (SEQ ID NO:26), monkey GPCR142 (SEQ ID NO:29), bovine GPCR142 (SEQ ID NO:30), and porcine GPCR142 (SEQ ID NO:31). An active fragment of GPCR142 means a polypeptide that maintains the biological activity of a GPCR142, such as binding to a mammalian relaxin3 and activating a G-protein. The cDNA or protein sequence of human GPCR142 is provided in U.S. Pat. No. 5,955,309 and WIPO Publication Nos. WO 01/36471, WO 02/61087, and WO 02/00719.

In preferred embodiments, the relaxin-3 chimeric polypeptides are isolated or purified. An "isolated" or "purified" polypeptide is intended to refer to one that is substantially free of cellular material or protein contaminants from the cell or tissue source from which the polypeptide is produced and isolated, or substantially free of chemical precursors or other chemicals when the polypeptide is chemically synthesized. For example, polypeptide that is substantially free of cellular material can include preparations containing less than about 30%, or preferably 20%, or more preferably 10%, or even more preferably 5% (by dry weight) of contaminating proteins. When the polypeptide is recombinantly produced, it is also preferably substantially free of culture medium, e.g., culture medium representing less than about 20%, or more preferably 10%, or even more preferably 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the polypeptide or protein have less than about 30%, or preferably 20%, or more preferably 10%, or even more preferably 5% (by dry weight) of chemical precursors or compounds other than the polypeptide of interest.

Biologically active polypeptides can have several different physical forms. The polypeptide can exist as a full-length nascent or unprocessed polypeptide, or as partially processed polypeptides or combinations of processed polypeptides. The full-length nascent polypeptide can be post-translationally modified by specific proteolytic cleavage events that result in the formation of fragments of the full-length nascent polypeptide. A fragment, or physical association of fragments, can have the biological activity associated with the full-length polypeptide; of course, the degree of biological activity associated with individual fragments can vary.

An "active fragment" of a specified polypeptide means a fragment or derivative of such polypeptide that maintains biological activity of the polypeptide. For example, active fragments may be obtained by making appropriate deletions, substitutions or additions to a full-length protein that result in a modified sequence that maintains the desired biological activity and possesses conserved motifs. Biological activity of, e.g., a relaxin-3/INSL5 chimeric polypeptide active fragment can be evidenced, for example, by an ability to selectively bind to and stimulate a GPCR135 or a GPCR142, while not binding or stimulating to an LGR7 or an LGR8.

It is within the purview of one of ordinary skill in the art to determine which amino acid residues or nucleotides may be added, deleted, or replaced in the full-length polypeptide or polynucleotide encoding it without abolishing biological activities of interest, such as the ability of the inventive relaxin-3 chimeric polypeptides to selectively bind to GPCR135 or GPCR142, in order to obtain suitable fragments or derivatives. For example, the sequence of the particular polypeptide fragment or derivative may be compared with that of similar peptides to determine residues or regions of homology that need to be conserved to maintain activity.

Suitable amino acid substitutions may be determined by replacing one amino acid with another amino acid having similar structural and/or chemical properties, i.e., by making conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Suitable variations may be routinely determined by experimentally making insertions, deletions, or substitutions of amino acids in a polypeptide molecule using recombinant DNA techniques and assaying the resulting recombinant variants for activity.

"Polypeptide" refers to any peptide or protein comprising two or more amino acids joined to each other in a linear chain by peptide bonds. As used herein, the term refers both to short chains, which are also referred to in the art as, e.g., peptides, oligopeptides and oligomers, and to longer chains, which are often referred to in the art as proteins, of which there are many types. The term also refers to various forms of protein, including the pro, pre-pro, and mature forms, as discussed above.

It will be appreciated that polypeptides often contain amino acids other than the 20 amino acids commonly referred to as the 20 naturally occurring amino acids, and that many amino acids, including the terminal amino acids, can be modified in a given polypeptide, either by natural processes, such as processing and other post-translational modifications, and by chemical modification techniques known in the art. Common modifications that occur naturally in polypeptides are described in basic texts and in more detailed monographs, as well as in research literature, and are therefore within the purview of persons of ordinary skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Several common modifications, such as glycosylation, lipid attachment, sulfation, gamma-carboxylation of glutamic acid residues, hydroxylation and ADP-ribosylation, are described in many basic texts, including *PROTEINS—STRUCTURE AND MOLECULAR PROPERTIES*, 2nd ed., T. E. Creighton, W.H. Freeman and Company, New York (1993). Many reviews are also available on this subject, such as those provided by Wold, "Posttranslational Protein Modifications: Perspectives and Prospects," pgs. 1-12 in *POSTTRANSLATIONAL COVALENT MODIFICATION OF PROTEINS*, Johnson (ed.), Academic Press, New York (1983); Seifter et al. (1990), *Meth. Enzymol.*, 182, 626-646; and Rattan et al., "Protein Synthesis: Posttranslational Modifications and Aging" (1992), Ann. N.Y. Acad. Sci., 663, 48-62.

It will be appreciated, as is known and as noted above, that polypeptides are not always entirely linear. For instance, polypeptides can be post-translationally modified, including via natural processing or through human manipulation. Circular, branched and branched-circular polypeptides can be synthesized by non-translation natural processes and by entirely synthetic methods as well. Modifications can occur anywhere in a polypeptide, including the peptide backbone, the amino acid side-chains, and the amino or carboxyl termini. For example, blockage of the amino or carboxyl group or both in a polypeptide by a covalent modification is common in naturally occurring and synthetic polypeptides, and such modifications can be present in polypeptides of the present invention. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus can be deleted. Accordingly, this invention contemplates the use of both the methionine-containing and the methionineless amino terminal variants of the protein.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same post-translational glycosylations as mammalian cells and, for this reason, insect-cell expression systems have been developed to express efficiently mammalian proteins having native patterns of glycosylation, among other things. Similar considerations apply to other modifications. It will be appreciated that the same type of modification can be present in the same or varying degree at several sites in a given polypeptide. Also, a given polypeptide can contain many types of modifications. In general, as used herein, the term "polypeptide" encompasses all such modifications, including those that are present in polypeptides synthesized recombinantly by expressing a polynucleotide in a host cell.

In preferred embodiments, the relaxin-3 chimeric polypeptides are polypeptides in which a relaxin-3 chain B is bonded to a relaxin-3/insulin family member chain A that is not a relaxin-3 chain A. Isolated polynucleotides encoding prepropolypeptides, from which the preferred relaxin-3 chain-B:relaxin/insulin family member chain A chimeric polypeptides are derived, are also provided.

"Polynucleotide" refers to a linear polymer of at least 2 nucleic acid molecules joined together by phosphodiester bonds, and may comprise ribonucleotides or deoxyribonucleotides.

The term "nucleic acid" as used herein refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single- or double-stranded. However, linkages may include any of the linkages known in the art, including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and includes any nucleic acid sequence that is substantially homologous to the both the nucleic acid sequence and its complement.

In preferred embodiments of the polynucleotides, the molecules are isolated. An "isolated" nucleic acid molecule or polynucleotide is one that is substantially separated from nucleic acid molecules or polynucleotides with differing nucleic acid sequences. Embodiments of the isolated nucleic acid molecule of the invention include cDNA and genomic DNA and RNA, preferably of rat origin, more preferably of human origin.

"Genetic variant" or "variant" means a specific genetic variant which is present at a particular genetic locus in at least one individual in a population and that differs from the wild type.

"Stringent hybridization conditions" has the meaning known in the art. An extensive guide to the hybridization of nucleic acids is found in Sambrook et al., Molecular Cloning: A Laboratory Manual, Second Edition, Cold Spring Harbor Laboratory, Cold Spring Harbor, N.Y., and (1989) Tijssen, Techniques in Biochemistry and Molecular Biology-Hybridization with Nucleic Probes, "Overview of principles of hybridization and the strategy of nucleic acid assays" (1993). Stringent hybridization conditions may be suitably selected in view of the particular sequence.

Longer sequences hybridize specifically at higher temperatures. Exemplary stringent conditions include a temperature about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Exemplary stringent conditions further include a salt concentration less than about 1.0 M sodium ion, e.g., about 0.01 to 1.0 M sodium ion concentration (or other salts) at pH 7.0 to 8.3 and a temperature of at least about 30° C. for short probes (e.g., 10 to 50 nucleotides) and at least about 60° C. for long probes (e.g., greater than 50 nucleotides). Stringent conditions may also include the addition of destabilizing agents such as formamide. For selective or specific hybridization, an exemplary positive signal is at least two times background, optionally 10 times background hybridization. Illustrative stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

As known in the art, alternative splicing sites may be found in intronic or exonic sequences of genes, giving rise to variant polypeptide gene products. Through routine experimentation alternative or cryptic splice junction sites may be found within intronic or exonic sequences or relaxin/insulin family genes, yielding a variety of relaxin/insulin family transcripts, and used to ultimately produce other relaxin-3 chimeric polypeptides within the scope of the invention. It is also known that interspecies and inter-individual polymorphic heterogeneity (genetic variation at a particular genetic locus among individuals in a population) in such intronic or exonic alternative or cryptic splice junction sites can exist. Such heterogeneity can be exploited by the artisan to obtain various relaxin-3 chimeric polypeptides with amino acid sequences of varying length that possess the biological activity associated with the relaxin-3 chimeric polypeptides described supra and infra. Such alternative relaxin-3 chimeric polypeptides and polynucleotides that encode pre-propolypeptides from which such alternative relaxin-3 chimeric polypeptides are derived, are therefore within the scope of the present invention.

Additionally, the inventive polynucleotides encoding alternative relaxin-3 chimeric pre-propolypeptides may be synthesized or selected by making use of the redundancy in the genetic code. Various codon substitutions, such as the silent changes that produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the encoded polypeptide, to change characteristics such as affinities for proteins with which the wild-type protein associates, affinities for antibodies, or degradation/turnover rates. Where alteration of a particular function is desired, insertions, deletions or non-conservative alterations can be engineered to produce polypeptides with altered functions but retained biological activity. Such functional alterations can, for example, alter one or more of the biochemical characteristics of the polypeptides of the invention so long as the desired biological activity is maintained. For example, appropriate alterations can be selected so as to generate polypeptides that are better suited for expression, scale up, and the like in the host cells chosen for expression.

The nucleic acid sequences that encode the pre-propolypeptides from which the inventive relaxin-3 chimeric polypeptides are derived also may be cloned using techniques such as those described in the examples below. Any of a variety of procedures known in the art can be used to prepare the nucleic acid molecules of the invention. For example, using cDNA or genomic DNA libraries, or total mRNA from the suitable cells identified above, as a template, and appropriate oligonucleotides as primers, the nucleic acid sequences that encode the polypeptide chains or domains that comprise the inventive relaxin-3 chimeric polypeptides can be amplified according to standard PCR amplification techniques. The nucleic acid sequences so amplified from PCR can be used to construct the inventive polynucleotides that encode the disclosed relaxin-3 chimeric pre-propolypeptides. The so constructed polynucleotides that encode the disclosed pre-propolypeptides can then be cloned into an appropriate vector and characterized by DNA sequence analysis. Primers can be prepared by standard synthetic techniques, e.g., using an automated DNA synthesizer.

Another method to isolate a nucleic acid sequence of the invention is to probe a genomic or cDNA library, or total mRNA with one or more natural or artificially designed probes using procedures available to those skilled in the art. See, e.g., "Current Protocols in Molecular Biology", Ausubel et al. (eds.), Greene Publishing Association and John Wiley Interscience, New York, 1992. Preferred probes will have from 30 to 50 bases. Such probes can be labeled with an analytically detectable reagent to facilitate identification of the probe. Useful reagents include, e.g., radioisotopes, fluorescent dyes, or enzymes capable of catalyzing the formation of a detectable product. The probes enable the ordinarily skilled artisan to isolate complementary copies of genomic DNA, cDNA or RNA polynucleotides encoding relaxin/insulin family members. The probes also enable the ordinarily skilled artisan to isolate complementary copies of genomic DNA, cDNA or RNA polynucleotides encoding GPRC135, such as from mouse as well as human, rat, monkey, cow, and pig, and to isolate complementary copies of genomic DNA, cDNA or RNA polynucleotides encoding GPRC142, such as from mouse as well as human, monkey, cow, and pig.

Another method to prepare nucleic acid sequences is by standard synthetic techniques, e.g., using an automated DNA synthesizer. Construction of genomic DNA libraries, preparation of cDNA libraries, or isolation of total mRNA from the identified source cell can be performed by standard techniques known in the art. These techniques can be found, for example, in Maniatis et al., "Molecular Cloning: A Laboratory Manual," $2^{nd}$ ed. (Cold Spring Harbor Laboratory, Cold Spring Harbor, N.Y., 1989).

Further embodiments provide engineered polynucleotides having any such nucleotide variations that are not known to occur naturally which encode polypeptides having properties that are different than, but still maintain biological activity of the non-variant relaxin-3 chimeric polypeptides. DNA sequences can be altered manually so as to code for a relaxin-3/insulin family member chain A, chain B, or chain C peptide having properties that are different from those of the naturally occurring chain A, chain B, or chain C peptides. Known methods of altering the DNA sequences include site-directed mutagenesis, chimeric substitution, and gene fusions. Site-directed mutagenesis may be used to change one or more DNA residues that can result in a silent mutation, a conservative mutation, or a nonconservative mutation. Chimeric genes may be prepared by swapping chains or domains of similar or different relaxin-3/insulin family member genes to replace such chains or domains in the human relaxin-3/insulin family member gene. Similarly, fusion genes can be prepared that add domains to a relaxin-3/insulin family member gene, such as an affinity tag to facilitate identification and isolation of the gene and protein.

The biological activity of relaxin-3 chimeric polypeptides disclosed herein as well as, e.g., polymorphic variants, interspecies variants, as well as interspecies homologs and alleles, and engineered variants, can be confirmed by examining, e.g., selectivity of binding and stimulating a GPCR135 or a GPCR142, while not binding to or stimulating an LGR7 or an LGR8, of the putative relaxin-3 chimeric polypeptide variant. For example, the biological activity of the relaxin-3/INSL5 chimeric polypeptide having an amino acid sequence of SEQ ID NO:23 can be used as a positive control in comparison to other relaxin-3/chimeric polypeptide variants to confirm conservation of biological activity.

In a preferred embodiment, the relaxin-3 chimeric polypeptide is a biologically active polypeptide having at least 95% sequence identity to the amino acid sequence set forth in SEQ ID NO:23. In an especially preferred embodiment, the relaxin-3 chimeric polypeptide has a sequence as set forth in SEQ ID NO:23.

"Sequence identity or similarity or homology", as known in the art, is the relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

To determine the percent identity or similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position. The percent identity or similarity between the two sequences is a function of the number of identical or similar positions shared by the sequences (i.e., % identity=# of identical positions/total # of positions (e.g., overlapping positions)×100).

Both identity and similarity can be readily calculated. In calculating percent identity, only exact matches are counted. Methods commonly employed to determine identity or similarity between sequences include, e.g., those disclosed in Carillo et al., 1988, *SIAM J. Applied Math.*, 48:1073. Preferred methods to determine identity are designed to give the largest match between the sequences tested. Exemplary methods to determine identity and similarity are also provided in commercial computer programs. A preferred example of a mathematical algorithm utilized for the comparison of two sequences is the algorithm of Karlin et al., 1990, *Proc. Natl. Acad. Sci. USA*, 87:2264-2268, modified as in Karlin et al., 1993, *Proc. Natl. Acad. Sci. USA*, 90:5873-5877. Such an algorithm is incorporated into the NBLAST and XBLAST programs of Altschul et al., 1990, *J. Mol. Biol.*, 215:403-410. To obtain gapped alignments for comparison purposes, Gapped BLAST can be utilized as described in Altschul et al., 1997, *Nucleic Acids Res.*, 25:3389-3402.

Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. See, e.g., http://www.ncbi.nlm.nih.gov. Additionally, the FASTA method (Atschul et al., 1990, *J. Mol. Biol.*, 215:403) can be used. Another preferred example of a mathematical algorithm useful for the comparison of sequences is the algorithm of Myers et al., 1988, *CABIOS*, 4:11-17. Such an algorithm is incorporated into the ALIGN program (version 2.0), which is part of the GCG sequence alignment software package (Devereux et al., 1984, *Nucleic Acids Res.*, 12(1):387).

In various embodiments, the inventive polynucleotides are inserted into expression vectors for introduction of such polynucleotides into host cells for the expression, i.e., production of the encoded mRNA or protein, of the relaxin-3 chimeric pre-propolypeptides encoded by such polynucleotides in such host cells. In certain embodiments, chimeric polypeptides of the invention are produced by recombinant DNA techniques. The expressed relaxin-3 chimeric pre-propolypeptides are processed the corresponding mature forms in vivo, and the resulting recombinant host cells are isolated for various uses in vitro, or serve to modulate various other in vivo activities within such recombinant host cells.

A host cell, which is a cell that contains a DNA molecule either in a vector or integrated into a cell chromosome, can be either a native host cell that contains an endogenous DNA molecule, or a recombinant host cell. Exemplary host cells include bacterial cells, yeast cells, and animal cells. Preferred host cells include mammalian cells, more preferably human cells.

The term "cell" refers to at least one cell or a plurality of cells appropriate for the sensitivity of the detection method. Cells suitable for the present invention may be bacterial, but are preferably eukaryotic, such as yeast, insect, or mammalian. The cell can be a natural host cell for an endogenous GPCR135 or GPCR142, or both GPCR135 and GPCR142, or preferably a recombinant host cell for a GPCR135 or GPCR142, or both GPCR135 and GPCR142, which expresses increased amount of a mammalian GPCR135 or GPCR142, or both GPCR135 and GPCR142, on the cell surface.

A "recombinant host cell" is a cell that has been transformed or transfected by an exogenous DNA sequence. As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term.

A clone is a population of cells derived from a single cell or common ancestor by mitosis. A cell line is a clone of a primary cell that is capable of stable growth in vitro for many generations.

In another aspect, the present invention provides vectors, preferably expression vectors, containing a nucleic acid that is capable of expressing the inventive polynucleotides encoding the disclosed relaxin-3 chimeric pre-propolypeptides. In a preferred embodiment, the preferred expression vector contains a polynucleotide encoding the inventive relaxin-3/INSL5 chimeric pre-propolypeptide.

The term "vector" refers to a nucleic acid molecule capable of transporting another nucleic acid to which it has been linked. One type of vector is a "plasmid," which refers to a circular double-stranded DNA loop into which additional DNA segments can be inserted. Another type of vector is a viral vector wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors—expression vectors—are capable of directing the expression of genes to which they are operably linked. Vectors of utility in recombinant DNA techniques may be in the form of plasmids. Alternatively, other forms of vectors, such as viral vectors (e.g., replication defective retroviruses, adenoviruses and adeno-associated viruses), which serve equivalent functions, may be used.

The recombinant expression vectors of the invention comprise a nucleic acid of the invention in a form suitable for expression of the nucleic acid in a host cell. Thus, the recombinant expression vectors can include one or more regulatory sequences, such as a promoter, selected on the basis of the host cells to be used for expression, operably linked to the nucleic acid sequence to be expressed. When used in reference to a recombinant expression vector, "operably linked" is intended to mean that the nucleotide sequence of interest is linked to the regulatory sequence(s) in a manner allowing for expression of the nucleotide sequence (e.g., in an in vitro transcription/translation system or in a host cell when the vector is introduced into the host cell). It will be appreciated by those of ordinary skill in the art that the design of the expression vector can depend on such factors as the choice of the host cell to be transformed and the level of expression of protein desired as well as the intended use of the vector. The expression vectors of the invention can be introduced into host cells to thereby produce proteins or peptides, including fusion proteins or peptides, encoded by nucleic acids as described herein. One exemplary application of vectors according to the invention is use in therapeutic treatment methods as described below.

"Promoter" means a regulatory sequence of DNA that is involved in the binding of RNA polymerase to initiate transcription of a gene. Promoters are often upstream (i.e., 5' to 3') the transcription initiation site of the gene. A "gene" is a segment of DNA involved in producing a peptide, polypeptide, or protein, including the coding region, non-coding regions preceding ("5'UTR") and following ("3'UTR") coding region, as well as intervening non-coding sequences ("introns") between individual coding segments ("exons").

"Coding" refers to the specification of particular amino acids or termination signals in three-base triplets ("codons") of DNA or mRNA.

The recombinant expression vectors of the invention can be designed for expression of a polypeptide of the invention in prokaryotic (e.g., *Escherichia coli* (*E. coli*)) or eukaryotic cells (e.g., insect cells (using baculovirus expression vectors), yeast cells or mammalian cells). Suitable host cells may be routinely determined. Alternatively, the recombinant expression vector can be transcribed and translated in vitro, for example using T7 promoter regulatory sequences and T7 polymerase.

Expression of proteins in prokaryotes may be carried out in *E. coli* with vectors containing constitutive or inducible promoters directing the expression of either fusion or non-fusion proteins. Fusion vectors add a number of amino acids to a protein, usually to the amino terminus of the recombinant protein. Such fusion vectors typically are used for one or more of the following purposes: to increase expression of recombinant protein; to increase the solubility of the recombinant protein; to aid in the purification of the recombinant protein by acting as a ligand in affinity purification; and to facilitate detection of the recombinant protein by serving as a marker. Often in fusion expression vectors, a proteolytic cleavage site is introduced at the junction of the fusion moiety and the recombinant protein to enable separation of the recombinant protein from the fusion moiety subsequent to purification of the fusion protein. Such enzymes and their cognate recognition sequences include Factor Xa, thrombin and enterokinase. Exemplary fusion expression vectors include pGEX (Pharmacia Biotech Inc; Smith et al., 1988, *Gene,* 67:31-40), pMAL (New England Biolabs, Beverly, Mass.), pRIT5 (Pharmacia, Piscataway, N.J.), or pQE (Qiagen), which fuse glutathione S-transferase (GST), maltose binding protein, protein A, or poly-His, respectively, to the target recombinant protein.

Examples of suitable inducible non-fusion *E. coli* expression vectors include pTrc (Amann et al., 1988, *Gene,* 69:301-315) and pETIId (Studier et al., "Gene Expression Technology: Methods in Enzymology 185," Academic Press, San Diego, Calif., 1990, 60-89). One strategy to maximize recombinant protein expression in *E. coli* is to express the protein in a host bacterium with an impaired capacity to proteolytically cleave the recombinant protein. Another strategy is to alter the nucleic acid sequence of the nucleic acid to be inserted into an expression vector so that the individual codons for each amino acid are those preferentially utilized in *E. coli*. Such alteration of nucleic acid sequences of the invention can be carried out by standard DNA synthesis techniques.

In another preferred embodiment, the expression vector is a yeast expression vector. Examples of vectors for expression in yeast *S. cerivisae* include pYepSec1 (Baldari et al., 1987, *EMBO J,* 6:229-234), pMFa (Kurjan et al., 1982, *Cell,* 30:933-943), pJRY88 (Schultz et al. 1987, *Gene,* 54:113-123), pYES2 (Invitrogen Corporation, San Diego, Calif.), and pPicZ or Pichia (Invitrogen Corp, San Diego, Calif.).

Alternatively, the expression vector is a baculovirus expression vector. Baculovirus vectors available for expression of proteins in cultured insect cells include, e.g., the pAc series (Smith et al., 1983, *Mol. Cell. Biol.,* 3:2156-2165) and the pVL series (Lucklow et al., 1989, *Virology,* 170:31-39). Commercially available insect cell expression vectors useful for recombinant expression include pBlueBacII (Invitrogen).

In yet another preferred embodiment, the expression vector is a mammalian expression vector. When used in mammalian cells, the expression vector's control functions are often provided by viral regulatory elements. For example, commonly used promoters are derived from polyoma, Adenovirus 2, cytomegalovirus and Simian Virus 40. Examples of mammalian expression vectors include, e.g., pCDM8 (Seed, 1987, *Nature,* 329:840) and pMT2PC (Kaufinan et al., 1987, *EMBO J,* 6:187-195). Commercially available mammalian expression vectors which can be suitable for recombinant protease COX-3 expression include, for example, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Examples of suitable tissue-specific promoters include the albumin promoter (liver-specific; Pinkert et al., 1987, *Genes Dev.,* 1:268-277), lymphoid-specific promoters (Calame et al., 1988, *Adv. Immunol.,* 43:235-275), in particular promoters of T cell receptors (Winoto et al., 1989, *EMBO J,* 8:729-733) and immunoglobulins (BaneiJi et al., 1983, *Cell,* 33:729-740; Queen et al., 1983, *Cell,* 33:741-748), neuron-specific promoters (e.g., the neurofilament promoter; Byme et al., 1989, *Proc. Natl. Acad. Sci. USA,* 86:5473-5477), pancreas-specific promoters (Edlund et al., 1985, *Science,* 230:912-916), and mammary gland-specific promoters (e.g., milk whey promoter; U.S. Pat. No. 4,873,316 and European Patent Publication No. 264,166). Developmentally regulated promoters also include, for example, the marine hox promoters (Kessel et al., 1990, *Science,* 249:374-379) and the beta-fetoprotein promoter (Campes et al., 1989, *Genes Dev.,* 3:537-546).

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding the polypeptide under the direction of the polyhedrin promoter or other strong baculovirus promoters.

The elements that can be included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences may be chosen such that they do not interfere with the replication of the DNA in eukaryotic cells, if necessary or desired.

A recombinant vector may be prepared comprising a DNA molecule of the invention cloned into the vector in an antisense orientation. That is, the DNA molecule is operably linked to a regulatory sequence in a manner that allows for expression (by transcription of the DNA molecule) of an RNA molecule that is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell-type specific expression of antisense RNA. The antisense expression vector can be in the form of a recombinant plasmid, phagemid or attenuated virus in which antisense nucleic acids are produced under the control of a high-efficiency regulatory region, the activity of which can be determined by the cell type into which the vector is introduced. For a discussion of the regulation of gene expression using antisense genes see Weintraub et al. ("Reviews—Trends in Genetics," Vol. 1(1) 1986).

A recombinant vector system may also be prepared to direct the synthesis of small interfering RNAs (siRNAs) in mammalian cells. Many organisms possess mechanisms to silence any gene expression when double-stranded RNA (dsRNA) corresponding to the gene is present in the cell through a process known as RNA interference. The technique of using dsRNA to reduce the activity of a specific gene was first developed using the worm *C. elegans* and has been termed RNA interference or RNAi (Fire et al., 1998, *Nature*, 391: 806-811). RNAi has since been found to be useful in many organisms, and recently has been extended to mammalian cells in culture (see review by Moss, 2001, *Curr Biol*, 11:R772-R775). An important advance was made when RNAi was shown to involve the generation of small RNAs of 21-25 nucleotides (Hammond et al., 2000, *Nature*, 404:293-296; Zamore et al., 2000, *Cell*, 101:25-33). These small interfering RNAs, or siRNAs, may initially be derived from a larger dsRNA that begins the process, and are complementary to the target RNA that is eventually degraded. The siRNAs are themselves double-stranded with short overhangs at each end; they act as guide RNAs, directing a single cleavage of the target in the region of complementarity (Elbashir et al., 2001, *Genes Dev.*, 15:188-200; Zamore et al., 2000, *Cell*, 101: 25-33).

An siRNA comprising nucleotides that are complementary to mouse GPCR135 or GPCR142 may be produced in vitro, for example, using a method described in WIPO Publication No. WO 01/75164, or can be produced in vivo from a mammalian cell using a stable expression system. An exemplary vector system that directs the synthesis of siRNAs in mammalian cells is the pSUPER (Brummelkamp et al., 2002, *Science*, 296: 550-553).

Exemplary vectors of the present invention also include specifically designed vectors that allow the shuttling of DNA between hosts such as bacteria-yeast or bacteria-animal cells or bacteria-fungal cells or bacteria-invertebrate cells. Numerous cloning vectors are known to those skilled in the art and the selection of an appropriate cloning vector is within the purview of the artisan. For other suitable expression systems for both prokaryotic and eukaryotic cells see, e.g., chapters 16 and 17 of Maniatis et al., supra.

Recombinant host cells may be prepared by introducing a recombinant vector of the invention. Cell lines derived from mammalian species which can be suitable for transfection and which are commercially available include, e.g., CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), *Drosophila* or murine L-cells, and HEK-293 (ATCC CRL1573), and monkey kidney cells.

Vector DNA can be introduced into prokaryotic or eukaryotic cells via conventional transformation or transfection techniques. As used herein, the term "transformation" or "transfection" refers to a process by which cells take up foreign DNA and may or may not integrate that foreign DNA into their chromosome. Any of the known procedures suitable for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the Gene Gun), or any other known methods for introducing cloned genomic DNA, cDNA, synthetic DNA or other foreign genetic material into a host cell (see, e.g., Sambrook et al., supra). The selected particular genetic engineering procedure used should be capable of successfully introducing at least one gene into the host cell capable of expressing the mRNA, cDNA, or gene.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) may be introduced into the host cells along with the gene of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous nucleic acid within a cell, cell line or microorganism can be modified by inserting a heterologous regulatory element into the genome of a cell, a stable cell line, or a cloned microorganism, such that the inserted regulatory element is operatively linked with the endogenous gene and controls, modulates or activates the endogenous gene. A heterologous regulatory element can be inserted into a stable cell line or cloned microorganism such that it is operatively linked with and activates expression of endogenous genes, using techniques such as targeted homologous recombination, e.g., as described in U.S. Pat. No. 5,272,071 and WIPO Publication No. WO 91/06667.

Polypeptides of the invention can be recombinantly expressed by cloning DNA molecules of the invention into an expression vector described above, introducing such a vector into prokaryotic or eukaryotic host cells as described herein, and growing the host cell under conditions suitable for production of recombinant protein.

The expression vector-containing cells may be clonally propagated and individually analyzed to determine whether they produce the polypeptide of the invention. Identification of the animal relaxin-3 chimeric polypeptide-expressing host cell clones can be done by several means, including immunological reactivity with anti-animal relaxin-3 chimeric polypeptide antibodies, and the presence of host cell-associated relaxin-3 chimeric polypeptide, such as GPCR135 or GPCR142 binding or stimulation. The selection of the appropriate growth conditions and recovery methods are within the skill of the art. Techniques for recombinantly expressing a polypeptide are described in, e.g., Maniatis et al., supra.

Polypeptides of the invention can also be produced using an in vitro translation and/or transcription system available in the art. For example, synthetic relaxin-3 chimeric pre-propolypeptide mRNA or relaxin-3 chimeric pre-propolypeptide mRNA isolated from transformed or transfected cells can be efficiently translated in various cell-free systems, including wheat germ extracts and reticulocyte extracts. Alternatively, the coding sequence of the inventive relaxin-3 chimeric pre-propolypeptide cDNA can be cloned under the control of a T7 promoter. Then, using this construct as the template, the protein can be produced in an in vitro transcription and translation system, for example using a TNT T7 coupled Reticulocyte Lysate System such as that commercially available from Promega (Madison, Wis.).

In a general aspect, the invention is directed to receptor-ligand complexes comprising a relaxin-3 chimeric polypeptide component and a GPCR135 or GPCR142 receptor component. In some embodiments of the invention, ligand-and-receptor complexes are detected, identified, formed, or isolated.

The components of the complex (e.g., relaxin-3 chimeric polypeptides along with GPCR135 and/or GPCR142 polypeptides) can be purified by methods known to those skilled in the art. For example, they can be purified from cell lysates and extracts from natural or recombinant host cells, by various combinations or individual application of salt fractionation, ion exchange chromatography, size exclusion chromatography, hydroxylapatite adsorption chromatography and hydrophobic interaction chromatography, lectin chromatography, HPLC, and FPLC, and antibody/ligand affinity chromatography. Further alternatively, a polypeptide of the invention can be synthesized chemically using standard peptide synthesis techniques, and purified as described supra.

The isolated and purified relaxin-3 chimeric polypeptides of the invention may be used in assay methods for selectively detecting, identifying, or stimulating or GPCR135 or GPCR142 (i.e., while not detecting, identifying, or stimulating LGR7 or LGR8) in test biological samples, in methods for identifying compounds having GPCR135 or GPCR142 modulating activities, and in treating medical conditions mediated by modulation of GPCR135 or GPCR142.

In certain embodiments of such methods, naturally occurring GPCR135 or GPCR142-containing biological samples are isolated, e.g., from mammalian tissue such as brain, spleen, placenta, lung, liver, kidney, pancreas, prostate, testis, ovary, small intestine, colon, lymph node, and tonsils, or any other source of a GPCR135 or GPCR142 homolog. Bodily fluids such as blood, blood plasma, serum, seminal fluid, urine, or any other mammalian bodily fluid can also serve as sources of natural GPCR135 or GPCR142 polypeptides. Cultured mammalian cell lines are still further exemplary sources of natural GPCR135- or GPCR142-containing biological samples.

In especially preferred embodiments, the GPCR135 or GPCR142-containing biological sample is derived from mammalian brain tissue, preferably rat brain tissue, and more preferably from human brain tissue. In still other preferred embodiments, the GPCR135 or GPCR142-containing biological sample is derived, from human cell lines, such as G292 (ATCC #CRL-1423), HeLa (ATCC #CCL-2), Jurkat (ATCC #TIB-152), and THP-1 (ATCC #TIB-20). In still further preferred embodiments, polypeptides are derived from monocytes substantially purified from peripheral blood and from monocyte-derived dendritic cells. Methods of purification of monocytes substantially purified from peripheral blood are known in the art; for example, such cells may be adsorbed onto CD14 microbeads and subsequently separated on an Auto Macs (Miltenyi Biotech). An exemplary method to derive dendritic cells from monocytes is to culture the monocytes in the presence of GM-CSF and IL-4 in endotoxin-free media and reagents.

A "ligand component" refers to a relaxin-3 chimeric polypeptide in accordance with the invention, such as those described above. In a preferred embodiment, the ligand component is composed of a relaxin-3 chain B that is originated from a human, a mouse, or a rat, that is bonded via a disulfide linkage to a relaxin/insulin family member chain A that is originated from a human. Preferably, the ligand component has been recombinantly expressed. Preferred ligand components correspond to the relaxin-3 chimeric polypeptides identified in the accompanying Sequence Listing.

In other preferred embodiments of the ligand-and-receptor complexes of the invention, the ligand component is labeled with a detectable agent, such as a radioisotope or a fluorescent molecule. The labeling technique is selected based on the type of labeling agent employed, and is within the purview of those ordinarily skilled in the art. For instance, labeling can be accomplished by replacing one of the atoms of a ligand molecule with a corresponding radioactive isotope. A hydrogen atom could be replaced with tritium, $^3H$; a carbon atom can be replaced with carbon-14, $^{14}C$; or a strontium atom can be replaced with strontium-38, $^{38}Sr$. In another exemplary labeling process, rather than replacing any atoms of the ligand with a radioactive isotope, an isotope can be added to the ligand molecule. Such radioactive isotopes include, for example, iodine-125, $^{125}I$, and iron-59, $^{59}Fe$. In yet another exemplary labeling process, labeling can be carried out by using an appropriate radiolabeled precursor, such as methionine-35 ($^{35}S$) or phosphate-33 ($^{33}P$, for protein phosphorylation), during the synthesis of the peptide either in vivo or in vitro. Preferably, the ligand component of this invention is labeled with iodine-125, $^{125}I$.

The receptor component of the complex is preferably a mammalian GPCR135 or a mammalian GPCR142. More preferably, the receptor of the complex is a human GPCR135 or a human GPCR142.

In a certain preferred embodiment, the GPCR135 or GPCR 142, or both GPCR135 and GPCR 142, is expressed on the cell surface of a host cell, preferably a recombinant host cell. In another preferred embodiment, the GPCR135 or GPCR142, or both GPCR135 and GPCR 142, is associated with isolated cell membranes from a host cell, preferably from a recombinant host cell. In yet another preferred embodiment, the receptor component of the complex is a fragment of the GPCR135 or a fragment of the GPCR142 capable of binding to an inventive relaxin-3 chimeric polypeptide ligand. Any suitable methods for constituting a ligand component and receptor complex available to artisans may be used to form such a complex. For example, such a method generally comprises mixing a sample comprising the ligand component with a sample comprising the receptor.

The sample comprising the ligand component can be tissue or cell extract containing the ligand component, or purified ligand component. This sample can be prepared from a natural source of the ligand component, e.g., an endogenous host cell or tissue for the ligand component of warm-blooded animals inclusive of human. Preferably, the sample comprising the ligand component is prepared from a recombinant host cell that expresses increased amount of the ligand component. A recombinant host cell for the ligand component may be constructed by introducing into the cell a DNA molecule capable of expressing the functional ligand component.

In the production from the tissues or cells of human or other warm-blooded animals, the ligand component chimerae can be purified and isolated by a process comprising homogenizing the tissue or cells of human or other warm-blooded animal, extracting the homogenate with an acid or another suitable extracting agent, and isolating the ligand component polypeptide from the extract.

Any of a number of suitable procedures can be employed when the inventive relaxin-3 chimeric polypeptides or a GPCR135 or GPCR142 are being purified. For example, proteins having established molecular adhesion properties can be reversibly fused to the polypeptides. With the appropriate ligand, the polypeptide can be selectively adsorbed to a purification column and then freed from the column in a relatively pure form. The fused protein is then removed by enzymatic activity. The polypeptides can also be purified using immunoaffinity columns.

Recombinant proteins may be expressed by transformed bacteria or eukaryotic cells in large amounts, preferably after promoter induction; but expression can be constitutive. Promoter induction with IPTG is one example of an inducible promoter system. Cells may be grown according to standard procedures in the art. Fresh or frozen cells may be used for isolation of protein.

Proteins expressed in bacteria may form insoluble aggregates (inclusion bodies). Several protocols described in the art are suitable for purification of relaxin-3 chimeric polypeptide-, GPCR135-, or GPCR142-containing inclusion bodies. For example, purification of inclusion bodies may involve the extraction, separation and/or purification of inclusion bodies by disruption of bacterial cells, e.g., by incubation in a buffer of 50 mM TRIS/HCL pH 7.5, 50 mM NaCl, 5 mM MgCl2, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria will be apparent to those of ordinary skill in the art (see, e.g., Sambrook et al., supra; Ausubel et al., supra).

If necessary or desired, the inclusion bodies may be solubilized, and the lysed cell suspension centrifuged to remove unwanted insoluble matter. Proteins that formed the inclusion bodies may be renatured by dilution or dialysis with a compatible buffer. Suitable solvents include urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known in the art. The desired polypeptides are separated from other bacterial proteins by standard separation techniques, e.g., with Ni-NTA agarose resin.

Alternatively, it is possible to purify polypeptides from bacteria periplasm. After lysis of the bacteria, when a protein is exported into the periplasm of the bacteria, the periplasmic fraction of the bacteria can be isolated by cold osmotic shock or another method known in the art. To isolate recombinant proteins from the periplasm, the bacterial cells may be centrifuged to form a pellet. The pellet may be resuspended in a buffer containing 20% sucrose. To lyse the cells, the bacteria may be centrifuged and the pellet resuspended in ice-cold 5 mM $MgSO_4$ and kept in an ice bath for approximately 10 minutes. The cell suspension may be centrifuged and the supernatant decanted and saved. The recombinant proteins present in the supernatant can be separated from the host proteins by standard separation techniques known in the art.

As an initial step, e.g., if a protein mixture is complex, an initial salt fractionation can be used to separate many of the unwanted host cell proteins (or proteins derived from the cell culture media) from the recombinant protein of interest. An exemplary salt is ammonium sulfate, which precipitates proteins by effectively reducing the amount of water in the protein mixture. Proteins then precipitate on the basis of their solubility. The more hydrophobic a protein is, the more likely it is to precipitate at lower ammonium sulfate concentrations.

An exemplary isolation protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed to achieve the desired purity, e.g., through dialysis or diafiltration. Other known methods that rely on solubility of proteins, such as cold ethanol precipitation, can be used to fractionate complex protein mixtures.

In other examples, the molecular weight of the inventive relaxin-3 chimeric polypeptide, or a GPCR135 or a GPCR142, can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut-off greater than the molecular weight of the protein of interest. The recombinant protein will pass through the membrane into the filtrate. The filtrate can then be chromatographed.

The inventive chimeric polypeptides can also be separated from other proteins on the basis of net surface charge, hydrophobicity, and affinity for heterologous molecules. In addition, antibodies raised against proteins can be conjugated to column matrices and the proteins immunopurified. All of these methods are known in the art. It will be apparent to those of ordinary skill in the art that chromatographic techniques can be performed at any suitable scale and using equipment from many different manufacturers (e.g., Pharmacia Biotech).

The invention also permits the identification of antibodies that specifically bind to the relaxin-3 chimeric polypeptides. Such relaxin-3 chimeric polypeptide-specific antibodies have numerous applications, including for the modulation of relaxin-3 chimeric polypeptide activity and for immunoassays to detect the relaxin-3 chimeric polypeptides. Immunoassays can be used to qualitatively or quantitatively analyze relaxin-3 chimeric polypeptides. A general overview of such technology can be found in Harlow & Lane, ANTIBODIES: A LABORATORY MANUAL (1988).

Methods of producing polyclonal and monoclonal antibodies that react specifically with relaxin-3 chimeric polypeptide polypeptides are known in the art (see, e.g., Coligan, CURRENT PROTOCOLS IN IMMUNOLOGY (1991); Harlow & Lane, supra; Goding, MONOCLONAL ANTIBODIES: PRINCIPLES AND PRACTICE (2d ed. 1986); and Kohler & Milstein, 1975, Nature 256:495-497). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989, Science, 246:1275-1281; Ward et al., 1989, Nature, 1989, 341:544-546).

A number of relaxin-3 chimeric polypeptide-comprising immunogens may be used to produce antibodies specifically reactive with a relaxin-3 chimeric polypeptide. For example, a relaxin-3 chimeric polypeptide, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known in the art. In one exemplary method, an inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the polypeptide. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques described in the art. To illustrate briefly, spleen cells from an animal immunized with a desired antigen may be immortalized, e.g., by fusion with a myeloma cell (see Kohler & Milstein, *Eur. J Immunol.*, 1976, 6:511-519). Alternative methods of immortalization include transformation with Epstein Barr Virus, oncogenes, or retroviruses. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., 1989, *Science*, 246: 1275-1281.

Monoclonal antibodies and polyclonal sera may be collected and titered against the immunogen protein in an immunoassay, for example, a solid phase immunoassay with the immunogen immobilized on a solid support. To illustrate, polyclonal antisera with a titer of $10^4$ or greater are selected and tested for their cross-reactivity against unrelated proteins, or even related proteins from other organisms, using a competitive binding immunoassay. Specific polyclonal antisera and monoclonal antibodies may bind with a Kd of 1 µM, 0.1 µM or 0.01 µM or better.

Using anti-relaxin-3 chimeric polypeptide antibodies, individual relaxin-3 chimeric polypeptides can be detected by a variety of immunoassay methods. For a review of immunological and immunoassay procedures, see BASIC AND CLINICAL IMMUNOLOGY (Stites & Terr eds., 7th ed. 1991). Moreover, immunoassays can be performed in any of several configurations, which are reviewed extensively in ENZYME IMMUNOASSAY (Maggio, ed., 1980); and Harlow & Lane, supra.

Biologically active relaxin-3 chimeric polypeptides can be detected and/or quantified using any of a number of known immunological binding assays (see, e.g., U.S. Pat. Nos. 4,366,241; 4,376,110; 4,517,288; and 4,837,168). For a review of the general immunoassays, see also METHODS IN CELL BIOLOGY: ANTIBODIES IN CELL BIOLOGY, volume 37 (Asai, ed. 1993); BASIC AND CLINICAL IMMUNOLOGY (Stites & Terr, eds., 7th ed. 1991). Immunological binding assays (or immunoassays) generally use an antibody that specifically binds to a protein or antigen of choice (in this case a relaxin-3 chimeric polypeptide or an antigenic subsequence thereof). The antibody may be produced by any suitable means known in the art.

Immunoassays also may employ a labeling agent to specifically bind to and label the complex formed by the antibody and antigen. The labeling agent may itself be one of the moieties comprising the antibody/antigen complex. Thus, the labeling agent may be a labeled relaxin-3 chimeric polypeptide or a labeled anti-relaxin-3 chimeric polypeptide antibody. Alternatively, the labeling agent may be a third moiety, such a secondary antibody, that specifically binds to the antibody/relaxin-3 chimeric polypeptide complex (a secondary antibody is preferably specific to antibodies of the species from which the first antibody is derived). Other proteins capable of specifically binding immunoglobulin constant regions, such as protein A or protein G, may be used as the label agent. These proteins exhibit a strong nonimmunogenic reactivity with immunoglobulin constant regions from a variety of species (see, e.g., Kronval et al., 1973, *J. Immunol.*, 111:1401-1406; Akerstrom et al., 1985, *J. Immunol.*, 135: 2589-2542). The labeling agent can be modified with a detectable moiety, such as biotin, to which another molecule can specifically bind, such as streptavidin. A variety of detectable moieties are known in the art.

Throughout the assays, incubation and/or washing steps may be appropriate after each combination of reagents. Incubation steps can vary from about 5 seconds to several hours, optionally from about 5 minutes to about 24 hours. However, the incubation time will depend upon the assay format, antigen, volume of solution, concentrations, and the like. The assays may be carried out at ambient temperature, although they can be conducted over a range of temperatures, such as 10° C. to 40° C.

Immunoassays for detecting a relaxin-3 chimeric polypeptide in a sample may be either competitive or noncompetitive. Noncompetitive immunoassays are assays in which the amount of antigen is directly measured. In one preferred sandwich assay, for example, the anti-relaxin-3 chimeric polypeptide antibodies can be bound directly to a solid substrate on which they are immobilized. These immobilized antibodies then capture the relaxin-3 chimeric polypeptide present in the test sample. The relaxin-3 chimeric polypeptide thus immobilized is then bound by a labeling agent, such as a second relaxin-3 chimeric polypeptide antibody bearing a label. Alternatively, the second antibody may lack a label, but it may, in turn, be bound by a labeled third antibody specific to antibodies of the species from which the second antibody is derived. The second or third antibody is often modified with a detectable moiety, such as biotin, to which another molecule specifically binds, e.g., streptavidin, to provide a detectable moiety.

In competitive assays, the amount of relaxin-3 chimeric polypeptide present in the sample may be measured indirectly by measuring the amount of a known, added (exogenous) relaxin-3 chimeric polypeptide displaced (competed away) from an anti-relaxin-3 chimeric polypeptide antibody by the unknown relaxin-3 chimeric polypeptide present in a sample. In one exemplary competitive assay, a known amount of relaxin-3 chimeric polypeptide is added to a sample and the sample is then contacted with an antibody that specifically binds to the relaxin-3 chimeric polypeptide. The amount of exogenous relaxin-3 chimeric polypeptide bound to the antibody is inversely proportional to the concentration of relaxin-3 chimeric polypeptide present in the sample. In an exemplary embodiment, the antibody is immobilized on a solid substrate. The amount of relaxin-3 chimeric polypeptide bound to the antibody may be determined either by measuring the amount of relaxin-3 chimeric polypeptide present in an relaxin-3 chimeric polypeptide/antibody complex, or alternatively by measuring the amount of remaining uncomplexed protein. The amount of relaxin-3 chimeric polypeptide may be detected by providing a labeled relaxin-3 chimeric polypeptide molecule.

A hapten inhibition assay is another illustrative competitive assay. In this assay the known relaxin-3 chimeric polypeptide is immobilized on a solid substrate. A known amount of anti relaxin-3 chimeric polypeptide antibody is added to the sample, and the sample is then contacted with the immobilized relaxin-3 chimeric polypeptide. The amount of anti relaxin-3 chimeric polypeptide antibody bound to the known immobilized relaxin3 chimeric polypeptide is inversely proportional to the amount of relaxin-3 chimeric polypeptide present in the sample. Again, the amount of immobilized antibody may be determined by detecting either the immobilized fraction of antibody or the fraction of the antibody that remains in solution. Detection may be direct where the antibody is labeled or indirect by the subsequent addition of a labeled moiety that specifically binds to the antibody as described above.

Nucleic acid assays may also be used to detect for the presence of DNA and RNA for a relaxin-3 chimeric polypeptide polynucleotide, or GPCR135 or GPCR142, in a sample. Exemplary embodiments include suitable techniques known in the art such as Southern analysis, Northern analysis, dot blots, RNase protection, S 1 analysis, amplification techniques such as PCR and LCR, RTPCR, and in situ hybridization. In in situ hybridization, the target nucleic acid is liberated from its cellular surroundings in such a way as to be available for hybridization within the cell while preserving the cellular morphology for subsequent interpretation and analysis. See also, Singer et al., 1986, *Biotechniques*, 4:230-250; Haase et al., 1984, *Methods in Virology*, 7:189-226; and NUCLEIC ACID HYBRIDIZATION: A PRACTICAL APPROACH (Hames et al., eds. 1987).

As mentioned above, the chimeric ligand component in the present invention can also be produced by known procedures for peptide synthesis. The methods for peptide synthesis may be selected from suitable solid-phase synthesis and liquid-phase synthesis techniques. For example, the desired peptide can be produced by condensing a partial peptide or amino acid capable of constituting the protein with the residual part thereof and, when the product has a protective group, removing the protective group. Methods for condensation and deprotection during peptide synthesis are described in literature, for example, in: Bodanszky and Ondetti, "Peptide Synthesis," Interscience Publishers, New York, 1966; Schroeder and Luebke, "The Peptide," Academic Press, New York, 1965; Izumiya et al., "Fundamentals and Experiments in Peptide Synthesis," Maruzen, 1975; Yajima and Sakakibara, "Biochemical Experiment Series 1, Protein Chemistry IV," 205, 1977; and Yajima (ed.), "Development of Drugs-Continued, 14, Peptide Synthesis," Hirokawa Shoten.

After the peptide synthesis reaction, the protein product can be purified and isolated by a suitable combination of conventional purification techniques, such as solvent extraction, column chromatography, liquid chromatography, and recrystallization. Where the protein isolated is in a free form, it can be converted to a suitable salt by a known method. Conversely, where the isolated product is a salt, it can be converted to the free peptide by a suitable method selected from those known in the art.

The amide of a polypeptide can be obtained by using a resin for peptide synthesis that is suited for amidation. Exemplary resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl-acetamidomethyl resin, polyacrylamide resin, 4-(2,4'-dimethoxyphenylhydroxymethyl)phenoxy resin, and 4-(2',4'-dimethoxyphenyl-Fmoc aminoethyl)phenoxy resin. Using such a resin, amino acids whose □-amino groups and functional side-chain groups (R groups) have been suitably protected are condensed on the resin according to the sequence of the objective peptide by various condensation techniques that are known to those skilled in the art. At the end of the series of reactions, the peptide or the protected peptide is separated from the resin and the protective groups are removed to obtain the objective polypeptide.

The sample comprising the GPRC135 receptor, the GPCR142 receptor, or both receptors can comprise intact host cells with the receptor(s) expressed on the cell-surface, isolated cell membranes from host cells of the receptor(s), or a purified fragment of the receptor(s) that is capable of binding to the ligand. An endogenous host cell for the GPCR135 receptor or the GPCR142 receptor can also be used. In certain preferred embodiments, an endogenous host cell comprising a GPCR135, a GPCR142, or both a GPCR135 and a GPCR142 is used.

It is known that a GPCR binds to its endogenous ligand sometimes with its extracellular domain. Such a binding domain can be identified by various methods known to those skilled in the art, such as sequence analyses, protein-protein interaction analyses, protein structural analyses, or a combination of these methods. For example, the ligand binding domain in metabotropic glutamate receptors has been identified as a Venus flytrap module (VFTM) in its extracellular domain (O'Hara et al., 1993, *Neuron*, 11(1):41-52; David et al., 1999, *J. Biol. Chem.*, 274:33488-33495). In a preferred embodiment, the ligand-component binding domain of either GPCR135 or GPCR142 can be first identified using the above methods, and such a ligand-component binding domain can be recombinantly expressed, purified and used in forming a complex of the invention.

In certain embodiments, the inventive relaxin-3 chimeric polypeptides are recombinantly produced, e.g., as secreted proteins composed of two chains (A-chain and B-chain) of polypeptides linked by disulfide bridges, where proteases are involved in the production of mature chimeric polypeptides from their immature pre-propolypeptide precursors. Signal sequence peptidase cleaves off the signal sequence from the pre-propolypeptide, resulting in a relaxin-3 chimeric propolypeptide. The relaxin-3 chimeric propolypeptide is subsequently cleaved into chains A, B, and C by pro-hormone convertases. The so-cleaved A-chain and B-chain for a given chimeric polypeptide are bonded by the formation of disulfide linkages to form the mature relaxin-3 chimeric polypeptide; the C-chain is removed and is not a portion of the mature relaxin-3 chimeric polypeptide. Because pro-hormone convertases are only selectively expressed in certain cell types where hormones are secreted, such as some neuron cells or endocrine cells, the relaxin-3 chimeric propeptide is often not processed to an optimal efficiency when it is recombinantly expressed from another cell type, such as a COS7.

A "linkage" or "linked" refers to a bond or connective force by which two or more chemical entities, such as polypeptides or polynucleotides, are joined or otherwise associated, such as via the formation of one or a plurality of covalent bonds, ionic bonds, electrostatic bonds, hydrogen bonds, London dispersion forces, Van der Waals interactions, or hydrophobic interactions. Preferably, the linkages employed in preparing the inventive relaxin-3 chimeric polypeptides are effected by the formation of covalent bonds.

"Prohormone convertase (PC)" refers to a family of $Ca^{2+}$-dependent serine proteases, all of which possess homology to the bacterial endoproteases subtilisin (bacteria) and yeast kexin. This family, also known as furin/paired basic amino-acid-cleaving enzyme (PACE), includes, e.g., PC1/PC3, PC2, PC4, PACE4, PC5/PC6, and PC7/PC8/lymphoma proprotein convertase, and SKI-1. They share a degree of amino-acid identity of 50-75% within their catalytic domains (for a review on PCs, see Seidah et al., 1999, *Brain Res,* 848(1-2): 45-62).

The relaxin-3 chimeric polypeptide may be produced from a recombinant host cell by steps comprising: constructing a DNA molecule capable of encoding a relaxin-3 chimeric pre-propolypeptide, comprising a polynucleotide encoding a relaxin-3 B-chain joined by a first peptide linkage to a relaxin-3 C-chain, the C-chain further joined by a second peptide linkage to a relaxin/insulin family member A-chain, and a protease cleavage site inserted at at least one location selected from the group consisting of the second peptide linkage between the A-chain and C-chain and the first peptide linkage between the C-chain and the B-chain of the relaxin-3 pre-propolypeptide; constructing a vector capable of expressing the relaxin-3 pre-propolypeptide; constructing another vector capable of expressing a protease that can cleave the relaxin-3 pre-propolypeptide at the inserted protease cleavage site(s); introducing both the vectors into a host cell; and growing the host cell under conditions suitable for the expression of both the modified relaxin-3 pre-propolypeptide and the protease, so that the protease will cleave a peptide linkage at the inserted protease cleavage site(s) on the relaxin-3 chimeric pre-propolypeptide yielding a mature relaxin-3 chimeric polypeptide.

Sequence analyses suggested that furin, a member of the pro-hormone convertases, cleaves the peptide linkage between chains C and B on the native relaxin-3 pre-propolypeptide, and another unidentified protease cleaves the peptide linkage between chains A and C on the native propeptide. A furin cleavage site, with the amino acid sequence of arg-gly-arg-arg (RGRR), may be inserted at the peptide junction of chains A and C. An expression vector for this mutant relaxin-3 chimeric prepropolypeptide and another expression vector for furin are co-transfected into a host cell. Under suitable growth conditions, the relaxin-3 chimeric pre-propolypeptide is almost completely processed into mature polypeptides, A, B, and C. Instead of furin, other proteases can also be used. Identical protease cleavage sites can be inserted between chains A and C, and chains C and B, of the chimeric pre-propolypeptide. Examples of proteases that can be used include, e.g., a pro-hormone convertase, such as furin, PC1, and PC2 (Hosaka et. al., 1991, *J. Biol. Chem.,* 266:12127-12130; Benjannet et. al., 1991, *Proc. Natl. Acad. Sci. USA,* 88:3564-3568; Thomas et. al., 1991, *Proc. Natl. Acad. Sci. USA,* 88:5297-5301).

In preferred embodiments, a tag, such as a HA, poly His, or FLAG, can be added either to the inventive modified relaxin-3 chimeric pre-propolypeptides. The term "tag" refers to an amino acid sequence or a nucleotide sequence encoding an amino acid sequence that facilitates isolation, purification or detection of a protein containing a tag. A variety of such tags are known to those skilled in the art and are suitable for use in the present invention. Suitable tags include, e.g., HA peptide, polyhistidine peptides, biotin/avidin, FLAG, and a variety of antibody epitope binding sites. Techniques known to modify a DNA molecule to cause certain desirable changes in the amino acid sequence encoded by such DNA molecule, such as PCR, may be employed. In a particularly preferred embodiment, a FLAG tag is added to the inventive relaxin-3 chimeric polypeptides.

The identified interaction between the inventive relaxin-3 chimeric polypeptides and GPCR135 and GPCR142 allows for the employment of either GPCR135 or GPCR142, or GPCR135/relaxin-3 chimeric polypeptide complexes or GPCR142/relaxin-3 chimeric polypeptide complexes, in screening methods or assays for identifying compounds for their potential efficacy or selectivity in modulating the activity of such receptors or such receptor-ligand complexes.

Thus, another general aspect of the invention relates to a method for a identifying a compound that modulates a biological activity of at least one receptor selected from the group consisting of GPCR135 and GPCR142, comprising the steps of: (a) contacting a test sample comprising a compound with an assay reagent comprising the at least one receptor and a relaxin-3 chimeric polypeptide as defined in; (b) determining the biological activity of the at least one receptor after performing step (a); and (c) comparing the biological activity determined in step (b) with a control measurement obtained by contacting a control sample not containing the compound with the assay reagent.

In a preferred embodiment of the invention, the determination of biological activity comprises identifying the formation of a receptor-ligand complex. The receptor ligand complexes of the invention can be formed by adding the ligand component to a receptor component-expressing host cell in the form of a purified protein, or in the form of a cell or tissue extract containing the ligand component, as described above.

A variety of labels can be used to label the ligand component, such as those that provide direct detection (e.g., radioactivity, luminescence, optical or electron density), or indirect detection (e.g., epitope tag such as the FLAG epitope, or enzyme tag such as horseradish peroxidase). In a particularly preferred embodiment, the ligand component is radiolabeled and the identification of the formation of a receptor-ligand complex is performed by radiography.

In preferred embodiments of the invention, the GPCR135 or GPCR142, or GPCR135 and GPCR142, is a component of a membrane on the cell surface of a host cell.

In other preferred embodiments, the modulation of a biological activity of the at least one receptor described above is determined by measuring a second messenger response of a host cell expressing at least of receptor selected from the group consisting of GPCR135 and GPCR142, or isolated membranes comprising such at least one receptor. For example, the biological activity of the complex can be measured by the signal transduction event triggered by activated GPCR135 or GPCR142. This signal transduction event can be measured indirectly by means of measuring one or more changes in cellular physiology, such as cell morphology, migration, or chemotaxis, using one or more suitable methods known in the art. It can also be measured directly by measuring phosphorylation of proteins involved in the signal transduction pathway, for example, the phosphorylation of a GTP-binding protein (G protein). Methods are known in the art for measuring protein phosphorylation, for example, by using an ATP or GTP molecule that has been radiolabeled on the γ-phosphate. A variety of labels can be used to label the GTP molecule on the γ-phosphate, such as a fluorescent molecule or a radioactive isotope such as $^{35}$S, $^{32}$P, and the like.

The biological activity of the inventive receptor/ligand complexes can also be measured by the intracellular concentration of a second messenger molecule using any of a number of suitable techniques known in the art. For example, the pH change can be measured using a pH-sensitive dye, such as Acridine Orange. The calcium concentration can be measured via optical imaging of fluorescent indicators sensitive to $Ca^{2+}$, such as fluo-3 (pentapotassium salt, cell-impermeant form; Molecular Probes) or fluo-3(AM) (an acetoxymethyl ester form of fluo-3, Teflabs) (see for example, Liu et al., 2001, *J. Pharmacol. Exp. Ther.*, 299:121-130) using a fluorometric imaging plate reader (FLIPR) or a confocal microscope. The cAMP concentration can be detected using a commercially available ELISA kit (FLASHPLATE cyclic AMP assay system ($^{125}$I), Cat. No: SMP001A, NEN; see also Shimomura et al., 2002, *J. Biol. Chem.*, 277: 35826-35832), or via a reporter system wherein the expression of a reporter gene, such as beta-galactosidase, is under the control of a cAMP responsive element (cre) (Montminy et al., 1990, *Trends Neurosci.*, 13(5):184-188).

The test compound can be further characterized by comparing its effect on two cells, the first cell containing a functional GPCR135 or GPCR142, or both a GPCR135 and a GPCR142, and the second one identical to the first, but lacking a functional GPCR135 or GPCR142, or lacking both GPCR135 and GPCR142. This technique is also useful in establishing the background noise of these assays. Skilled artisans in the art will appreciate that this control mechanism also allows ready selection of cellular changes that are responsive to modulation of functional GPCR135 or GPCR142, or GPCR135 and GPCR142. Therefore, in preferred exemplary embodiments, the screening method comprises the steps of: (a) contacting a first cell having a GPCR135 or a GPCR142, or both a GPCR135 and a GPCR142, expressed on the cell surface with a ligand component and with a test compound; (b) determining a second messenger response in the first cell to the test compound, and comparing it with that of a control wherein the first cell is only contacted with the ligand component, but not the test compound; (c) contacting a second cell with the ligand component and with a test compound; wherein the second cell is otherwise identical to the first cell except that it does not express one or both of the GPCR135 or the GPCR142 on the cell surface; (d) determining a second messenger response of the second cell to the test compound, and comparing the second messenger response with that of a control wherein the second cell is only contacted with the ligand component, but not the test compound; and (e) comparing the comparison result of (b) with that of (d).

There are a number of ways to obtain two cells that are otherwise identical except that one expresses a receptor component on its cell surface and the other does not. In one embodiment, the first cell is a recombinant host cell for either GPCR135 or GPCR142 that constitutively expresses either GPCR135 or GPCR142 on its cell surface, and the second cell is the parent cell from which the GPCR135 or GPCR142 recombinant cell is constructed. In another embodiment, a recombinant host cell for either GPCR135 or GPCR142 is constructed such that its expression on the cell surface is under the control of an inducible promoter. The first cell is the recombinant cell grown under inducible conditions that allows the expression of either GPCR135 or GPCR142 on its cell surface, and the second cell is the recombinant cell grown under non-inducible conditions that do not allow the expression of either GPCR135 or GPCR142. In yet another embodiment, the first cell is a native host cell for either GPCR135 or GPCR142 that expresses the polypeptide on its cell surface, and the second cell is a mutant cell derived from the native host, wherein either the GPCR135 or the GPCR142 gene has been inactivated through mutagenesis. Standard molecular biology methods can be used to construct a recombinant host cell for either GPCR135 or GPCR142, or to inactivate either a GPCR135 gene or a GPCR142 gene.

In other preferred embodiments of the invention, the assay methods described above are employed with an isolated membrane of which the GPCR135 or GPCR142, or GPCR135 and GPCR142, is a component. The membrane can be isolated from a native host cell that expresses either GPCR135 or GPCR142, or both GPCR135 and GPCR142, on its cell surface, or preferably, from a recombinant host cell that expresses an increased amount such receptor(s) on its cell surface. It can also be isolated from tissues comprising GPCR135 or GPCR142 host cells. Alternatively, synthetic membranes comprising the receptor(s) can be prepared by means that are available in the art.

Active compounds or modulators, identified as described above, as well as the inventive polypeptides, polynucleotides, and expression vectors, may be used as therapeutic agents in treating a subject suffering from a disease or disorder mediated through modulation of GPCR135 and/or GPCR142, or the interaction of relaxin-3 or ligand with such receptor(s), or the receptor/ligand complex(es). Such diseases or disorders may include, e.g., CNS disorders (anxiety, schizophrenia, depression, mood, sleep/wake), metabolic disorders, feeding/drinking disorders, water and nutrient homeostasis, and endocrine disorders, aural sensory processing disorders, visual attention and saccadic eye movement disorders, disorders associated with processing of tactile stimuli, disorders associated with sensory processing, integration, and motor control, and disorders associated with regulatory sensory perception, sensory-motor reflexes under stressful conditions, and disorders associated with aberrant functional activity of the lateral septum, hebenula, superior colliculus, inferior colliculus, amygdala, thalamus, interpeduncular nucleus, hypothalamus, supraoptic nucleus, dorsal raphe, dentate gyrus, olfactory bulb, and solitary tract. Such modulators may also be used to treat reproductive disorders and dysfunctions, such as infertility, and may be employed as contraceptive agents. See e.g., Goto et al., 2001, *J. Comp. Neurol.*, 438:86-122; Osheroff et al., 1991, *Proceedings of the National Academy of the Sciences USA*, 88(15):6413-6417; Adams et al., 2000, *Brain Research*, 858(1):177-180; Liu et al., 2003, *Journal of Biological Chemistry* 278(50):50754-50764; Chalmers et al., 1995, *Journal of Neuroscience* 15(10):6340-6350; Potter et al., 1994, *Proceedings of the National Academy of the Sciences USA* 91:8777-8781; Van Pett et al., 2000, *Journal of Comparative Neurology*, 428:191-212).

Modulators that decrease a biological activity are often referred to as inhibitors, which include compounds that decrease, prevent, inactivate, desensitize, antagonize, repress, corepress, abrogate, down-regulate or compete with receptor or ligand expression, activity or interaction (e.g., GPCR135/relaxin-3 chimeric polypeptide complex expression or activity GPCR142/relaxin-3 chimeric polypeptide complex expression or activity, or expression or activity of both receptor/relaxin-3 chimeric polypeptide complexes or a receptor or ligand individually). Modulators that increase a biological activity are often referred to as activators, which include compounds that increase, effect, activate, coactivate, sensitize, agonize, stimulate, facilitate, promote, sensitize or up-regulate receptor and/or ligand expression, activity or interaction. "Modulators" are intended to include both "inhibitors" and "activators," as well as agonists, antagonists, and inverse agonists.

The compound identification methods can be performed using conventional laboratory formats or in assays adapted for high throughput. The term "high throughput" refers to an assay design that allows easy screening of multiple samples simultaneously or single samples rapidly, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid-handling experiments. Of course, as miniaturization of plastic molds and liquid-handling devices are advanced, or as improved assay devices are designed, greater numbers of samples will be able to be screened more efficiently using the inventive assay.

Candidate compounds for screening can be selected from numerous chemical classes, preferably from classes of organic compounds. Although candidate compounds can be macromolecules, preferably the candidate compounds are small-molecule organic compounds, i.e., those having a molecular weight of greater than 50 and less than 2500. Candidate compounds have one or more functional chemical groups necessary for structural interactions with polypeptides. Preferred candidate compounds have at least an amine, carbonyl, hydroxyl or carboxyl group, preferably at least two such functional groups, and more preferably at least three such functional groups. The candidate compounds can comprise cyclic carbon or heterocyclic structural moieties and/or aromatic or polyaromatic structural moieties substituted with one or more of the above-exemplified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound is preferably a DNA or RNA molecule, although modified nucleic acids having non-natural bonds or subunits are also contemplated.

Candidate compounds may be obtained from a variety of sources, including libraries of synthetic or natural compounds. For example, numerous means are available for random and directed synthesis of a variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid-phase or solution-phase libraries; synthetic library methods requiring deconvolution; the "one-bead one-compound" library method; and synthetic library methods using affinity chromatography selection (see, e.g., Lam, 1997, *Anti-Cancer Drug Des.*, 12:145). Alternatively, libraries of natural compounds in the form of bacterial, fungal, plant and animal extracts are available or may be routinely produced. Additionally, natural and synthetically produced libraries and compounds can be routinely modified through conventional chemical, physical, and biochemical means.

Furthermore, known pharmacological agents can be subjected to directed or random chemical modifications, such as acylation, alkylation, esterification, and amidification to produce structural analogs of the agents. Candidate compounds can be selected randomly or can be based on existing compounds that bind to and/or modulate the function or activity of a GPCR or of one of the inventive relaxin-3 chimeric polypeptides. Therefore, a source of candidate agents is known or screened libraries of molecules including activators or inhibitors of GPCRs with similar structures to GPCR135, GPCR142, or the inventive relaxin-3 chimeric polypeptides. The structures of such compounds may be changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions.

A variety of other reagents also can be included in the assay mixture. These include reagents such as salts, buffers, neutral proteins (e.g., albumin), and detergents that can be used to facilitate optimal protein-protein and/or protein-nucleic acid binding. Such a reagent can also reduce non-specific or background interactions of the reaction components. Other reagents that improve the efficiency of the assay, such as nuclease inhibitors, antimicrobial agents, and the like, can also be used.

Examples of methods for the synthesis of molecular libraries can be found in the art, for example in Zuckermann et al., 1994, *J. Med. Chem.*, 37:2678. Libraries of compounds can be presented in solution (e.g., Houghten, 1992, *Biotechniques*, 13:412-421), or on beads (Lam, 1991, *Nature*, 354: 82-84), chips (Fodor, 1993, *Nature*, 364:555-556), bacteria (U.S. Pat. No. 5,223,409), spores (U.S. Pat. No. 5,571,698), plasmids (Cull et al., 1992, *Proc. Natl. Acad. Sci. USA*, 89:1865-1869) or phage (see e.g., Scott et al., 1990, *Science*, 249:386-390).

Thus, in one general aspect the invention relates to a method of identifying a compound that binds to at least one receptor selected from the group consisting of GPCR135 and GPCR142, comprising the steps of: (a) contacting the at least one receptor with a test compound and with a labeled relaxin-3 chimeric polypeptide; (b) determining the amount of the labeled relaxin-3 chimeric polypeptide that binds to the at least one receptor; and (c) comparing the amount determined in step (b) with a control measurement obtained by contacting the at least one receptor with the labeled relaxin-3 chimeric polypeptide in the absence of the test compound.

In yet other embodiments, the present invention provides a method of identifying a compound that binds to at least one receptor selected from the group consisting of GPCR135 and GPCR142, comprising the steps of: a) contacting a receptor component with a test compound and with a labeled ligand component; b) measuring the amount of the labeled ligand component that binds to the at least on receptor; and c) comparing the measured amount of (b) with that of a control measurement obtained by contacting the receptor(s) with the labeled ligand component in the absence of the test compound.

In one preferred exemplary embodiment, a receptor host cell (recombinant or native) that expresses the at least one receptor on the cell surface can be used for the binding assay. In another preferred exemplary embodiment, isolated membrane preparations comprising the at least one receptor can be used for the binding assay. In yet another preferred embodiment, a substantially purified extracellular fragment of the at least one receptor that is capable of binding to an inventive relaxin-3 chimeric polypeptide can be used for the binding assay.

The amount of the labeled ligand component or fragment thereof that binds to the at least one receptor can be measured by first separating the unbound labeled ligand component or fragment the at least one receptor, and then measuring the amount of labeling that is associated with the at least one receptor.

Separation of the at least one receptor protein from unbound labeled ligand components can be accomplished in a variety of ways. Conveniently, the at least one receptor may be immobilized on a solid substrate, from which the ligand component can be easily separated. The solid substrate can be made of a variety of materials and in a variety of shapes, e.g., microtiter plate, microbead, dipstick, and resin particle. The substrate preferably is chosen to maximize signal-to-noise ratios, primarily to minimize background binding, as well as for ease of separation and cost.

Separation can be effected by, for example, removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells can be washed several times with a washing solution, e.g., that includes those components of the incubation mixture that do not participate in specific bindings, such as salts, buffer, detergent, non-specific protein, etc. Where the solid substrate is a magnetic bead, the beads can be washed one or more times with a washing solution and isolated using a magnet.

The at least one receptor can be immobilized on a solid substrate using a number of methods. In one embodiment, a fusion protein can be provided which adds a domain that allows the at least one receptor proteins to be bound to a matrix. For example, glutathione-S-transferase fusion proteins or glutathione-S-transferase fusion proteins can be adsorbed onto glutathione sepharose beads (Sigma Chemical, St. Louis, Mo.) or glutathione derivatized microtiter plates, which are then combined with the test compound and the labeled ligand component, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding of the labeled ligand component to the at least one receptor can be determined using standard techniques.

Other techniques for immobilizing proteins on matrices can also be used in the screening assays of the invention. For example, the at least one receptor can be immobilized utilizing conjugation of biotin and streptavidin. Biotinylated polypeptide can be prepared from biotin-NHS (N-hydroxy-succinimide) using techniques known in the art (e.g., biotinylation kit available from Pierce Chemicals, Rockford, Ill.), and immobilized in the wells of streptavidin-coated 96-well plates (Pierce Chemicals).

Alternatively, antibodies reactive with the receptor(s) but which do not interfere with binding of the at least one receptor to the ligand component or test compound can be attached to the wells of the plate, and the at least one receptor then trapped in the wells by antibody conjugation.

A variety of labels can be used to label either the ligand component or fragments thereof, such as those that provide direct detection (e.g., radioactivity, luminescence, optical or electron density), or indirect detection (e.g., epitope tag such as the FLAG epitope, or enzyme tag such as horseradish peroxidase).

Interaction of the at least one receptor to the ligand component in the presence and absence of a candidate compound can be accomplished in any vessel suitable for containing the reactants. Examples of such vessels include microtiter plates, test tubes, and micro-centrifuge tubes.

Further, the receptor can be modified to produce constitutive activity. This constitutive activity can be suppressed by an inverse agonist.

In certain embodiments or the present invention, methods are provided for treating a medical condition mediated by modulation of receptor or ligand activity, expression or interaction, comprising administering to a subject in need thereof a therapeutically effective amount of a compound identified as having such modulating activity. The term "treating" includes preventing, decreasing, diminishing, suppressing, alleviating, or ameliorating the symptoms or causes of a medical condition. Such treatment can be therapeutic or prophylactic. The term "subject" as used herein refers to an animal who is the object of treatment, observation or experiment. Preferably, the subject is a mammal, more preferably a human.

A "pharmaceutically effective amount" is an amount or dose sufficient to achieve the desired modulating effect. Suitable amounts for a particular treatment may be ascertained by routine methods such as modeling, dose escalation studies or clinical trials, and by taking into consideration routine factors, e.g., the mode or route of administration or drug delivery, the pharmacokinetics of the agent, the severity and course of the disorder or condition, the subject's previous or ongoing therapy, the subject's health status and response to drugs, and the judgment of the treating physician. An exemplary dose is in the range of from about 0.001 to about 200 mg per kg of subject's body weight per day, preferably about 0.05 to 100 mg/kg/day, or about 1 to 35 mg/kg/day, in single or divided dosage units (e.g., BID, TID, QID). For a 70-kg human, an illustrative dosage amount is from about 0.05 to about 7 g/day, or about 0.2 to about 2.5 g/day.

Once improvement of the patient's conditions has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

The compounds or treatment agents of the invention may be used alone or in combination with one or more other active ingredients, to formulate pharmaceutical compositions of the invention. A pharmaceutical composition of the invention comprises a pharmaceutically effective amount of a compound having modulating activity, which can be determined using methods as described above. A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils and polyethylene glycols.

Delivery forms of the pharmaceutical compositions containing one or more dosage units of the pharmaceutical agents may be prepared using suitable pharmaceutical excipients and compounding techniques known to those skilled in the art. The compositions may be administered in the inventive methods by oral, parenteral, rectal, topical, or ocular routes or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol or water; preservatives (for example, methyl or propyl p-hydroxybenzoate or sorbic acid); wetting agents such as lecithin; and, if desired, flavoring or coloring agents.

The compositions of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Another embodiment of the invention provides a method for treating a medical condition comprising administering a pharmaceutically acceptable composition comprising a pharmaceutically acceptable vector of the invention. Polynucleotides of the invention may be introduced into a cell, in vitro, in vivo, or ex vivo, using any suitable method, e.g., infection with viral vectors, liposome-based methods, biolistic particle acceleration, and naked DNA injection.

Such therapeutically useful nucleic acids include coding sequences for biologically active protein. Such a sequence may be operably linked to a promoter as described above. The nucleic acid may be administered in the form of a cell that is itself directly therapeutically effective, e.g., certain antisense or ribozyme molecules. These antisense molecules may be DNA, stable derivatives of DNA such as phosphorothioates or methylphosphonates, RNA, stable derivatives of RNA such as 2'-O-alkylRNA, or other antisense oligonucleotide mimetics. Antisense molecules may be introduced into cells by microinjection, liposome encapsulation or by expression from vectors harboring the antisense sequence.

Gene therapy techniques may be used to introduce the biologically active protein into the cells of target organisms. To illustrate, the DNA is ligated into viral vectors that mediate transfer of the DNA by infection of recipient host cells. Suitable exemplary viral vectors include retrovirus, adenovirus, adeno-associated virus, herpes virus, vaccinia virus, poliovirus and the like. Alternatively, the DNA can be transferred into cells for gene therapy by non-viral techniques, such as receptor-mediated targeted DNA transfer using ligand-DNA conjugates or adenovirus-ligand-DNA conjugates, lipofection membrane fusion, or direct microinjection. Protocols for molecular methodology of gene therapy suitable for use with the gene of interest are exemplified in GENE THERAPY PROTOCOLS, edited by Paul D. Robbins, Human press, Totawa N.J., 1996.

Pharmaceutically effective compositions comprising DNA, RNA, or polypeptides, or small-molecule modulators of relaxin-3 or receptor activity, may be formulated according to known methods such as by the admixture of a pharmaceutically acceptable carrier. Examples of such carriers and methods of formulation may be found in REMINGTON'S PHARMCEUTICAL SCIENCES. To form a pharmaceutically acceptable composition suitable for effective administration, such compositions will contain an effective amount of the polypeptide, DNA, RNA, or modulator.

Other illustrative features and preferred embodiments of the invention are described in the following examples.

Example 1

Cloning, Expression and Purification of Relaxin-3 Chimeric Polypeptides, GPCRs, LGRs, and Expression Vectors Encoding Same Construction of Chimeric Polypeptide Expression Constructs A series of chimeric polypeptides were prepared by creating gene cassettes which included coding regions for an alpha peptide signal peptide, a FLAG tag, the human relaxin-3 B-chain, the human relaxin-3 C-chain, and an A-chain from one of the following: relaxin-1 (Hudson et al., 1983, *Nature*, 301:628-631), relaxin-2 (Hudson et al., 1984, *EMBO Journal*, 3:2333-2339), INSL3 (Adham, et al., 1993, *Journal of Biological Chemistry* 268:26668-26672), INSL4 (Koman et al., 1996, *Journal of Biological Chemistry*, 271:20238-20241), INSL5 (Conklin et al., 1999, *Genomics*, 60:50-56), INSL6 (Lok et al., 2000, *Biology of Reproduction*, 62:1593-

1599), insulin, or an artificial A-chain, in which only the cysteine residues remained unchanged while all the other amino acids residues were randomly assigned. The junction of the C-chain and the A-chain for each construct contained an artificial furin cleavage site (RGRR) derived from the Relaxin-3 RR expression vector from which the coding regions of inventive chimeric polypeptides were PCR amplified (Liu et al., 2003, *Journal of Biological Chemistry*, 278: 50754-50764). This furin cleavage sight allowed for efficient in vivo cleavage of the chimeric propeptides when co-expressed with furin (Hosaka et al., 1991, *Journal of Biological Chemistry*, 266:12127-12130; Liu et al., 2003, *Journal of Biological Chemistry*, 278:50754-50764).

PCR Amplification of the Coding Regions for the Chimeric Peptides

A Relaxin-3/Relaxin-1 ($R_3/R_1$) chimeric polypeptide comprises a relaxin-3 B-chain and a relaxin-1 A-chain. The DNA coding region for such chimeric polypeptide was PCR amplified using modified human relaxin-3 expression vector relaxin-3 RR (Liu et al., 2003, *Journal of Biological Chemistry*, 278:50754-50764) as template and using primers P1 (NO: 32)(5' ACT AGA CTG CAG GCC GCC ATG CTG ACC GCA GCG T 3') and P2 SEQ ID NO:33)(5' ACT AGA GGA TCC TCA GCA ATA TTT AGC AAG AGA CCT TTT GGT ACA ACC AAT TAG GCA ACA TTT CTC AAA CAG TGC CAC GTA GGG TCG TCG TCG GCC CCG AAG AAC CCC AGG 3').

A Relaxin-3/Relaxin-2 ($R_3/R_2$) chimeric polypeptide comprises a relaxin-3 B-chain and a relaxin-2 A-chain. The DNA coding region for such chimeric polypeptide was PCR amplified using modified human relaxin-3 expression vector Relaxin-3 RR (see above) as template and using primers P1 (SEQ ID NO:32 above) described above and P3 (SEQ ID NO:34)(5' ACT AGA GGA TCC TCA GCA AAA TCT AGC AAG AGA TCT TTT GGT ACA ACC AAC ATG GCA ACA TTT ATT AGC CAA TGC ACT GTA GAG TTG TCG TCG GCC CCG AAG AAC CCC AGG 3').

A Relaxin-3/INSL3 ($R_3/I_3$) chimeric polypeptide comprises a relaxin-3 B-chain and an INSL3 A-chain. The DNA coding region for such chimeric polypeptide was PCR amplified using modified human relaxin-3 expression vector Relaxin-3 RR (see above) as template and using primers P1 (SEQ ID NO:32 above) and P4 (SEQ ID NO:35) (5' ACG ATA GGA TCC TCA GCA CAG GGT CAG CAG GTC CTG CTG GGT GCA GCC GGA CAG GCA GCA GTA GCG GGC GGG GTT TCG TCG GCC CCG AAG AAC CCC AG 3').

A Relaxin-3/INSL4 ($R_3/I_4$) chimeric polypeptide comprises a relaxin-3 B-chain and an INSL4 A-chain. The DNA coding region for such chimeric polypeptide was PCR amplified using modified human relaxin-3 expression vector Relaxin-3 RR as template and using primers P1 (SEQ ID NO:32 above) and P5 (SEQ ID NO:36) (5' ATG ACA GGA TCC TCA GCA CAG CTT CAC GGA GGT GCC GTC GTC GCA GAT CAC CTC GCA GCA GAA GGG GTC GAA TCG TCG GCC CCG AAG AAC CCC AGG 3').

A Relaxin-3/INSL5 ($R_3/I_5$) chimeric polypeptide comprises a relaxin-3 B-chain and an INSL5 A-chain. The DNA coding region for such chimeric polypeptide was PCR amplified using modified human relaxin-3 expression vector Relaxin-3 RR as template and using primers P1 (SEQ ID NO:32 above) and P6 (SEQ ID NO:37) (5' ATA GAA GGA TCC TTA GCA AAG AGC ACT CAA ATC AGT CAT GGA ACA GCC ATC AGT GCA ACA CAA AGT TTG TAA ATC TTG TCG TCG GCC CCG AAG AAC CCC AGG GGT TCC 3').

A Relaxin-3/INSL6 ($R_3/I_6$) chimeric polypeptide comprises a relaxin-3 B-chain and an INSL6 A-chain. The DNA coding region was PCR amplified using modified human relaxin-3 expression vector Relaxin-3 RR as template and using primers P1 (SEQ ID NO:32 above) and P7 (SEQ ID NO:38) (5' ATG ACA GGA TCC TCA GCA GGC GAT GGA CAG CTC CTC CTT GGT GCA GCC GGT CAG GCA GCA CTT CTC GGA GTA GCC TCG TCG GCC CCG AAG AAC CCC AG 3').

A Relaxin-3/Insulin ($R_3/I$) chimeric polypeptide comprises a relaxin-3 B-chain and an insulin A-chain. The DNA coding region was PCR amplified using modified human relaxin-3 expression vector Relaxin-3 RR as template and using primers P1 (SEQ ID NO:32 above) and P8 (SEQ ID NO:39) (5' ACG ATA GGA TCC TCA GCA GTA GTT CTC CAG CTG GTA CAG GGA GCA GAT GGA GGT GCA GCA CTG CTC CAC GAT GCC TCG TCG GCC CCG AAG AAC CCC AG 3').

A Relaxin-3/artificial A-chain ($R_3/A$) chimeric polypeptide comprises a relaxin-3 B-chain and an A-chain comprising the conserved cysteine residues and arbitrarily assigned amino acids at the other positions. The DNA coding region was PCR amplified using modified human relaxin-3 expression vector Relaxin-3 RR as template and using primers P1 (SEQ ID NO:32 above) and P9 (SEQ ID NO: 40) (5' ACG ATA GGA TCC TCA GCA GGC CTT CTC GAT CTC GTA GTC GTC GCA GAT GGA CAG GCA GCA GTT CTC GTA CAG GCC TCG TCG GCC CCG AAG AAC CCC AG 3').

Construction of the Expression Vectors for Relaxin-3 Chimeric Peptides

The PCR products for the relaxin-3 chimeric polypeptide coding regions described supra were digested with DNA restriction enzymes Pst 1 and Bam H1 and cloned into a mammalian expression vector, pCMV sport1 (Invitrogen), between Pst1 and Bam H1 sites. The insert region for each construct was sequenced to confirm the sequence identity.

Expression and Purification of Chimeric Peptides

The amino acid sequences of the inventive chimeric polypeptides are depicted in FIG. 2.

Each of the different relaxin-3 chimeric polypeptide expression constructs described were co-transfected with a human Furin expression plasmid (Liu et al., 2003, *Journal of Biological Chemistry*, 278:50754-50764) into COS-7 cells. Three days after transfection, recombinant peptides secreted into the conditioned medium of transfected cells were affinity purified with anti-FLAG affinity column, cleaved with enterokinase (Novagen) to remove the N-terminal FLAG tag (Sigma), and then further purified by reversed phase HPLC using a C-18 column. The purified peptides were characterized by SDS-PAGE under non-reducing conditions to verify purity. The protein expression levels for $R_3/R_2$, $R_3/I_3$, $R_3/I_5$, and $R_3/I_6$ were comparable to the production of relaxin-3 wild type peptides (Liu et al., 2003, *Journal of Biological Chemistry*, 278:50754-50764), which was about 1 mg/L. The production levels of $R_3/R_1$, $R_3/I_4$, were lower at proximately 200 µg/L. Attempts to make $R_3/I$ and $R_3/A$ chimeras resulted in no detectable peptides when analyzed by SDS-PAGE.

Molecular Cloning of GPCR135, GPCR142, LGR7, and LGR8

The cloning, preparation and methods of use of recombinant GPRC135 and recombinant GPCR142 are described in Liu et al., 2003, *Journal of Biological Chemistry*, 278:50754-50764, Liu et al., 2003, *Journal of Biological Chemistry*, 278:50765-50770, in patent applications, WIPO publications WO00/23111, WO00/24891, WO01/48189, WO01/62797, WO01/74904, and WO01/85791, U.S. Provisional Application No. 60/580,083, and U.S. patent application Ser. No. 10/786,478, the disclosures of which are incorporated herein by reference.

Human LGR7 cDNA containing the complete coding region was PCR amplified from a human brain cDNA pool (BD Biosciences, Palo Alto, Calif.) using the following two primers: forward primer (SEQ ID NO:41): 5' AGA TGA GAA TTC GCC ACC ATG ACA TCT GGT TCT GTC TTC TTC TAC 3'; and reverse primer (SEQ ID NO:42): 5' TAG AGA GCG GCC GCT CAT GAA TAG GAA TTG AGT CTC GTT GA 3'), each designed according the published sequence (Hsu et al., 2000, *Molecular Endocrinology*, 14:1257-1271; Hsu et al., 2002, *Science*, 295:671-674).

Human LGR8 cDNA containing the complete coding region was PCR amplified from a human testis cDNA pool (BD Biosciences) using the following two primers forward primer (SEQ ID NO:43): 5' TAG ACA GAA TTC GCC ACC ATG ATT GTT TTT CTG GTT TTT AAA CAT CTC 3'; reverse primer (SEQ ID NO:44): 5' ATG ATA GCG GCC GCC TAG GAA ACT GGT TTC ATT ATA CTG TC 3'), each designed according to the published sequence (Hsu et al., 2002, *Science*, 295:671-674). The resulting LGR7 and LGR8 cDNAs were each separately cloned into the mammalian expression vector pCIneo (Promega) and the insert regions were sequenced to confirm the sequence identities for LGR7 and LGR8, respectively.

Example 2

Characterization of Relaxin-3 B-chain Agonist Activity Towards GPCR135, GPCR142, LGR7, and LGR8

It has been shown that synthetic human relaxin-3 B-chain alone, but not A-chain, is an agonist for both GPCR135 and GPCR142 (Liu et al., 2003, *Journal of Biological Chemistry*, 278:50754-50764 and Liu et al., 2003, *Journal of Biological Chemistry*, 278:50765-50770). Those studies were repeated herein in SK-N-MC/β-gal cells, which harbor a β-galactosidase gene under the control of a cAMP responsive element (CRE) (Liu et al., 2001, *Molecular Pharmacology*, 59:420-426). In such SK-N-MC/β-gal cells, an increase in intracellular cAMP concentration leads to increased β-galactosidase gene expression, the activity of which is measured using Chlorophenol Red-β-D-Galactopyranoside (CPRG) as the substrate.

Figure 1A:
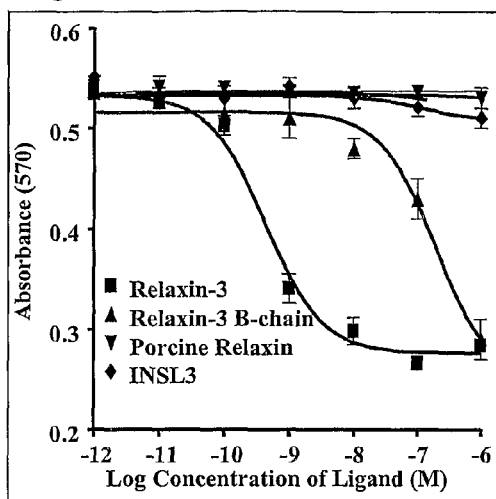
FIGS. 1A-1D show the activation of GPCR135 and GPCR142 by relaxin-3 B-chain, but not of LGR7 or LGR8.
Figure 1B:
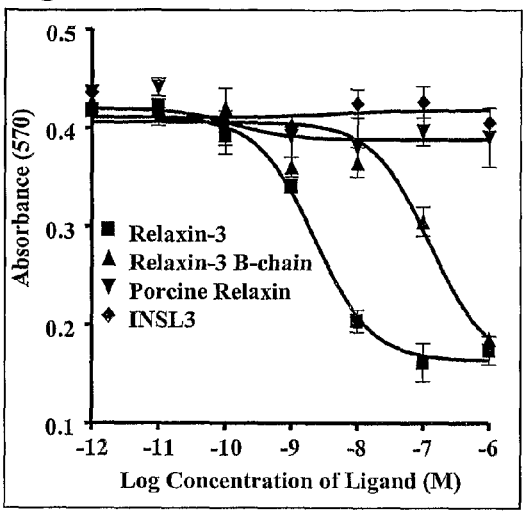
Figure 1C:
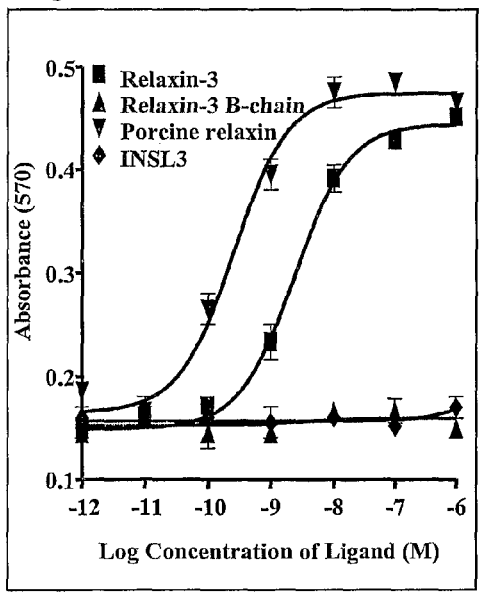
Figure 1D:
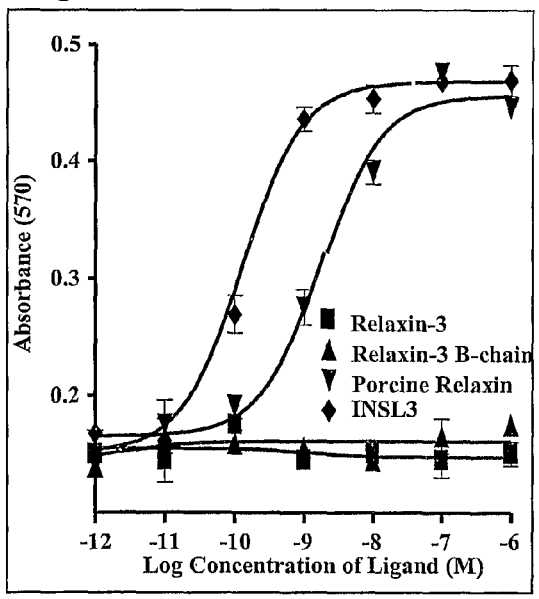

The results indicate that relaxin-3 B-chain inhibited forskolin-stimulated β-galactosidase activity in SK-N-MC/β-gal cells expressing GPCR135 (with an $EC_{50}$ value of 88 nM, FIG. 1A) or GPCR142 (with an $EC_{50}$ value of 125 nM, FIG. 1B) in a dose-dependent manner. In parallel experiments, human relaxin-3 B-chain did not activate either LGR7 (FIG. 1C) or LGR8 (FIG. 1D) expressing cells, whereas porcine relaxin and human relaxin-3 stimulated β-galactosidase activity in LGR7 expressing cells (with $EC_{50}$ values of 0.25 nM and 1.4 nM, respectively, FIG. 1C), and porcine relaxin and human INSL3 induced β-galactosidase activity in LGR8 expressing cells (with $EC_{50}$ values of 1.5 nM and 0.16 nM, respectively, FIG. 1D).

Example 3

Figure 3A:
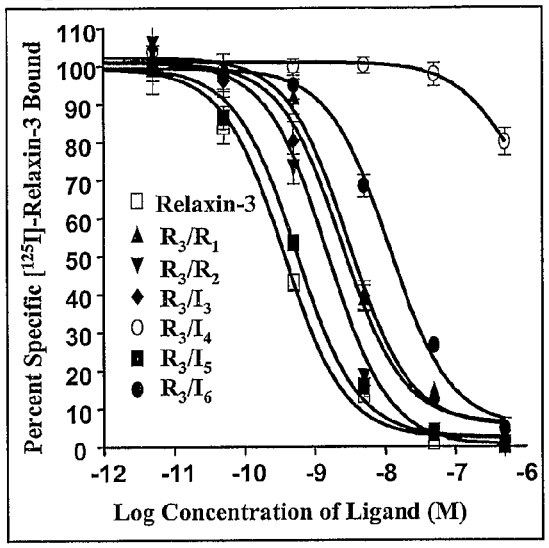
FIGS. 3A-3D illustrate the characterization of various relaxin-3 chimeric polypeptides using radioligand binding assays. Different relaxin-3 chimeric polypeptides were characterized for their receptor binding properties for human recombinant GPCR135 (FIG. 3A), GPCR142 (FIG. 3B), LGR7 (FIG. 3C), or LGR8 (FIG. 3D). For GPCR135, GPCR142, and LGR7, [$^{125}$I]-relaxin-3 was used as the radioligand at a final concentration of 100 pM. Different unlabeled peptides were used in the binding assay as the competitors. For LGR8, [$^{125}$I]-INSL3 was used as the radioligand at a final concentration of 100 pM. Different unlabeled peptides including relaxin-3 chimeras at various concentrations were added to the binding assay as the competitors. The $IC_{50}$ values of different chimeras to different receptors are provided in Table 1 below. Data represent mean±SEM (n=3).
Figure 3B:
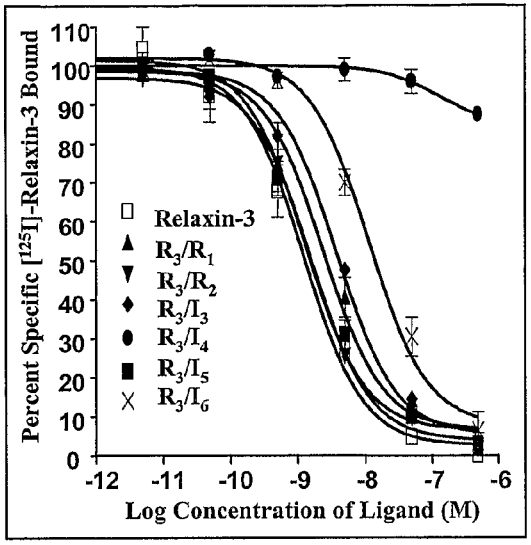
Figure 3C:
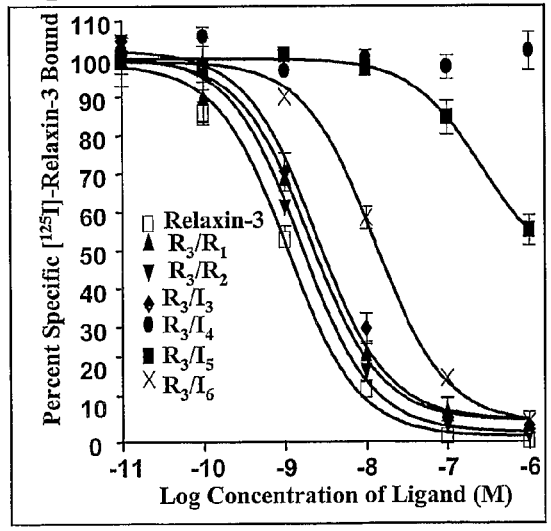
Figure 3D:
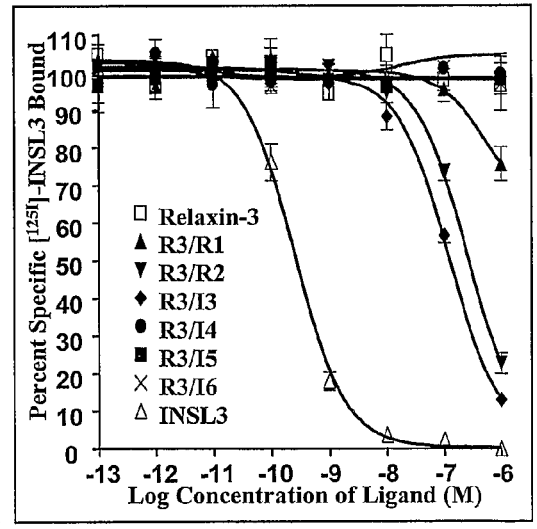
Figure 4A:
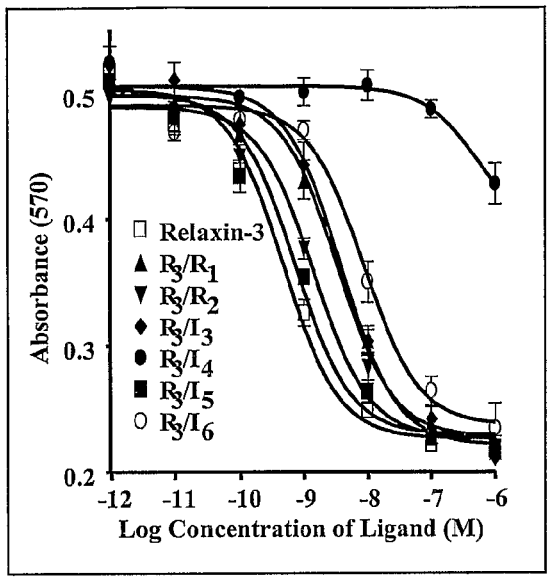
FIGS. 4A-4D illustrate the evaluation of the agonist activity of relaxin-3 chimeric polypeptides in biofunctional assays. Different chimeric polypeptides at various concentrations were added to SK-N-MC/β-gal cells expressing human GPCR135 (FIG. 4A) or GPCR142 (FIG. 4B) to inhibit forskolin stimulated β-galactosidase expression. Human relaxin-3 was used as the positive control. In parallel, chimeric polypeptides at various concentrations were added to SK-N-MC/β-gal cells expressing human LGR7 (FIG. 4C) and LGR8 (FIG. 4D) to stimulate β-galactosidase expression. Relaxin-3 and INSL3 were used as positive controls for LGR7 and LGR8, respectively. Intracellular β-galactosidase activity was measured by a colorimetric assay using CRGP as the substrate and reading the absorbance at wavelength of 570 nm. The $EC_{50}$ values of different chimeras to the four receptors are listed in Table 2. Data represent mean±SEM (n=3).
Figure 4B:
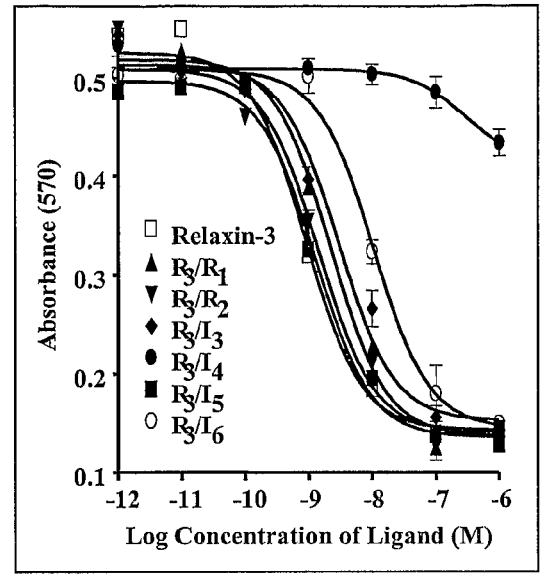
Figure 4C:
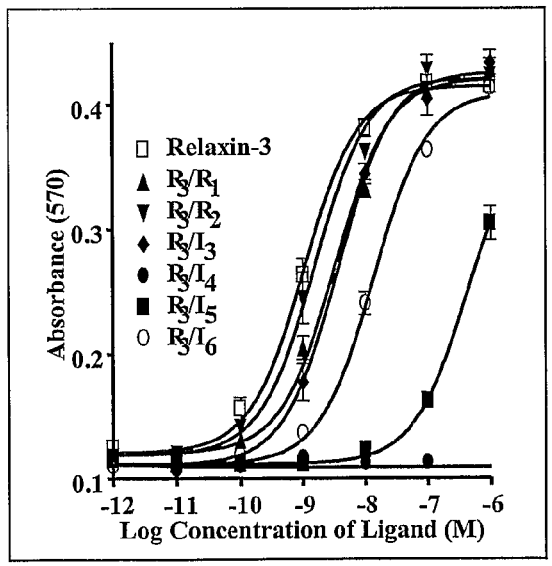
Figure 4D:
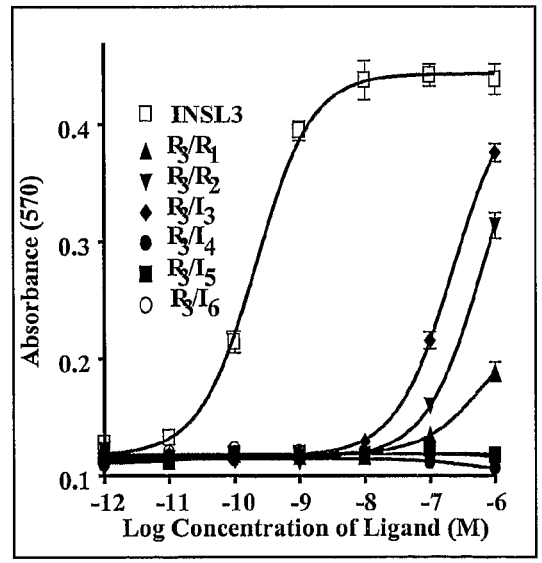

Pharmacological Characterization of Relaxin-3 Chimeric Polypeptides by Radioligand Binding The inventive chimeric polypeptides were tested as ligands for GPCR135 (FIG. 3A), GPCR142 (FIG. 3B), LGR7 (FIG. 3C) and LGR8 (FIG. 3D) in radioligand binding assays to evaluate their receptor binding properties.

Radioligand binding assays for GPCR135 and GPCR142 were performed as previously described (Liu et al., 2003, *Journal of Biological Chemistry*, 278:50754-50764 and Liu et al., 2003, *Journal of Biological Chemistry*, 278:50765-50770). Membranes from COS-7 cells transiently transfected with either the GPCR135 expression vector or the GPCR142 expression vector, each described supra, were incubated with [$^{125}$I]-relaxin-3 at a final concentration 100 pM in 96-well plates. Peptides for competition binding studies were added to the binding mix (final volume: 200 µl) in binding buffer [50 mM Tris-HCl, pH 7.5, 5 mM EDTA, 1% bovine serum albumin, 0.1% protease inhibitor cocktails (Sigma)]. The binding mixtures were incubated at room temperature for 1 hour, filtered through GFC plates (Packard) pre-saturated with 0.3% Polyethylenimine (Sigma), and washed with cold washing buffer (50 mM Tris-HCl, pH 7.5, 5 mM EDTA). Microscint-40 was added to each well and the bound [$^{125}$I]-relaxin-3 was counted in a scintillation counter (TopCount/NTX, Packard).

Radioligand binding assays for LGR7 and LGR8 were performed using live COS-7 cells transiently transfected with LGR7 or LGR8 expression plasmids in 15-cm culture dishes using LipofectAmine (Invitrogen). Two days after transfection, the transfected cells were detached from the 15-cm culture dished using phosphate buffered saline (PBS) plus 10 mM EDTA, seeded into 96-well opaque poly-D-lysine coated culture plates and used for radioligand binding assays. For LGR7, [$^{125}$I]-relaxin-3 was used as the tracer. For LGR8, [$^{125}$I]-INSL3 (specific activity: 2200 Ci/mmol) was used as the tracer. [$^{125}$I]-labeled tracer was added in binding reactions at a final concentration of 100 pM in binding buffer containing DMEM plus 50 mM HEPES and 1% bovine serum albumin. Unlabeled relaxin-3 and relaxin-3 chimeric polypeptides were added at various concentrations to the binding assays as the competitors, as indicated (FIG. 3). The binding mixtures were incubated at room temperature for 1 hour. The unbound radioligand was removed by aspiration of the binding buffer. The cells were washed with PBS. The bound radioligand was counted in a scintillation counter (TopCount/NTX). The results were analyzed using Prism 3.0 program (Graphpad, San Diego, Calif.). The $IC_{50}$ values represent the ligand concentrations that inhibit 50% of the maximum specific binding.

The $IC_{50}$ values of different chimeric polypeptides for GPCR135, GPCR142, LGR7, and LGR8 are listed in Table 1.

The results showed that all chimeric polypeptides, except $R_3/I_4$, bound both GPCR135 and GPCR142 with high affinity (i.e., $IC_{50}$ values in the low nanomolar range), but with slight differences in potency. $R_3/I_4$ demonstrated marginal binding at the highest concentration (1 µM). Chimeric polypeptides $R_3/R_1$, $R_3/R_2$, and $R_3/I_3$, bound to LGR7 with $IC_{50}$ values in low nanomolar range, which is similar to that of relaxin-3. $R_3/I_6$ bound LGR7 with an $IC_{50}$ value of 15 nM. The $R_3/I_5$ chimeric polypeptide, which demonstrated affinity for GPCR135 and GPCR142 in the subnanomolar and low nanomolar range, respectively, showed lower affinity for LGR7, with an $IC_{50}$ value of about 0.5 µM. $R_3/I_4$ was inactive for LGR7 even at the highest concentration tested (1 µM). None of the chimeric polypeptides bound LGR8 with high affinity. $R_3/I_4$, $R_3/I_5$, $R_3/I_6$ showed no binding affinity for LGR8, whereas, chimeric polypeptides $R_3/R_1$, $R_3/R_2$, and $R_3/I_3$, each demonstrated modest binding affinity for LGR8 ($IC_{50}$ values of 0.5 µM to greater than 1 µM).

Example 4

Pharmacological Characterization of Relaxin-3 Chimeric Polypeptides in Functional Assays The inventive chimeric polypeptides were each independently tested for their ability to activate either GPCR135, GPCR142, LGR7, or LGR8, respectively, in separate pools of SK-N-MC/β-gal cells (see supra), each pool stably expressing one of the respective receptors, as indicated (FIG. 4).

Cells were seeded in 96-well tissue culture plate at a density of 30,000 cells/well in MEM plus 10% fetal serum, sodium pyruvate, penicillin, streptomycin, and G418 (400 mg/L). For cells expressing GPCR135 or GPCR142, forskolin was added to cells at a final concentration of 5 µM to stimulate intracellular cAMP accumulation. Different concentrations of each of the inventive polypeptides were then added to the cells to inhibit the forskolin induced cAMP accumulation. For cells expressing LGR7 or LGR8, intracellular cAMP was stimulated with each of the inventive chimeric polypeptides at various concentrations.

For all cells, after adding the chimeric polypeptides, cells were incubated for 6 additional hours in 37° C. incubator. The media was then aspirated and the β-galactosidase activities measured as previously described (Liu et al., 2001, *Molecular Pharmacology*, 59:420-426). The results were analyzed by Prism 3.0 software. The $EC_{50}$ values represent the chimeric polypeptide concentrations that achieved 50% of the maximum inhibition of forskolin induced β-galactosidase activity (GPCR135 or GPCR142) or 50% of the maximum chimeric polypeptide induced β-galactosidase activity (LGR7 or LGR8), respectively.

The results demonstrated that all chimeric polypeptides tested act as agonists for both GPCR135 and GPCR142. The chimeric polypeptides, $R_3/R_1$, $R_3/R_2$, $R_3/I_3$, and $R_3/I_5$, showed similar potency towards GPCR135 and GPCR142 compared to that of the wild type relaxin-3, with $EC_{50}$ values in the low nanomolar range. The chimeric polypeptide, $R_3/I_6$, was slightly less potent towards both GPCR135 and GPCR142, with $EC_{50}$ values around 10 nM for each receptor. The chimeric polypeptide, $R_3/I_4$, stimulated GPCR135 or GPCR142 at the highest concentration (1 µM) tested only (Table 2, and FIGS. 4A and 4B).

For cells stably expressing LGR7, the results indicated that the chimeric polypeptides, $R_3/R_1$, $R_3/R_2$, and $R_3/I_3$, exhibited high potency with $EC_{50}$ values around 1 to 5 nM. The chimeric polypeptide, $R_3/I_6$, showed lower potency for LGR7 with an $EC_{50}$ value of 10 nM. The chimeric polypeptide, $R_3/I_5$, a potent agonist for GPCR135 and GPCR142 (see supra), demonstrated low potency for LGR7, with an $EC_{50}$ value of approximately 400 nM. For cells stably expressing LGR8, the chimeric polypeptide, $R_3/R_1$, demonstrated marginal activity at the highest concentration tested (1 µM). The $R_3/R_2$ and $R_3/I_3$ chimeric polypeptides each showed higher potency with $EC_{50}$ values of about 600 nM and 300 nM, respectively. None of the other chimeric polypeptides tested showed activity towards LGR8 in this assay (Table 2, and FIGS. 4C and 4D).

Control SK-N-MC/β-gal cells not expressing recombinant GPCR135, GPCR142, LGR7, or LGR8 did not respond to any polypeptides.

Example 5

Binding of $R_3/I_5$ to GPCR135-Expressing Cells

All the experiments described in this example were carried out in accordance with the Guide for the Care and Use of Laboratory Animals as adopted and promulgated by the US National Institute of Health.

Adult male Sprague-Dawley rats (150-200 g) were asphyxiated by carbon dioxide. Rat brains were immediately removed from the skull and rapidly frozen in dry ice (i.e., solid, subliming $CO_2$). Twenty-micron-thick sagital sections were cut using a Cryostat-microtome (Microm HM505E, Mikron, San Diego, Calif.) and thaw-mounted on adhesive microscope slides (Superfrost+ Plus, VWR). The sections were kept at −70° C. until use. Sections were thawed and dried under a cold air stream and then pre-incubated for 15 min. at room temperature in incubation buffer (20 mM HEPES, pH 7.4, 120 mM $NaCl_2$, 0.22 mM $KH_2PO_4$, 1.3 mM $CaCl_2$, 0.8 MM $MgSO_4$) by immersing sections in a 400 ml jar. Sections were dried again under a cold air stream and incubated for 60 min. with 5 pM [$^{125}$I]-relaxin-3 (specific activity, 2200Ci/mmole) or [$^{125}$I]-$R_3/I_5$ (specific activity, 2200 Ci/mmole) in incubation buffer containing 0.5% BSA and protease inhibitor cocktail (Sigma). Nonspecific binding was determined in the presence of 100 nM of human relaxin-3. After incubation, the excess radioligand was washed off with three repetitive washes, ten minutes each wash, by immersing the slides in the jar containing incubation buffer at 4° C. followed by a quick immersion in water. Sections were dried and exposed to Fujifilm Imaging plates (BAS-MS 2025) for 48 hrs. The imaging plates were scanned using the Fuji Bio-Imaging Analyzer System (BAS-5000) and visualized using ImageGauge V3.12 software.

The results showed that while both [$^{125}$I]-relaxin-3 (FIG. 5A) and [$^{125}$I]-$R_3/I_5$ (FIG. 5B) bind to GPCR135 expressing cells with high affinity, [$^{125}$I]-$R_3/I_5$ produced lower non-specific binding than [$^{125}$I]-relaxin-3. In addition, [$^{125}$I]-$R_3/I_5$ did not demonstrate significant binding to LGR7, whereas [$^{125}$I]-relaxin-3 did. When [$^{125}$I]-relaxin-3 was used as the radioligand on rat brain section, no substantial difference between total binding and non-specific binding (determined in the presence of 100 nM of unlabeled relaxin-3) was observed (FIG. 5C). In contrast, when [$^{125}$I]-$R_3/I_5$ was used as the radioligand, the non-specific binding was reduced (FIG. 5D). GPCR135-like binding sites were observed in-cortex, olfactory bulb, and superior colliculus areas (FIG. 5D).

Discussion of Results from Above Examples

GPCR135 is predominantly expressed in the brain (Matsumoto et al., 2000, *Gene*, 248:183-189; Liu et al., 2003, *Journal of Biological Chemistry*, 278:50754-50764). In vivo administration of relaxin-3 in the brain to activate GPCR135 can be used to study the physiological role of GPCR135, however, such studies are confounded by the activation of LGR7 by relaxin-3 (Sudo et al., 2003, *J. Biol. Chem.*, 278: 7855-7862), which is also expressed in the brain (Tan et al., 1999, *Br. J. Pharmacol.*, 127:91-98; Hsu et al., 2000, *Mol. Endocrinol.*, 14:1257-1271; Hsu et al., 2002, *Science*, 295: 671-674). Selective ligands that specifically activate GPCR135, but not LGR7, are desirable to study the in vivo function of GPCR135. Therefore, the inventive relaxin-3 chimeric polypeptides, e.g., $R_3/I_5$, a peptide that displays high affinity for GPCR135 ($K_d$~0.5 nM) but low affinity for LGR7 ($K_d$~0.5 µM), facilitate the in vivo functional study of GPCR135, such as in rat, which does not have GPCR142.

In addition to the fact that $^{125}$I-relaxin-3 also labels LGR7, the hydrophobic nature of the [$^{125}$I]-relaxin-3 polypeptide results in a high background when applied in the radioligand autoradiography studies. Addition of the INSL5 A-chain to the B-chain of relaxin-3 resulted in a molecule possessing selectivity for GPCR135 and reduced hydrophobicity, providing lower non-specific binding. Using monolayer cells expressing recombinant GPCR135 or LGR7, [$^{125}$I]-$R_3/I_5$ bound GPCR135 with high affinity and produced similar total binding to that of [$^{125}$I]-relaxin-3, but with 5 to 10 times less non-specific binding. In addition, [$^{125}$I]-$R_3/I_5$ does not label LGR7 whereas [$^{125}$I]-relaxin-3 does, confirming [$^{125}$I]-$R_3/I_5$ as an advantageous tool for radioligand autoradiography studies. Direct application of [$^{125}$I]-$R_3/I_5$ in rat brain sections in radioligand autoradiography showed specific binding sites which overlap with the mRNA distribution for GPCR135. Since [$^{125}$I]-$R_3/I_5$ applied in trace concentrations does not bind LGR7, [$^{125}$I]-$R_3/I_5$ may be advantageously employed to selectively study GPCR135 receptor autoradiography in the rat brain, which does not express the GPCR142 receptor protein.

The results also showed that at least 200 µg/L of chimeric polypeptides $R_3/R_1$, $R_3/R_2$, $R_3/I_3$, $R_3/I_4$, $R_3/I_5$, and $R_3/I_6$ was produced by the recombinant system employed, indicating that the A-chains from many members of the insulin/relaxin family, although bearing limited sequence conservation except the conserved cysteine residues, are largely inter-exchangeable for protein folding, disulfide bond formation, protein secretion and maintenance of protein stability. However, chimeric peptide $R_3/A$, in which in the A-chain, only the cysteine residues were left unchanged and all other amino acids were arbitrarily assigned, was not produced in the recombinant system, suggesting that certain structural conformation(s) should be met to yield biologically active relaxin-3 chimera (e.g., a compatible A-chain should pair with the relaxin-3 B-chain to allow protein production in the mammalian cells). The lack of $R_3/I$ chimera production may be explained by the same reason.

In an effort to understand successful pairing of the relaxin-3 B-chain with the A-chains from relaxin, INSL3, INSL4, INSL5, or INSL6 but not the A-chain from insulin, the amino acid sequence of all known members in the family were compared (FIG. 6). Amino acid sequence comparisons for from different members of the insulin/relaxin family indicated that, except for insulin, IGF1 and IGF2, the B-chains from other members of the family have two conserved positively charged amino acids (Arg or Lys) corresponding to the Arg$^8$ and Arg$^{16}$ of the relaxin-3 B-chain. In contrast, the insulin B-chain has His and Glu in the corresponding positions. Similarly, both IGF1 and IGF2 have Thr and Asp in the corresponding positions. These results suggest that insulin and IGFs may be distinct members of the family compared to other members. The A-chains from insulin and IGFs, structurally, may be very distinct from that of other members, therefore not compatible with relaxin-3 B chain. Given the evidence that the above-mentioned positively charged amino acids in relaxin and INSL3 are important for receptor (namely LGR7 and LGR8) binding and activation (Bullesbach et al., 1992, *J. Biol. Chem.*, 267:22957-22960; Bullesbach et al., 1999, *Biochemistry*, 38:3073-3078; 2000; Tan et al., 2002, *Eur. J. Pharmacol.*, 457:153-160), it is likely that insulin and IGFs are distinct members of the family that signal through the single transmembrane spanning/tyrosine kinase receptors (Ullrich et al, 1985, *Nature,* 313:756-761; Ullrich et al., 1986, *EMBO J,* 5:2503-2512). Other members of the family, including relaxin, relaxin-3, INSL3, INSL4, INSL5, and INSL6, may all signal through GPCRs (see Hsu et al., 2003, *Trends Endocrinol. Metab.*, 14:303-309). Based on the sequence/ structure difference and the two different ways that these peptides signal, it is believed that relaxin, relaxin-3, INSL3, INSL4, INSL5, and INSL6 define a relaxin subfamily distinct from insulin and IGFs.

The results from the radioligand binding assays and the functional assays indicated that chimeras including $R_3/R_1$, $R_3/R_2$, $R_3/I_3$ have substantially similar agonist properties to that of the relaxin-3 wild type peptide in terms of their ligand activity for GPCR135, GPCR142, and LGR7. The relaxin-3 B-chain alone is sufficient to activate GPCR135 and GPCR142, suggesting that the B-chain of relaxin-3 may contain the necessary amino acid residues that directly interact with GPCR135 or GPCR142. With the addition of A-chain from other members of the family to the relaxin-3 B-chain, it was anticipated that some of the chimeric peptides would display a high affinity for GPCR135 and GPCR142. Since relaxin-1, relaxin-2, relaxin-3, and INSL3 are natural ligands for either LGR7 (Hsu et al., 2002, *Science,* 295:671-674; Sudo et al., 2003, *J. Biol. Chem.*, 278:7855-7862), LGR8 (Kumagai et al., 2002, *J. Biol. Chem.*, 277:31283-31286; Bogatcheva, et al., 2003, *Mol. Endocrinol.*, 17:2639-2646), or both (Hsu et al., 2002, *Science,* 295:671-674), as was expected, $R_3/R_1$, $R_3/R_2$, $R_3/I_3$ displayed a very similar pharmacological profile to relaxin-3 (i.e., potent ligands for GPCR135, GPCR142, and LGR7). It is also noted that although relaxin-3 is not a ligand for LGR8 (Sudo, et al., 2003, *J. Biol. Chem.*, 278:7855-7862), $R_3/R_1$, $R_3/R_2$, and $R_3/I_3$ have demonstrated ligand activities for LGR8, albeit with very low potency. Since those chimeras have A-chains either from relaxin-1, relaxin-2, or INSL3, which are natural ligands for LGR8, it is possible that the A-chains in those chimeras interact with and stimulate LGR8. It has been demonstrated that the relaxin-3 B-chain alone is not sufficient to activate LGR7 or LGR8. However, the B-chains of relaxin and INSL3 have been reported to play important roles for relaxin and INSL3 to bind to and activate LGR7 or LGR8 (Bullesbach et al, 1992, *J. Biol. Chem.*, 267:22957-22960; Bullesbach et al., 1999, *Biochemistry*, 38:3073-3078; Tan et al., 2002, *Eur. J. Pharmacol.*, 457:153-160). These results suggest that LGR7 and LGR8 interact with both the B-chain and A-chain of their ligands. In addition, the results herein reflect a trend in which chimeras with relaxin-3 B-chain and an A-chain from a natural ligand for LGR7 or LGR8 tended to have higher affinity for LGR7 or to be active for LGR8. Conversely, relaxin-3 chimeric peptides with A-chains from members that are not ligands for LGR7 or LGR8 have lower or no affinity for LGR7 or LGR8, although they may still retain high affinity for GPCR135 and GPCR142.

From the results disclosed herein, a highly selective chimera for GPCR135/GPCR142 versus LGR7 and LGR8 is $R_3/I_5$. $R_3/I_5$ retains high affinity for GPCR135/GPCR142 but displays low affinity for LGR7 and is inactive towards LGR8, indicating that INSL5 may not be a natural ligand for LGR7 or LGR8. The chimeric peptide $R_3/I_6$ showed reasonably high affinity (10-15 nM) for GPCR135/GPCR142 and LGR7, but is inactive for LGR8, suggesting that the cognate receptor for INSL6 may be a close neighbor of LGR7; however, it does not appear to be LGR8. Chimeric peptide $R_3/I_4$ had no activity for LGR7 and LGR8, suggesting that INSL4 is not a ligand for LGR7 or LGR8. The $R_3/I_4$ chimeric peptide demonstrated no improved activity compared to the relaxin-3 B-chain alone in terms of ligand activity for GPCR135 and GPCR142. Given that INSL4 is only found in human (Koman, et al., 1996, *J. Biol. Chem.*, 271:20238-20241; Hsu et al., 2003, *Trends. Endocrinol. Metab.*, 14:303-309), INSL4 may be a unique member of the relaxin subfamily and has distinct structure; therefore the A-chain of INSL4 was not able to present the B-chain of relaxin-3 in the $R_3/I_4$ chimera in an appropriate configuration to interact with GPCR135/GPCR142 at high affinity.

TABLE 1

$IC_{50}{}^a$ (nM) values for relaxin-3 chimeras to binding GPCR135, GPCR142, LGR7 and LGR8

|  | GPCR135 | GPCR142 | LGR7 | LGR8 |
|---|---|---|---|---|
| $R_3/R_1$ | 2.9 ± 0.35 | 2.6 ± 0.31 | 5.1 ± 0.78 | >1000 |
| $R_3/R_2$ | 1.2 ± 0.27 | 1.8 ± 0.36 | 1.5 ± 0.37 | 615 ± 55 |
| $R_3/I_3$ | 2.3 ± 0.32 | 3.5 ± 0.47 | 2.3 ± 0.35 | 475 ± 32 |
| $R_3/I_4$ | >1000 | >1000 | $ND^b$ | ND |
| $R_3/I_5$ | 0.68 ± 0.13 | 1.4 ± 0.35 | 724 ± 83 | ND |
| $R_3/I_6$ | 9.5 ± 1.7 | 11.3 ± 2.3 | 12.9 ± 1.9 | ND |

$^a IC_{50}$ values (mean ± SEM, n = 3) were ligand concentrations that inhibit 50% of the maximum specific bindings
$^b$ND denotes no activity was detected

TABLE 2

$EC_{50}$ (nM) values of relaxin-3 chimeras to activate GPCR135, GPCR142, LGR7 and LGR8

|  | $GPCR135^a$ | $GPCR142^a$ | $LGR7^b$ | $LGR8^b$ |
|---|---|---|---|---|
| $R_3/R_1$ | 1.8 ± 0.27 | 2.2 ± 0.31 | 4.5 ± 0.51 | >1000 |
| $R_3/R_2$ | 1.1 ± 0.14 | 1.4 ± 0.26 | 1.1 ± 0.16 | 575 ± 65 |
| $R_3/I_3$ | 2.2 ± 0.31 | 2.9 ± 0.28 | 2.5 ± 0.32 | 258 ± 42 |
| $R_3/I_4$ | >1000 | >1000 | $ND^c$ | ND |
| $R_3/I_5$ | 0.45 ± 0.1 | 0.91 ± 0.21 | 412 ± 74 | ND |
| $R_3/I_6$ | 8.4 ± 1.6 | 11.2 ± 2.5 | 13.7 ± 1.9 | ND |

$^a EC_{50}$ values (mean ± SEM, n = 3) for GPCR135 and GPCR142 were ligand concentrations that achieve 50% of the maximum ligand induced inhibition of forskolin stimulated β-galactosidase expression
$^b EC_{50}$ values (mean ± SEM, n = 3) for LGR7 and LGR8 were ligand concentrations that induced 50% of the maximum ligand stimulated β-galactosidase expression
$^c$ND denotes no activity was detected Example 6

Materials and Methods

Production and Purification of Relaxin Family Proteins

The relaxin-3/INSL5 (R3/I5) chimeric polypeptide expression construct described in Example 1 was cotransfected into HEK293 cell with a furin expression vector (Liu et al., 2003, *J. Biol. Chem.*, 278:50754-50764) using LipofectaAmine (Invitrogen) as the transfection reagent. The transfected HEK293 cells were selected under G418 (400 mg/L) and the stable transformants were analyzed for R3/I5 fusion protein production by Western Blotting using an anti-FLAG antibody. A clone with high level of R3/I5 expression as well as thorough processing of the pre-propolypeptide was grown in a 1 liter fermenter. The N-terminal FLAG-tagged R3/I5 chimeric peptide was then purified from the medium using an anti-FLAG column as described Liu et al., 2003, *Journal of Biological Chemistry*, 278:50754-50764. Once prepared, stable cells expressing the protein of interest were inoculated into a CellMax Capillary Cell Culture System with a 50 to 150 kDa MWCO membrane and maintained using a CellMax Quad Cell Culture System (Spectrum Laboratories, Rancho Dominguez, Calif.). The transformed HEK-293 cells were grown in Dulbecco's Modified Eagle Medium supplemented with 10 mM HEPES pH 7.4, 1× non-essential amino acid mix, 1 mM sodium pyruvate, 2 mM glutamine, 50 u/ml penicillin and 50 µg/ml streptomycin (all from Hyclone, Logan Utah). Since the molecular weight cutoff of the membranes in the bioreactor was much larger than the molecular radius of the products, the medium from the supply bottle was retained for purification and the cell chamber was left undisturbed. The Bioreactor apparatus was placed in a 37° C. incubator with the $CO_2$ level set at 6%.

Enriched medium from the bioreactor was passed over an affinity column containing anti-FLAG M2 agarose (Sigma, St Louis, Mo.). The column volume and geometry was optimized for the scale of each purification. The enriched medium was passed through the column by gravity, washed with 20 column volumes of Dulbecco's phosphate buffered saline (Hyclone, Logan, Utah) and eluted with 100 mM Glycine HCl pH 3.5. The column was eluted in 1 column volume fractions into test tubes containing equimolar Tris HCl pH 7.5, which immediately pH neutralized the product. Removal of the FLAG tag was accomplished using 10 units/ml enterokinase (Novagen, Madison, Wis.) incubated overnight at 37° C.

Final purification of the cleaved, affinity purified protein was achieved by HPLC. The protein was loaded onto a 10 mm id×250 mm C18 column (Vydac, Hesperia, Calif.) coupled to a Akta chromatograph (Amersham Biosciences, Piscataway, N.J.). The mobile phase was 0.1% trifluoroacetic acid, which flowed through the column at 3 ml/min. The protein was eluted from the column with a acetonitrile gradient. Aliquots of the purified fraction were lyophilized and stored at −80° C.

Preparation of Radioligands

Radioiodination of R3 and the R3/I5 chimera was accomplished as previously described (Vale, et al., 1983, *J. Cell. Biochem.*, 22(2):99-109). Briefly, 1 mCi Na[$^{125}$I] was reacted with 10 µg peptide and 10 µg Chloramine T in 70 µl 100 mM KPO4 pH 7.4 for 30 seconds at room temperature. The reaction was quenched with 50 µl of 10% w/v bovine serum albumin, then pre-purified using Waters Maxi-Clean C18 cartridges (Alltech, San Jose, Calif.). The hydrophilic phase for the reversed phase separations (prepurification and gradient HPLC) was 0.1% TFA and the eluent was 0.1% TFA in acetonitrile. After removing the acetonitrile from the Maxi-Clean eluent by partial lyophilization the labeled compound was further purified by gradient HPLC using a Vydac (Hesperia, Calif.) analytical C18 HPLC column. A gradient of 2% $CH_3CN$/minute was used and fractions were collected every 0.75 minute. Baseline separation was achieved between the iodinated product and reagents in each case.

Radioligand Competition Binding Assays

The assays were performed using [$^{125}$I] human R3 and [$^{125}$I] human R2 (each at a specific activity of 2200 Ci/mmol) as previously described in Liu et al., 2003, *Journal of Biological Chemistry* 278:50754-50764. Cell membranes from COS-7 cells transiently expressing rat GPCR135 or LGR7 were incubated with [$^{125}$I] human R3 or [$^{125}$I] human relaxin-2 (R2) (final concentration 100 pM) in the presence of various concentrations of human relaxin (R1), R3 and R3/I5. The reaction was incubated at room temperature for 1 hour and the membranes were filtered through the 96-well GFC plates (Packard Instrument Co., Meriden, Conn.) using a cell harvester (Packard Instrument Co). The filter was washed with the ice cold washing buffer (50 mM Tris-HCl, pH 7.5). Fifty µl of Microscint 40 (Packard Instrument Co) was added to each well and the plates were counted on a Topcount NTX (Packard Instrument Co). Non-specific binding was determined in the presence of 100 nM R3 for GPCR135 and 100 nM relaxin for LGR7. The results were analyzed using the PRISM software (GraphPad, San Diego, Calif.).

Animals

Adult male Sprague-Dawley rats (150-200 grams) were used in all experiments. They were housed two per cage, in a 12:12 h light:dark cycle and had free access to food and water. All the experiments described in this study have been carried out in accordance with the Guide for the Care and Use of Laboratory Animals as adopted and promulgated by the US National Institute of Health.

Tissue Preparation for In Situ Hybridization and Receptor Autoradiography

Rats were asphyxiated by carbon dioxide. Brains were immediately removed from the skull and rapidly frozen in dry-ice. Twenty-micron-thick frontal sections were cut using a Cryostat-microtome (Microm HM505E, Mikron, San Diego, Calif.) and thaw-mounted on adhesive microscope slides (Superfrost+ Plus, VWR). The sections were kept at −70° C. until use. The sectioning protocol for the regional distribution study included series of coronal sections covering the entire brain. Adjacent sections at the level of olfactory bulb, cortex and superior colliculus were used to generate concentration binding curves.

In Situ Hybridization

In situ hybridization was performed using a protocol taken from Simmons et al. (Simmons et al., 1989, *Journal of Histotechnology* 12(3):169-181) A full-length probe was prepared from the full-length rat GPCR135 cDNA (GenBank accession number AY394501) cloned into the pCI-Neo plasmid. Transcription was accomplished using the Promega (Madison, Wis.) Riboprobe Combination T3/T7 kit and [$^{35}$S]-UTP from Perkin Elmer (Boston, Mass.). Twenty micron sections prepared as described above were fixed onto Superfrost+slides using 40 g/l paraformaldehyde buffered to pH 9.5 with sodium tetraborate and sodium hydroxide. Fixation was allowed to proceed for 30 minutes at 4° C., after which the slides were washed in Dulbecco's PBS, treated with 3 μg/ml proteinase K (Sigma-Aldrich, St Louis, Mo.), acetylated with 1:400 acetic anhydride in 0.1M triethanolamine at pH 8.0, rinsed in 2×SSC and dehydrated through a series of alcohol baths. After drying the tissue for 2 hours in a vacuum dessicator at room temperature the hybridization solution (Simmons et al., 1989, *Journal of Histotechnology* 12(3):169-181) was applied. Glass coverslips were applied to the slides, air bubbles were removed and the outside of the slides was sealed with DPX mountant (Fluka, Milwaukee, Wis.) and the slides were incubated at 60° C. overnight. The cover slips were then removed in 4×SSC and the slides washed 4 times in 4×SSC baths. The slides were then treated with 20 μg/ml RNAse A (Sigma), rinsed and washed in baths of increasing stringency (0.5×SSC and 0.1×SSC). The stringency wash was 0.2×SSC with 50% formamide for 30 minutes at 65° C. Following the stringency wash the slides were washed in 0.1×SSC and dehydrated through an ethanol series. The slides were then dried in a vacuum dessicator and exposed to autoradiography film (Kodak Biomax MR, Rochester N.Y.) for 4 weeks, then processed using a Konica SRY-101A film processor (Konica Medical Corp., Wayne N.J.).

Receptor Autoradiography on Rat Brain Sections

Sections were thawed and dried under a cold air stream and then pre-incubated for 15 min. at room temperature in incubation buffer (20 mM HEPES, pH 7.4, 120 mM NaCl$_2$, 0.22 mM KH$_2$PO$_4$, 1.3 mM CaCl$_2$, 0.8 mM MgSO$_4$) by immersing sections in a 400 ml jar. Sections were dried again under a cold air stream and incubated for 60 min. with 7 pM [$^{125}$I]-R3/I5 (specific activity, 2200 Ci/mmole) in incubation buffer containing 0.5% BSA and protease inhibitor cocktail. Inhibition of [$^{125}$I]-R3/I5 binding sites by human R3 or relaxin were performed in several brain regions (olfactory bulb, cortex and superior colliculus). Nonspecific binding was determined in the presence of 100 nM of human R3. After incubation, the excess radioligand was washed off by immersing the slides in the jar containing incubation buffer at 4° C. (3 times 10 min.) followed by a quick immersion in water. Sections were dried and exposed to Fujifilm Imaging plates (BAS-MS 2025) for 48 hrs. The imaging plates were scanned using the Fuji Bio-Imaging Analyzer System (BAS-5000, Fuji Medical System, CT) and visualized using ImageGauge V3.12 software (Fuji Medical System, CT).

Cresyl-violet staining was performed on adjacent sections and the regions were identified using the rat brain atlas of Paxinos and Watson (Paxinos et al., 1998, *The Rat Brain in Stereotaxic Coordinates*, New York, Academic Press (publisher)). For illustration purposes, sections were exposed to autoradiography film ((Kodak Omat AR, Rochester N.Y.). After a 4-week exposure, they were automatically developed and fixed in a Konica SRY-101A machine (Konica Medical Corp., Wayne N.J.). Adobe Photoshop 7.0 and Illustrator 9.0 were used for preparation of the figures.

Sigmoidal competition binding curves were fitted by non-linear regression analysis using GraphPad Prism software (GraphPad Prism Software, San Diego, Calif.). The IC$_{50}$ values were derived from the curve calculation. The IC$_{50}$ is the concentration producing 50% inhibition of specific radioligand binding.

Results

Radioligand Competition Binding Analysis of Recombinant Rat GPCR135 and LGR7 Receptors Competition binding experiments were on membrane preparations of recombinant rat GPCR135 and LGR7 receptors to compare the affinities of R3/I5 for these 2 receptors using [$^{125}$I]-relaxin-3 (R3) and [$^{125}$I]relaxin-2 (R2) as tracers (FIGS. 7A and 7B, respectively). R3/I5 was found to be 800 fold selective for the rat GPCR135 (IC$_{50}$=0.5 nM) over the rat LGR7 (IC$_{50}$>400 nM). Relaxin displayed only weak affinity for [$^{125}$I]R3 binding sites in cells expressing rat GPCR135 receptors (IC$_{50}$>1 μM) but potently competed for [$^{125}$I]R2 binding in cells expressing rat LGR7 receptors (IC$_{50}$=200 pM).

Pharmacological Characterization of [$^{125}$I]-R3/I5 binding Sites on Rat Brain Sections Rat brain slides were incubated with 7 pM [$^{125}$I]-R3/I5 FIG. 8A). Pharmacological characterization of these binding sites was performed in several brain regions where high binding densities were observed (i.e. olfactory bulb, cortex, and superior colliculus) by measuring the potency of R3 or relaxin to inhibit specific [$^{125}$I]-R3/I5 binding. Representative images at the level of the superior colliculus in the presence of 10 nM of R3 or 100 nM relaxin-1 are shown in FIGS. 8B and 8C, respectively.

The corresponding competition binding curve is shown in FIG. 9. Affinities (IC$_{50}$ values) of R3 for [$^{125}$I]-R3/I5 binding sites in various brain regions are given in Table 3. Starting at low concentration, R3 displaced all the [$^{125}$I]-R3/I5 binding sites in all regions investigated. Full displacement of [$^{125}$I]-R3/I5 binding sites by R3 was observed at 10 nM (FIGS. 8A and 8B). IC$_{50}$ values ranged from 0.3 to 0.4 nM (Table 3). Hill slope values were not statistically different from unity.

In contrast to relaxin-3, in all the regions investigated, relaxin did not displace any significant amount of [$^{125}$I]-R3/I5 binding sites at concentrations of up to 100 nM (FIG. 8C).

Figure 10:
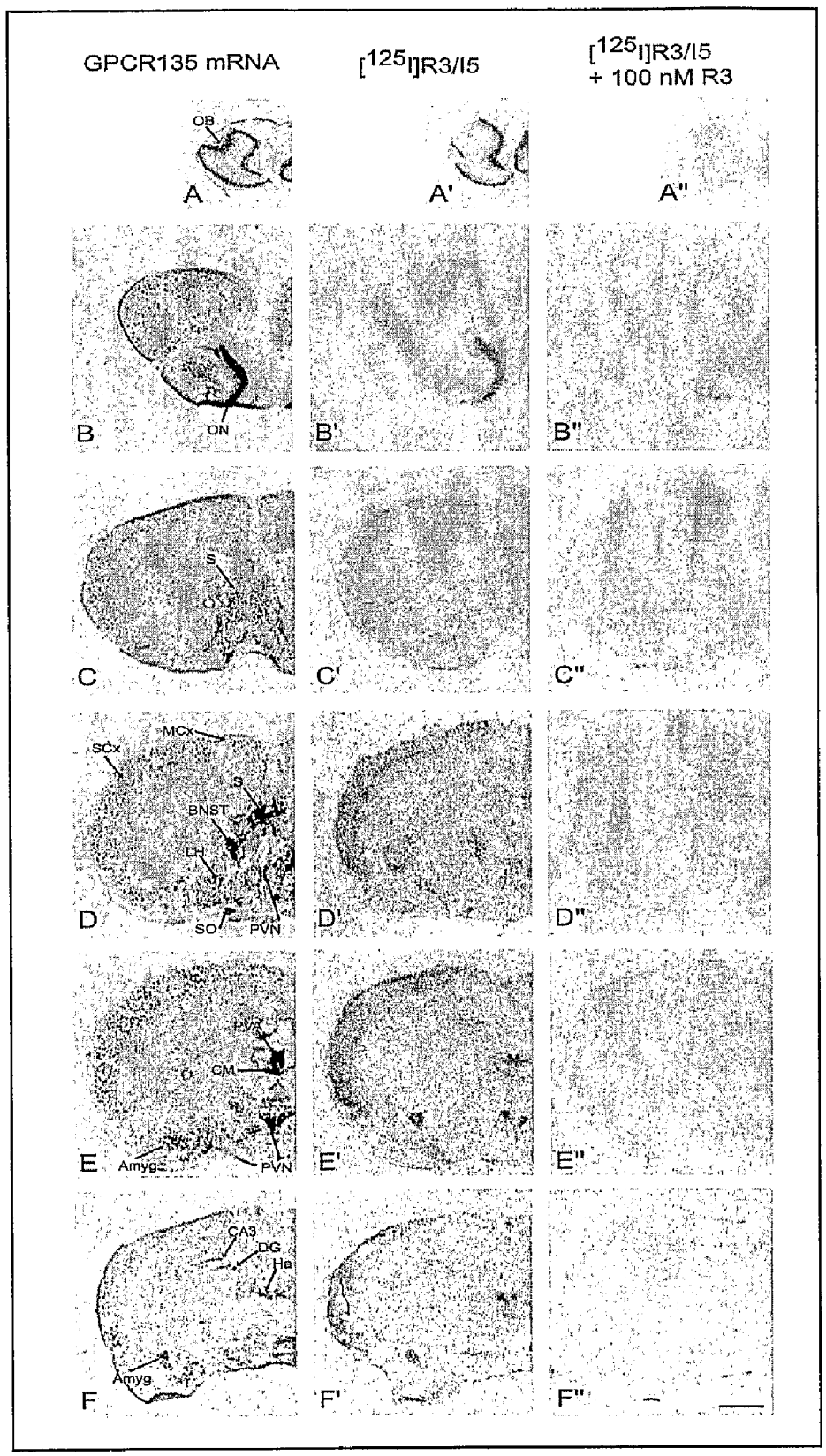

Anatomical Localization of GPCR135 mRNA and [$^{125}$I]R3/I5 Binding Sites in Rat Brain The anatomical distribution of GPCR135 mRNA receptor and [$^{125}$I]R3/I5 (7 pM) binding sites was studied in detail throughout the rat brain using in situ hybridization and receptor autoradiography on adjacent coronal sections. In general, the distribution pattern of GPCR135 mRNA receptor overlaps with the distribution of [$^{125}$I]R3/I5 binding sites. A semi-quantitative overview is presented in Table 4. Autoradiograms showing the rostrocaudal distribution of GPCR135 mRNA and [$^{125}$I]R3/I5 binding sites are shown in FIG. 10 (front and mid brain) and FIG. 11 (hind brain). Incubation with the sense probe did not yield any hybridization signal. Non-specific binding was defined in the presence of 100 nM R3 and was found to be low (FIGS. 10A" to 10F" and 11A" to 11F").

Specific hybridization signals and binding sites were restricted to distinct areas of the brain, including the olfactory system, septum, cortex, habenula, hypothalamus, amygdala, thalamus, hippocampal formation and several brain stem regions.

High densities of both mRNA and receptor binding sites were observed in the olfactory bulb (FIG. 10A, 10A') and olfactory nucleus (FIG. 10B, 10B'). In the septum (lateral part), moderate densities of mRNA were detected whereas only very low levels of binding sites were detectable (FIG. 10C, 10C'). Within the hypothalamus, mRNA and binding sites were restricted to the paraventricular nucleus (FIG. 10D, 10D', 10E, 10E') and supraoptic nucleus (FIG. 10D, 10D'). In addition, GPCR135 mRNA was detected in lateral hypothalamus (FIG. 10D). In the latter region, only low densities of binding sites were detectable (FIG. 10D').

Moderate to high densities of both GPCR135 mRNA and binding sites were detected in the thalamus, mainly in the paraventricular nucleus and centro medial nucleus (FIG. 10E, 10E'). Within the hippocampal formation, GPCR135 mRNA labeling was restricted to the CA3 field and dentate gyrus (FIG. 10F). Only low densities of binding sites were detectable in these hippocampal regions (FIG. 10F). In the habenula, moderate to high densities of both hybridization signal and binding sites were detected (FIG. 10F, 10F').

GPCR135 mRNA and binding sites were also present in the amygdala, with dense labeling the medial, central, lateral nuclei (FIG. 10E, 10E', 10F, 10F') and within the bed nucleus of the stria terminalis (FIG. 10D, 10D'). Strong labeling of both mRNA and binding sites was also observed in the amygdalohippocampal area (FIG. 11A, 11A').

Strong labeling of both GPCR135 mRNA and binding sites was observed in the superior colliculus (FIG. 11A, 11A', 11B, 11B') and interpeduncular nucleus (FIG. 11B, 11B').

Within the dorsal part of the dorsal raphe, periaqueductal gray area and inferior colliculus, moderate to low densities of GPCR135 mRNA and binding sites were detected (FIG. 11C, 11C', 11D, 11D').

Figure 11:
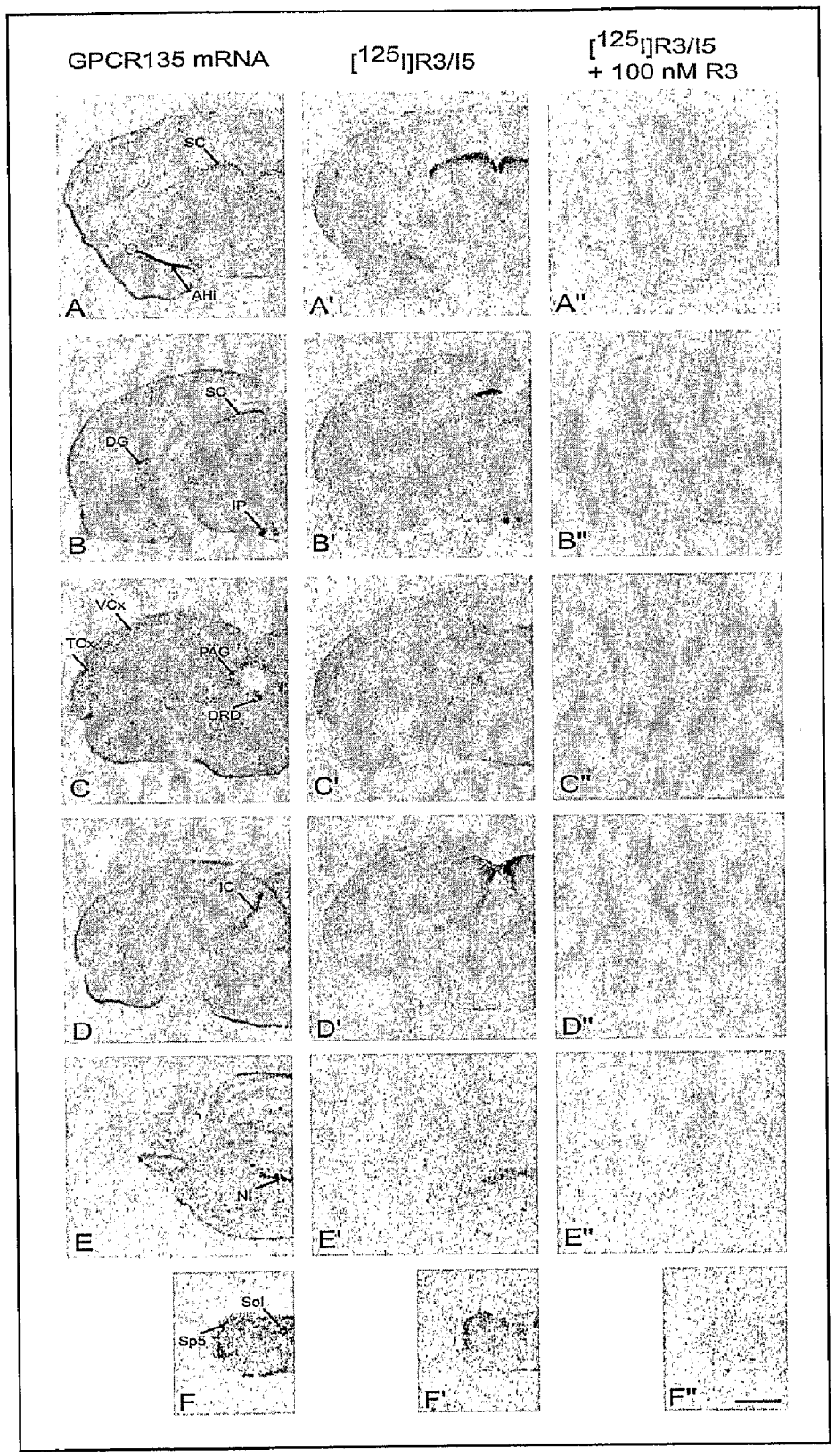

Through the cortical mantle higher densities of binding sites of GPCR135 were observed compared to the mRNA levels (FIGS. 10 and 11). Moderate densities of binding sites were observed in motor (FIG. 10D'), somatosensory (FIG. 10D'), temporal and visual (FIG. 11C') cortices.

Finally, both GPCR135 mRNA and binding sites were found in the nucleus incertus (FIG. 11E, 11E'), spinal trigeminal tract and nucleus of solitary tract (FIG. 11F, 11F').

TABLE 3

Potency of R3 (IC$_{50}$, mean ± S.E.M., n = 3) for inhibition of [$^{125}$I]R3/I5 binding sites in several rat brain regions measured using quantitative receptor autoradiography.

| | [$^{125}$I]R3/I5 |
|---|---|
| Olfactory bulb | 0.3 ± 0.1 |
| Cortex | 0.4 ± 0.2 |
| Superior colliculus | 0.3 ± 0.1 |

TABLE 4

Distribution of GPCR135 mRNA and [$^{125}$I]R3/I5 binding sites in rat brain (adjacent sections) determined using in situ hybridization and receptor autoradiography.

| | GPCR135 mRNA | [$^{125}$I]R3/I5 |
|---|---|---|
| Olfactory System | | |
| Olfactory bulb | +++ | +++ |
| Anterior olfactory nucleus | +++ | +++ |
| Septal region | | |
| Lateral | ++ | + |
| Cortex | | |
| Motor | + | ++ |
| Somatosensory | + | ++ |
| Piriform | + | ++ |
| Temporal | + | ++ |
| Visual | + | ++ |
| Habenula | | |
| Medial | ++ | ++ |
| Hypothalamus | | |
| Paraventricular nucleus | +++ | ++ |
| Supraoptic nucleus | +++ | ++ |
| Lateral nucleus | ++ | − |
| Amygdaloid body | | |
| Central nucleus | ++ | ++ |
| Lateral nucleus | ++ | ++ |
| Medial nucleus | ++ | ++ |
| Amygdalohippocampal area | +++ | +++ |
| Bed nucleus stria terminalis | ++ | ++ |
| Thalamus | | |
| Paraventricular | ++ | ++ |
| Centro medial | ++ | ++ |
| Centro lateral | ++ | ++ |
| Hippocampal formation | | |
| CAB field | ++ | + |
| Dentate gyrus | ++ | + |
| Brain stem | | |
| Superior colliculus | +++ | +++ |
| Inferior colliculus | ++ | ++ |
| Interpeduncular nucleus | +++ | +++ |
| Dorsal raphe, dorsal part | ++ | + |
| Periaqueductal gray area | ++ | ++ |

TABLE 4-continued

Distribution of GPCR135 mRNA and [$^{125}$I]R3/I5 binding sites in rat brain (adjacent sections) determined using in situ hybridization and receptor autoradiography.

|  | GPCR135 mRNA | [$^{125}$I]R3/I5 |
|---|---|---|
| Nucleus incertus | ++ | ++ |
| Spinal trigeminal tract | + | ++ |

Semi-quantitative values are given:
− not detected,
+ low density,
++ moderate density,
+++ high density (n = 3).

Discussion of Results of Example 6

Radiolabeling of the R3/I5 chimera yielded a tracer that was important to successful binding autoradiography studies. Initial efforts to map GPCR135 binding sites with [$^{125}$I]-R3 were unsuccessful because R3 is essentially uncharged and hydrophobic. The level of non-specific binding attainable with [$^{125}$I]-R3 is sufficient for work with recombinant receptor systems; however the [$^{125}$I]-R3 tracer was unamenable to workable conditions for autoradiographic binding studies. Substituting the A chain of insulin 5 in the R3 molecule imposes a net charge and reduces non-specific binding of the radioiodinated R3/I5 chimera (FIG. 11).

GPCR135 binding sites in the rat central nervous system were selectively identified after binding of [$^{125}$I]-R3/I5 (at a concentration of 7 pM). [$^{125}$I]-R3/I5 binding was fully displaced by 10 nM R3, but not by 100 nM relaxin, consistent with the pharmacology of GPCR135 (FIGS. 8A, 8B, and 8C and Table 3). In the rat, the only receptor other than GPCR135 that is known to bind R3 is LGR7. However, LGR7 lacks significant affinity for R3/I5 (FIG. 3C and 7B). Since GPCR142 is a pseudogene in the rat, the only known receptor able to yield the observed binding pattern is GPCR135.

The data show that the GPCR135 receptor density is most prominent in areas known for processing of sensory signals such as the olfactory bulb, sensory cortex, amygdala, thalamus, spinal trigeminal tract, inferior and superior colliculus. The level of mRNA expression observed was generally consistent in location and relative intensity with [$^{125}$I]-R3/I5 receptor binding autoradiography results. There were exceptions where GPCR135 mRNA expression was greater (i.e. the lateral septum, CA3 field and dentate gyrus) or less (i.e. cerebral cortical areas) than would be expected based on the binding autoradiography data; however the relative intensity of binding sites and expression were similar to each other.

A comparison of the results for R3/I5 binding to GPCR135 can be made with relaxin binding to LGR7 and LGR8 (Osheroff et al., 1991, *Prot. Natl. Acad. Sci. USA,* 88(15):6413-6417) to gain insights into signaling in this system. Since R3 originates almost exclusively from the nucleus incertus (with slight expression in the dentate gyrus of the hippocampus (Burazin, et al., 2002, *J. Neurochem.,* 28:1553-1557; Liu et al., 2003, *J. Biol. Chem.,* 278:50754-50764; and Liu et al., 2003, *J. Biol. Chem.,* 278:50765-50770) and pathways of the nucleus incertus are well described (Goto et al., 2001, *J. Comp. Neurol.,* 438(1):86-122), the analysis can be extended to help identify which receptors (LGR7 versus GPCR135) in which brain areas respond to R3.

Many areas of GPCR135 expression and GPCR135-like receptor binding also bind relaxin (Osheroff et al., 1991, *Prot. Natl. Acad. Sci. USA,* 88(15):6413-6417). Use of a relaxin tracer should label LGR7 and LGR8 receptors, which are found in the brain and share a high affinity for relaxin (Hsu, 2003, *Trends Endocrinol. Metab.,* 14(7):303-309; Hsu et al., 2003, *Mol. Cell. Endocrinol.,* 202:165-170; and Hsu et al., 2002, *Science,* 295:671-674). Examples of areas apparently bearing both GPCR135 (as visualized with the specific tracers disclosed herein) and LGR7/8 (as shown with labeled relaxin (Osheroff et al., 1991, *Prot. Natl. Acad. Sci. USA,* 88(15):6413-6417) include the olfactory bulbs, anterior olfactory nucleus, paraventricular hypothalamic nucleus, supraoptic nucleus, thalamic nuclei (paraventricular and centromedial), the dentate gyrus of the hippocampus and the interpeduncular nucleus. GPCR135 expression and I5/R3 binding are found in the nucleus incertus, while relaxin binding is found in the dorsal tegmental nucleus. Dorsal tegmental relaxin binding observed by Osheroff and Phillips appears to be lateral to the GPCR135 expression/R3/I5 binding. Thus, R3/I5 binding sites and relaxin binding sites appear to be of sufficient proximity to allow paracrine, if not direct, communication.

Sites of R3/I5 binding in the CNS, which are similar to areas of GPCR135 expression, are found in a number of areas lacking affinity for relaxin (Osheroff et al., 1991, *Prot. Natl. Acad. Sci. USA,* 88(15):6413-6417). Selective GPCR135 expression and I5/R3 binding can be seen in the lateral septum, habenula, the superior colliculus and inferior colliculus. Expression of GPCR135 mRNA and I5/R3 binding sites in the amygdala appear to be more extensive than has been observed for relaxin binding sites, as GPCR135 sites/mRNA cover the central, medial, and lateral amygdalar nuclei as well as the bed nucleus of the stria terminalis. The GPCR135 coverage of the amygdala is so complete as to create a semicircle surrounding the ventrolateral zones of the thalamus. GPCR135 mRNA and I5/R3 binding sites are also found in the CA3 field of the hippocampus, where relaxin binding is lacking (Osheroff et al., 1991, *Prot. Natl. Acad. Sci. USA,* 88(15):6413-6417).

Osheroff and Phillips found areas of relaxin binding where neither GPCR135 expression nor GPCR135-like binding was detected. The organum vasculosum of the lamina terminalis, subfornical organ, arcuate hypothalamic nucleus, mammillary peduncle, anterior pretectal nucleus and the posterior hypothalamus all bind relaxin, but lack indications of GPCR135.

Areas where GPCR135 mRNA and GPCR135-like binding sites are detected share a common feature of involvement in sensory perception. For instance, the olfactory bulbs and olfactory nuclei, which showed signals for GPCR135 mRNA and GPCR135 binding sites, are early relays in the transmission of olfactory signals. Similarly, GPCR135 mRNA and binding sites were detected in the visual and somatosensory cortex, where sensory information is processed or integrated for movement.

GPCR135 mRNA and I5/R3 binding sites were found in some sensory areas of the brain lacking relaxin binding sites (Osheroff et al., 1991, *Prot. Natl. Acad. Sci. USA,* 88(15):6413-6417). The superior colliculus, which bound R3/I5, is known for its involvement in visual attention and saccadic eye movements. Aural inputs pass through the inferior colliculus, which expresses GPCR135 mRNA and displays I5/R3 binding sites, on the way to the medial geniculate nucleus and the primary auditory cortex. Expression of GPCR135 mRNA and GPCR135-like binding sites were also detected in the lateral septum, which is involved in the processing of tactile stimuli (Adams, 2000, *Brain Research,* 858(1):177-180).

GPCR135 expression and I5/R3 binding in these areas suggest role(s) in the three key senses (visual, auditory and tactile). Notably, the superior colliculus, which displays particularly strong GPCR135-like receptor binding, has been linked to sensory and motor functions involving these 3 senses [King, 2004, *Curr. Biol.*, 14(9):R335-R338)].

Pathway tracing studies have mapped afferent and efferent projections of the nucleus incertus (Goto et al., 2001, *J. Comp. Neurol.*, 438(1):86-122), which is the predominant source of R3 in the CNS. Comparing the results herein (Liu et al., 2003, *J. Biol. Chem.*, 278:50754-50764 and Liu et al., 2003, *J. Biol. Chem.*, 278:50765-50770) to those of Goto et al. (Goto et al., 2001, *J. Comp. Neurol.*, 438(1):86-122), R3 expressing cells are found in the nucleus incertus (NI) and in the adjacent central gray. The NI projects to a number of brain nuclei that express GPCR135 and have GPCR135-like binding sites. Ascending NI fibers pass through the interpeduncular nucleus, which expresses GPCR135 mRNA and has a significant concentration of binding sites. NI fibers passing through the interpeduncular nucleus project further to the thalamus, which also shows pronounced GPCR135 mRNA expression and I5/R3 binding. Some NI fibers also project to the hypothalamus, where we show binding sites and mRNA expression. A sparse NI projection reaches the superior colliculus, which shows a high density of binding sites and strong GPCR135 mRNA expression. NI projections are also found in the amygdala, the supraoptic nucleus, dorsal raphe, medial habenula and cortical fields, all of which express GPCR135 mRNA and show binding sites. NI neurons project to the temporal pole of the dentate gyrus, which has been shown to exhibit light expression of R3 (Burazin et al., 2002, *J. Neurochem*, 82:1553-1557), weakly expresses of GPCR135 mRNA and has I5/R3 binding sites. In summary, nucleus incertus projections identified by Goto et al (Goto et al., 2001, *J. Comp. Neurol.*, 438(1):86-122), are generally consistent with our observations of GPCR135-like sites and mRNA.

As the primary source of R3 in the CNS, the NI is positioned to be central to physiological functions modulated by R3 and GPCR135. In addition to expressing R3, the NI strongly expresses RNA for the type 1 CRF receptor (Potter et al., 1994, *Prot. Natl. Acad. Sci. USA*, 91:8777-8781). A number of areas that express GPCR135 such as the olfactory bulb, dentate gyrus, amygdala, superior colliculus, inferior colliculus, dorsal raphe, and solitary tract also express CRF-R1 and/or CRF-R2 mRNA (Potter et al., 1994, *Prot. Natl. Acad. Sci. USA*, 91:8777-8781; Chalmers et al., 1995, *J. Neurosci.*, 15(10):6340-6350 and Van Pett, 2000, *J. Comp. Neur.*, 428: 191-212) GPCR135 mRNA expression and GPCR135-like binding sites are prominent in areas related to sensory processing, integration and motor control. It is believed that the NI is involved in extrapituitary actions of CRF (Goto et al., 2001, *J. Comp. Neurol.*, 438(1):86-122). Considering these factors, the NI may well be involved in regulating sensory perception and sensory-motor reflexes under stressful conditions.

Although various advantages and aspects of the invention have been illustrated above by reference to examples and preferred embodiments, it will be appreciated that the scope of the invention is defined not by the foregoing description, but by the following claims as properly construed under principles of patent law.

What is claimed is:

1. A biologically active relaxin-3 chimeric polypeptide comprising the relaxin-3 B-chain having the amino acid sequence as set forth in SEQ ID NO: 89 and the insulin-like 5 A-chain having the amino acid sequence as set forth in SEQ ID NO: 95, the polypeptide having the amino acid sequence as set forth in SEQ ID NO:23.

2. A pre-propolypeptide comprising the amino acid sequence as set forth in SEQ ID NO:15.

SEQUENCE LISTING

<160> NUMBER OF SEQ ID NOS: 98

<210> SEQ ID NO 1
<211> LENGTH: 447
<212> TYPE: DNA
<213> ORGANISM: Artificial
<220> FEATURE:
<223> OTHER INFORMATION: Human Relaxin-3/Random A chimeric
      prepropolypeptide cDNA

<400> SEQUENCE: 1
atgctgaccg cagcgttgct gagctgtgcc ctgctgctgg cactgcctgc cacgcgagga      60
gactacaagg acgacgatga caaggaattc gatgacgacg ataagcgggc agcgccttac     120
ggggtcaggc tttgcggccg agaattcatc cgagcagtca tcttcacctg cgggggctcc     180
cggtggagac gatcagacat cctggcccac gaggctatgg gagataccttt cccggatgca     240 gatgctgatg aagacagtct ggcaggcgag ctggatgagg ccatggggtc cagcgagtgg     300
ctggccctga ccaagtcacc ccaggccttt tacaggggggc gacccagctg gcaaggaacc     360
cctggggttc ttcggggccg acgaggcctg tacgagaact gctgcctgtc catctgcgac     420
gactacgaga tcgagaaggc ctgctga                                          447

<210> SEQ ID NO 2
<211> LENGTH: 447
<212> TYPE: DNA
<213> ORGANISM: Artificial
<220> FEATURE:
<223> OTHER INFORMATION: Human Relaxin-3/Insulin chimeric
      prepropolypeptide cDNA

<400> SEQUENCE: 2

```
atgctgaccg cagcgttgct gagctgtgcc ctgctgctgg cactgcctgc cacgcgagga      60
gactacaagg acgacgatga caaggaattc gatgacgacg ataagcgggc agcgccttac     120
ggggtcaggc tttgcggccg agaattcatc cgagcagtca tcttcacctg cggggggctcc   180 cggtggagac gatcagacat cctggcccac gaggctatgg agatacctt cccggatgca     240 gatgctgatg aagacagtct ggcaggcgag ctggatgagg ccatggggtc agcgagtgg     300 ctggccctga ccaagtcacc ccaggccttt tacaggggc gacccagctg gcaaggaacc     360
cctggggttc ttcggggccg acgaggcatc gtggagcagt gctgcaccctc catctgctcc   420 ctgtaccagc tggagaacta ctgctga                                        447
```

<210> SEQ ID NO 3
<211> LENGTH: 459
<212> TYPE: DNA
<213> ORGANISM: Artificial
<220> FEATURE:
<223> OTHER INFORMATION: Human Relaxin-3/Relaxin-1 chimeric
prepropolypeptide cDNA

<400> SEQUENCE: 3

```
atgctgaccg cagcgttgct gagctgtgcc ctgctgctgg cactgcctgc cacgcgagga      60
gactacaagg acgacgatga caaggaattc gatgacgacg ataagcgggc agcgccttac     120
ggggtcaggc tttgcggccg agaattcatc cgagcagtca tcttcacctg cggggggctcc   180 cggtggagac gatcagacat cctggcccac gaggctatgg agatacctt cccggatgca     240 gatgctgatg aagacagtct ggcaggcgag ctggatgagg ccatggggtc agcgagtgg     300 ctggccctga ccaagtcacc ccaggccttt tacaggggc gacccagctg gcaaggaacc     360
cctggggttc ttcggggccg acgacgaccc tacgtggcac tgtttgagaa atgttgccta    420
attggttgta ccaaaaggtc tcttgctaaa tattgctga                           459
```

<210> SEQ ID NO 4
<211> LENGTH: 459
<212> TYPE: DNA
<213> ORGANISM: Artificial
<220> FEATURE:
<223> OTHER INFORMATION: Human Relaxin-3/Relaxin-2 chimeric
prepropolypeptide cDNA

<400> SEQUENCE: 4

```
atgctgaccg cagcgttgct gagctgtgcc ctgctgctgg cactgcctgc cacgcgagga      60
gactacaagg acgacgatga caaggaattc gatgacgacg ataagcgggc agcgccttac     120
ggggtcaggc tttgcggccg agaattcatc cgagcagtca tcttcacctg cggggggctcc   180 cggtggagac gatcagacat cctggcccac gaggctatgg agatacctt cccggatgca     240 gatgctgatg aagacagtct ggcaggcgag ctggatgagg ccatggggtc agcgagtgg     300 ctggccctga ccaagtcacc ccaggccttt tacaggggc gacccagctg gcaaggaacc     360
cctggggttc ttcggggccg acgacaactc tacagtgcat ggctaataa atgttgccat     420 gttggttgta ccaaaagatc tcttgctaga ttttgctga                           459
```

<210> SEQ ID NO 5
<211> LENGTH: 447
<212> TYPE: DNA
<213> ORGANISM: Artificial
<220> FEATURE:
<223> OTHER INFORMATION: Human Relaxin-3/Insulin-like 3 chimeric preptopolypeptide cDNA

<400> SEQUENCE: 5

| atgctgaccg cagcgttgct gagctgtgcc ctgctgctgg cactgcctgc cacgcgagga | 60 |
| gactacaagg acgacgatga caaggaattc gatgacgacg ataagcgggc agcgccttac | 120 |
| ggggtcaggc tttgcggccg agaattcatc cgagcagtca tcttcacctg cgggggctcc | 180 |
| cggtggagac gatcagacat cctggcccac gaggctatgg agataccctt cccggatgca | 240 |
| gatgctgatg aagacagtct ggcaggcgag ctggatgagg ccatggggtc agcgagtgg | 300 |
| ctggccctga ccaagtcacc ccaggccttt tacaggggc gacccagctg gcaaggaacc | 360 |
| cctggggttc ttcggggccg acgaaacccc gcccgctact gctgcctgtc cggctgcacc | 420 |
| cagcaggacc tgctgaccct gtgctga | 447 |

<210> SEQ ID NO 6
<211> LENGTH: 444
<212> TYPE: DNA
<213> ORGANISM: Artificial
<220> FEATURE:
<223> OTHER INFORMATION: Human Relaxin-3/Insulin-like 4 chimeric preptopolypeptide cDNA

<400> SEQUENCE: 6

| atgctgaccg cagcgttgct gagctgtgcc ctgctgctgg cactgcctgc cacgcgagga | 60 |
| gactacaagg acgacgatga caaggaattc gatgacgacg ataagcgggc agcgccttac | 120 |
| ggggtcaggc tttgcggccg agaattcatc cgagcagtca tcttcacctg cgggggctcc | 180 |
| cggtggagac gatcagacat cctggcccac gaggctatgg agataccctt cccggatgca | 240 |
| gatgctgatg aagacagtct ggcaggcgag ctggatgagg ccatggggtc agcgagtgg | 300 |
| ctggccctga ccaagtcacc ccaggccttt tacaggggc gacccagctg gcaaggaacc | 360 |
| cctggggttc ttcggggccg acgattcgac cccttctgct gcgaggtgat ctgcgacgac | 420 |
| ggcacctccg tgaagctgtg ctga | 444 |

<210> SEQ ID NO 7
<211> LENGTH: 450
<212> TYPE: DNA
<213> ORGANISM: Artificial
<220> FEATURE:
<223> OTHER INFORMATION: Human Relaxin-3/Insulin-like 5 chimeric preptopolypeptide cDNA

<400> SEQUENCE: 7

| atgctgaccg cagcgttgct gagctgtgcc ctgctgctgg cactgcctgc cacgcgagga | 60 |
| gactacaagg acgacgatga caaggaattc gatgacgacg ataagcgggc agcgccttac | 120 |
| ggggtcaggc tttgcggccg agaattcatc cgagcagtca tcttcacctg cgggggctcc | 180 |
| cggtggagac gatcagacat cctggcccac gaggctatgg agataccctt cccggatgca | 240 |
| gatgctgatg aagacagtct ggcaggcgag ctggatgagg ccatggggtc agcgagtgg | 300 |
| ctggccctga ccaagtcacc ccaggccttt tacaggggc gacccagctg gcaaggaacc | 360 |
| cctggggttc ttcggggccg acgacaagat ttacaaactt tgtgttgcac tgatggctgt | 420 |
| tccatgacta atttgagtgc tctttgctaa | 450 |

<210> SEQ ID NO 8
<211> LENGTH: 447
<212> TYPE: DNA
<213> ORGANISM: Artificial

<220> FEATURE:
<223> OTHER INFORMATION: Human Relaxin-3/Insulin-like 6 chimeric
     prepropolypeptide cDNA

<400> SEQUENCE: 8

| | | | | | |
|---|---|---|---|---|---|
| atgctgaccg | cagcgttgct | gagctgtgcc | ctgctgctgg | cactgcctgc | cacgcgagga | 60 |
| gactacaagg | acgacgatga | caaggaattc | gatgacgacg | ataagcgggc | agcgccttac | 120 |
| ggggtcaggc | tttgcggccg | agaattcatc | cgagcagtca | tcttcacctg | cggggggctcc | 180 |
| cggtggagac | gatcagacat | cctggcccac | gaggctatgg | gagataccttt | cccggatgca | 240 |
| gatgctgatg | aagacagtct | ggcaggcgag | ctggatgagg | ccatgggttc | cagcgagtgg | 300 |
| ctggccctga | ccaagtcacc | ccaggccttt | tacaggggggc | gacccagctg | gcaaggaacc | 360 |
| cctgggggttc | ttcggggccg | acgaggctac | tccgagaagt | gctgcctgac | cggctgcacc | 420 |
| aaggaggagc | tgtccatcgc | ctgctga | | | | 447 |

<210> SEQ ID NO 9
<211> LENGTH: 148
<212> TYPE: PRT
<213> ORGANISM: Artificial
<220> FEATURE:
<223> OTHER INFORMATION: Human Relaxin-3/Random A chimeric
     prepropolypeptide

<400> SEQUENCE: 9

Met Leu Thr Ala Ala Leu Leu Ser Cys Ala Leu Leu Leu Ala Leu Pro
1               5                   10                  15

Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
        35                  40                  45

Phe Ile Arg Ala Val Ile Phe Thr Cys Gly Gly Ser Arg Trp Arg Arg
    50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
        115                 120                 125

Gly Leu Tyr Glu Asn Cys Cys Leu Ser Ile Cys Asp Tyr Glu Ile
    130                 135                 140

Glu Lys Ala Cys
145

<210> SEQ ID NO 10
<211> LENGTH: 148
<212> TYPE: PRT
<213> ORGANISM: Artificial
<220> FEATURE:
<223> OTHER INFORMATION: Human Relaxin-3/Insulin chimeric
     prepropolypeptide

<400> SEQUENCE: 10

Met Leu Thr Ala Ala Leu Leu Ser Cys Ala Leu Leu Leu Ala Leu Pro
1               5                   10                  15

Ala Thr Arg Gly Asp Tyr Lys Asp Asp Asp Lys Glu Phe Asp Asp
            20                  25                  30

```
Asp Asp Lys Arg Ala Ala Pro Tyr Gly Val Arg Leu Cys Gly Arg Glu
            35                  40                  45

Phe Ile Arg Ala Val Ile Phe Thr Cys Gly Gly Ser Arg Trp Arg Arg
        50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
            115                 120                 125

Gly Ile Val Glu Gln Cys Cys Thr Ser Ile Cys Ser Leu Tyr Gln Leu
        130                 135                 140

Glu Asn Tyr Cys
145

<210> SEQ ID NO 11
<211> LENGTH: 152
<212> TYPE: PRT
<213> ORGANISM: Artificial
<220> FEATURE:
<223> OTHER INFORMATION: Human Relaxin-3/Relaxin-1 chimeric
      prepropolypeptide

<400> SEQUENCE: 11

Met Leu Thr Ala Ala Leu Leu Ser Cys Ala Leu Leu Ala Leu Pro
1               5                   10                  15

Ala Thr Arg Gly Asp Tyr Lys Asp Asp Asp Asp Lys Glu Phe Asp Asp
            20                  25                  30

Asp Asp Lys Arg Ala Ala Pro Tyr Gly Val Arg Leu Cys Gly Arg Glu
            35                  40                  45

Phe Ile Arg Ala Val Ile Phe Thr Cys Gly Gly Ser Arg Trp Arg Arg
        50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
            115                 120                 125

Arg Pro Tyr Val Ala Leu Phe Glu Lys Cys Cys Leu Ile Gly Cys Thr
        130                 135                 140

Lys Arg Ser Leu Ala Lys Tyr Cys
145                 150

<210> SEQ ID NO 12
<211> LENGTH: 152
<212> TYPE: PRT
<213> ORGANISM: Artificial
<220> FEATURE:
<223> OTHER INFORMATION: Human Relaxin-3/Relaxin-2 chimeric
      prepropolypeptide

<400> SEQUENCE: 12

Met Leu Thr Ala Ala Leu Leu Ser Cys Ala Leu Leu Ala Leu Pro
1               5                   10                  15
```

```
Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
        35                  40                  45

Phe Ile Arg Ala Val Ile Phe Thr Cys Gly Gly Ser Arg Trp Arg Arg
    50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
        115                 120                 125

Gln Leu Tyr Ser Ala Leu Ala Asn Lys Cys Cys His Val Gly Cys Thr
    130                 135                 140

Lys Arg Ser Leu Ala Arg Phe Cys
145                 150

<210> SEQ ID NO 13
<211> LENGTH: 148
<212> TYPE: PRT
<213> ORGANISM: Artificial
<220> FEATURE:
<223> OTHER INFORMATION: Human Relaxin-3/Insulin-like 3 chimeric
      prepropolypeptide

<400> SEQUENCE: 13

Met Leu Thr Ala Ala Leu Leu Ser Cys Ala Leu Leu Leu Ala Leu Pro
1               5                   10                  15

Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
        35                  40                  45

Phe Ile Arg Ala Val Ile Phe Thr Cys Gly Gly Ser Arg Trp Arg Arg
    50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
        115                 120                 125

Asn Pro Ala Arg Tyr Cys Cys Leu Ser Gly Cys Thr Gln Gln Asp Leu
    130                 135                 140

Leu Thr Leu Cys
145

<210> SEQ ID NO 14
<211> LENGTH: 147
<212> TYPE: PRT
<213> ORGANISM: Artificial
<220> FEATURE:
<223> OTHER INFORMATION: Human Relaxin-3/Insulin-like 4 chimeric
      prepropolypeptide

<400> SEQUENCE: 14
```

```
Met Leu Thr Ala Ala Leu Leu Ser Cys Ala Leu Leu Ala Leu Pro
1               5                   10                  15

Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
            35                  40                  45

Phe Ile Arg Ala Val Ile Phe Thr Cys Gly Gly Ser Arg Trp Arg Arg
        50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
                100                 105                 110

Gly Arg Pro Ser Trp Gln Gly Thr Pro Gly Val Leu Arg Gly Arg Arg
            115                 120                 125

Phe Asp Pro Phe Cys Cys Glu Val Ile Cys Asp Asp Gly Thr Ser Val
        130                 135                 140

Lys Leu Cys
145

<210> SEQ ID NO 15
<211> LENGTH: 149
<212> TYPE: PRT
<213> ORGANISM: Artificial
<220> FEATURE:
<223> OTHER INFORMATION: Human Relaxin-3/Insulin-like 5 chimeric
      prepropolypeptide

<400> SEQUENCE: 15

Met Leu Thr Ala Ala Leu Leu Ser Cys Ala Leu Leu Ala Leu Pro
1               5                   10                  15

Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
            35                  40                  45

Phe Ile Arg Ala Val Ile Phe Thr Cys Gly Gly Ser Arg Trp Arg Arg
        50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
                100                 105                 110

Gly Arg Pro Ser Trp Gln Gly Thr Pro Gly Val Leu Arg Gly Arg Arg
            115                 120                 125

Gln Asp Leu Gln Thr Leu Cys Cys Thr Asp Gly Cys Ser Met Thr Asp
        130                 135                 140

Leu Ser Ala Leu Cys
145

<210> SEQ ID NO 16
<211> LENGTH: 148
<212> TYPE: PRT
<213> ORGANISM: Artificial
<220> FEATURE:
<223> OTHER INFORMATION: Human Relaxin-3/Insulin-like 6 chimeric
``` prepropolypeptide

<400> SEQUENCE: 16

Met Leu Thr Ala Ala Leu Leu Ser Cys Ala Leu Leu Ala Leu Pro
1               5                   10                  15

Ala Thr Arg Gly Asp Tyr Lys Asp Asp Asp Lys Glu Phe Asp Asp
            20                  25                  30

Asp Asp Lys Arg Ala Ala Pro Tyr Gly Val Arg Leu Cys Gly Arg Glu
        35                  40                  45

Phe Ile Arg Ala Val Ile Phe Thr Cys Gly Gly Ser Arg Trp Arg Arg
50                  55                  60

Ser Asp Ile Leu Ala His Glu Ala Met Gly Asp Thr Phe Pro Asp Ala
65                  70                  75                  80

Asp Ala Asp Glu Asp Ser Leu Ala Gly Glu Leu Asp Glu Ala Met Gly
                85                  90                  95

Ser Ser Glu Trp Leu Ala Leu Thr Lys Ser Pro Gln Ala Phe Tyr Arg
            100                 105                 110

Gly Arg Pro Ser Trp Gln Gly Thr Pro Gly Val Leu Arg Gly Arg Arg
        115                 120                 125

Gly Tyr Ser Glu Lys Cys Cys Leu Thr Gly Cys Thr Lys Glu Glu Leu
130                 135                 140

Ser Ile Ala Cys
145

<210> SEQ ID NO 17
<211> LENGTH: 47
<212> TYPE: PRT
<213> ORGANISM: Artificial
<220> FEATURE:
<223> OTHER INFORMATION: Human Relaxin-3/Random A chimeric mature
      polypeptide

<400> SEQUENCE: 17

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp Gly Leu Tyr Glu Asn
            20                  25                  30

Cys Cys Leu Ser Ile Cys Asp Asp Tyr Glu Ile Glu Lys Ala Cys
        35                  40                  45

<210> SEQ ID NO 18
<211> LENGTH: 47
<212> TYPE: PRT
<213> ORGANISM: Artificial
<220> FEATURE:
<223> OTHER INFORMATION: Human Relaxin-3/Insulin chimeric mature
      polypeptide

<400> SEQUENCE: 18

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp Gly Ile Val Glu Gln
            20                  25                  30

Cys Cys Thr Ser Ile Cys Ser Leu Tyr Gln Leu Glu Asn Tyr Cys
        35                  40                  45

<210> SEQ ID NO 19
<211> LENGTH: 50
<212> TYPE: PRT
<213> ORGANISM: Artificial

```
<220> FEATURE:
<223> OTHER INFORMATION: Human Relaxin-3/Relaxin-1 chimeric mature
      polypeptide

<400> SEQUENCE: 19

Arg Ala Ala Pro Tyr Gly Val Arg Leu Cys Gly Arg Glu Phe Ile Arg
1               5                  10                  15

Ala Val Ile Phe Thr Cys Gly Gly Ser Arg Trp Pro Tyr Val Ala Leu
            20                  25                  30

Phe Glu Lys Cys Cys Leu Ile Gly Cys Thr Lys Arg Ser Leu Ala Lys
        35                  40                  45

Tyr Cys
    50

<210> SEQ ID NO 20
<211> LENGTH: 51
<212> TYPE: PRT
<213> ORGANISM: Artificial
<220> FEATURE:
<223> OTHER INFORMATION: Human Relaxin-3/Relaixin-2 chimeric mature
      polypeptide

<400> SEQUENCE: 20

Arg Ala Ala Pro Tyr Gly Val Arg Leu Cys Gly Arg Glu Phe Ile Arg
1               5                  10                  15

Ala Val Ile Phe Thr Cys Gly Gly Ser Arg Trp Gln Leu Tyr Ser Ala
            20                  25                  30

Leu Ala Asn Lys Cys Cys His Val Gly Cys Thr Lys Arg Ser Leu Ala
        35                  40                  45

Arg Phe Cys
    50

<210> SEQ ID NO 21
<211> LENGTH: 47
<212> TYPE: PRT
<213> ORGANISM: Artificial
<220> FEATURE:
<223> OTHER INFORMATION: Human Relaxin-3/Insulin-like 3 chimeric mature
      polypeptide

<400> SEQUENCE: 21

Arg Ala Ala Pro Tyr Gly Val Arg Leu Cys Gly Arg Glu Phe Ile Arg
1               5                  10                  15

Ala Val Ile Phe Thr Cys Gly Gly Ser Arg Trp Asn Pro Ala Arg Tyr
            20                  25                  30

Cys Cys Leu Ser Gly Cys Thr Gln Gln Asp Leu Leu Thr Leu Cys
        35                  40                  45

<210> SEQ ID NO 22
<211> LENGTH: 46
<212> TYPE: PRT
<213> ORGANISM: Artificial
<220> FEATURE:
<223> OTHER INFORMATION: Human Relaxin-3/Insulin-like 4 chimeric mature
      polypeptide

<400> SEQUENCE: 22

Arg Ala Ala Pro Tyr Gly Val Arg Leu Cys Gly Arg Glu Phe Ile Arg
1               5                  10                  15

Ala Val Ile Phe Thr Cys Gly Gly Ser Arg Trp Phe Asp Pro Phe Cys
            20                  25                  30

Cys Glu Val Ile Cys Asp Asp Gly Thr Ser Val Lys Leu Cys
```

<210> SEQ ID NO 23
<211> LENGTH: 48
<212> TYPE: PRT
<213> ORGANISM: Artificial
<220> FEATURE:
<223> OTHER INFORMATION: Human Relaxin-3/Insulin-like 5 chimeric mature
      polypeptide

<400> SEQUENCE: 23

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp Gln Asp Leu Gln Thr
            20                  25                  30

Leu Cys Cys Thr Asp Gly Cys Ser Met Thr Asp Leu Ser Ala Leu Cys
        35                  40                  45

<210> SEQ ID NO 24
<211> LENGTH: 47
<212> TYPE: PRT
<213> ORGANISM: Artificial
<220> FEATURE:
<223> OTHER INFORMATION: Human Relaxin-3/Insulin-like 6 chimeric mature
      polypeptide

<400> SEQUENCE: 24

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp Gly Tyr Ser Glu Lys
            20                  25                  30

Cys Cys Leu Thr Gly Cys Thr Lys Glu Glu Leu Ser Ile Ala Cys
        35                  40                  45

<210> SEQ ID NO 25
<211> LENGTH: 469
<212> TYPE: PRT
<213> ORGANISM: Homo sapiens

<400> SEQUENCE: 25

Met Gln Met Ala Asp Ala Ala Thr Ile Ala Thr Met Asn Lys Ala Ala
1               5                   10                  15

Gly Gly Asp Lys Leu Ala Glu Leu Phe Ser Leu Val Pro Asp Leu Leu
            20                  25                  30

Glu Ala Ala Asn Thr Ser Gly Asn Ala Ser Leu Gln Leu Pro Asp Leu
        35                  40                  45

Trp Trp Glu Leu Gly Leu Glu Leu Pro Asp Gly Ala Pro Pro Gly His
    50                  55                  60

Pro Pro Gly Ser Gly Gly Ala Glu Ser Ala Asp Thr Glu Ala Arg Val
65                  70                  75                  80

Arg Ile Leu Ile Ser Val Val Tyr Trp Val Val Cys Ala Leu Gly Leu
                85                  90                  95

Ala Gly Asn Leu Leu Val Leu Tyr Leu Met Lys Ser Met Gln Gly Trp
            100                 105                 110

Arg Lys Ser Ser Ile Asn Leu Phe Val Thr Asn Leu Ala Leu Thr Asp
        115                 120                 125

Phe Gln Phe Val Leu Thr Leu Pro Phe Trp Ala Val Glu Asn Ala Leu
    130                 135                 140

Asp Phe Lys Trp Pro Phe Gly Lys Ala Met Cys Lys Ile Val Ser Met
145                 150                 155                 160

```
Val Thr Ser Met Asn Met Tyr Ala Ser Val Phe Phe Leu Thr Ala Met
            165                 170                 175

Ser Val Thr Arg Tyr His Ser Val Ala Ser Ala Leu Lys Ser His Arg
        180                 185                 190

Thr Arg Gly His Gly Arg Gly Asp Cys Cys Gly Arg Ser Leu Gly Asp
    195                 200                 205

Ser Cys Cys Phe Ser Ala Lys Ala Leu Cys Val Trp Ile Trp Ala Leu
    210                 215                 220

Ala Ala Leu Ala Ser Leu Pro Ser Ala Ile Phe Ser Thr Thr Val Lys
225                 230                 235                 240

Val Met Gly Glu Glu Leu Cys Leu Val Arg Phe Pro Asp Lys Leu Leu
            245                 250                 255

Gly Arg Asp Arg Gln Phe Trp Leu Gly Leu Tyr His Ser Gln Lys Val
        260                 265                 270

Leu Leu Gly Phe Val Leu Pro Leu Gly Ile Ile Leu Cys Tyr Leu
    275                 280                 285

Leu Leu Val Arg Phe Ile Ala Asp Arg Arg Ala Ala Gly Thr Lys Gly
    290                 295                 300

Gly Ala Ala Val Ala Gly Gly Arg Pro Thr Gly Ala Ser Ala Arg Arg
305                 310                 315                 320

Leu Ser Lys Val Thr Lys Ser Val Thr Ile Val Val Leu Ser Phe Phe
            325                 330                 335

Leu Cys Trp Leu Pro Asn Gln Ala Leu Thr Thr Trp Ser Ile Leu Ile
        340                 345                 350

Lys Phe Asn Ala Val Pro Phe Ser Gln Glu Tyr Phe Leu Cys Gln Val
        355                 360                 365

Tyr Ala Phe Pro Val Ser Val Cys Leu Ala His Ser Asn Ser Cys Leu
    370                 375                 380

Asn Pro Val Leu Tyr Cys Leu Val Arg Arg Glu Phe Arg Lys Ala Leu
385                 390                 395                 400

Lys Ser Leu Leu Trp Arg Ile Ala Ser Pro Ser Ile Thr Ser Met Arg
            405                 410                 415

Pro Phe Thr Ala Thr Thr Lys Pro Glu His Glu Asp Gln Gly Leu Gln
        420                 425                 430

Ala Pro Ala Pro Pro His Ala Ala Ala Glu Pro Asp Leu Leu Tyr Tyr
    435                 440                 445

Pro Pro Gly Val Val Val Tyr Ser Gly Gly Arg Tyr Asp Leu Leu Pro
450                 455                 460

Ser Ser Ser Ala Tyr
465

<210> SEQ ID NO 26
<211> LENGTH: 414
<212> TYPE: PRT
<213> ORGANISM: Mouse

<400> SEQUENCE: 26

Met Ala Thr Ser Asn Ser Ser Ala Ser Leu Pro Thr Leu Phe Trp Val
1               5                   10                  15

Asn Gly Ser Gly Asp Ser Val Leu Ser Thr Asp Gly Ala Ala Met Pro
            20                  25                  30

Val Gln Phe Leu Val Leu Arg Ile Met Val Ala Leu Ala Tyr Gly Leu
        35                  40                  45

Val Gly Ile Ile Gly Leu Leu Gly Asn Leu Ala Val Leu Trp Val Leu
```

```
            50                  55                  60
Gly Asn Cys Gly Gln Arg Val Pro Gly Leu Ser Ser Asp Thr Phe Val
 65                  70                  75                  80

Phe Ser Leu Ala Leu Ala Asp Leu Gly Leu Ala Leu Thr Leu Pro Phe
                 85                  90                  95

Trp Ala Thr Glu Ser Ala Met Asp Phe His Trp Pro Phe Gly Ser Ala
            100                 105                 110

Leu Cys Lys Val Val Leu Thr Thr Val Leu Ser Ile Tyr Ala Ser
            115                 120                 125

Thr Phe Leu Ile Thr Ala Leu Ser Ile Ala Arg Tyr Trp Val Ala
            130                 135                 140

Met Ala Val Gly Pro Gly Ser His Leu Ser Val Phe Trp Ala Arg Val
145                 150                 155                 160

Val Thr Leu Ala Val Trp Val Ala Ala Leu Val Thr Val Pro Thr
                165                 170                 175

Ala Ile Phe Gly Ala Glu Val Glu Leu Trp Gly Val Cys Leu Cys Leu
                180                 185                 190

Leu Arg Phe Pro Ser Arg Tyr Trp Leu Gly Ala Tyr Gln Leu Gln Arg
                195                 200                 205

Val Val Leu Ala Phe Ile Val Pro Leu Gly Val Ile Thr Thr Ser Tyr
                210                 215                 220

Leu Leu Leu Leu Ala Phe Leu Glu Arg Gln Gln Arg Cys Arg Pro Arg
225                 230                 235                 240

Gln Trp Gln Asp Ser Arg Val Val Ala Arg Ser Val Arg Val Leu Val
                245                 250                 255

Ala Ser Phe Ala Leu Cys Trp Val Pro Asn His Val Val Thr Leu Trp
                260                 265                 270

Glu Ile Leu Val Arg Phe Asp Leu Val Pro Trp Asp Ser Thr Phe Tyr
                275                 280                 285

Thr Phe His Thr Tyr Ile Leu Pro Ile Thr Thr Cys Leu Ala His Ser
                290                 295                 300

Asn Ser Cys Leu Asn Pro Val Ile Tyr Cys Leu Leu Arg Arg Glu Pro
305                 310                 315                 320

Gln Gln Val Leu Val Ser Ser Phe Arg Ala Leu Trp Ser Arg Leu Trp
                325                 330                 335

Pro Gln Arg Lys Ala Cys Met Glu Gln Met Ala Leu Lys Glu Val Gly
                340                 345                 350

Gly Arg Thr Val Ala Ser Thr Gln Glu Ser Gly Ser Arg Thr His
                355                 360                 365

Thr Asn Thr Met Glu His Leu Asp Gly Cys Ser Leu Asn Thr Leu
            370                 375                 380

Leu Ser Glu Thr Tyr Gln Gly Gln Ser Pro Gln Ile Leu Gly Arg Ser
385                 390                 395                 400

Ser Cys Ser Leu Ser Gln Ala Ala Val Ser Pro Gly Glu Val
                405                 410

<210> SEQ ID NO 27
<211> LENGTH: 374
<212> TYPE: PRT
<213> ORGANISM: Homo sapiens

<400> SEQUENCE: 27

Met Pro Thr Leu Asn Thr Ser Ala Ser Pro Pro Thr Phe Phe Trp Ala
 1                   5                  10                  15
```

```
Asn Ala Ser Gly Gly Ser Val Leu Ser Ala Asp Asp Ala Pro Met Pro
                20                  25                  30

Val Lys Phe Leu Ala Leu Arg Leu Met Val Ala Leu Ala Tyr Gly Leu
            35                  40                  45

Val Gly Ala Ile Gly Leu Leu Gly Asn Leu Ala Val Leu Trp Val Leu
        50                  55                  60

Ser Asn Cys Ala Arg Arg Ala Pro Gly Pro Ser Asp Thr Phe Val
65                  70                  75                  80

Phe Asn Leu Ala Leu Ala Asp Leu Gly Leu Ala Leu Thr Leu Pro Phe
                85                  90                  95

Trp Ala Ala Glu Ser Ala Leu Asp Phe His Trp Pro Phe Gly Gly Ala
            100                 105                 110

Leu Cys Lys Met Val Leu Thr Ala Thr Val Leu Asn Val Tyr Ala Ser
        115                 120                 125

Ile Phe Leu Ile Thr Ala Leu Ser Val Ala Arg Tyr Trp Val Val Ala
    130                 135                 140

Met Ala Ala Gly Pro Gly Thr His Leu Ser Leu Phe Trp Ala Arg Ile
145                 150                 155                 160

Ala Thr Leu Ala Val Trp Ala Ala Ala Leu Val Thr Val Pro Thr
                165                 170                 175

Ala Val Phe Gly Val Glu Gly Glu Val Cys Gly Val Arg Leu Cys Leu
            180                 185                 190

Leu Arg Phe Pro Ser Arg Tyr Trp Leu Gly Ala Tyr Gln Leu Gln Arg
        195                 200                 205

Val Val Leu Ala Phe Met Val Pro Leu Gly Val Ile Thr Thr Ser Tyr
    210                 215                 220

Leu Leu Leu Leu Ala Phe Leu Gln Arg Arg Gln Arg Arg Arg Gln Asp
225                 230                 235                 240

Ser Arg Val Val Ala Arg Ser Val Arg Ile Leu Val Ala Ser Phe Phe
                245                 250                 255

Leu Cys Trp Phe Pro Asn His Val Val Thr Leu Trp Gly Val Leu Val
            260                 265                 270

Lys Phe Asp Leu Val Pro Trp Asn Ser Thr Phe Tyr Thr Ile Gln Thr
        275                 280                 285

Tyr Val Phe Pro Val Thr Thr Cys Leu Ala His Ser Asn Ser Cys Leu
    290                 295                 300

Asn Pro Val Leu Tyr Cys Leu Leu Arg Arg Glu Pro Arg Gln Ala Leu
305                 310                 315                 320

Ala Gly Thr Phe Arg Asp Leu Arg Ser Arg Leu Trp Pro Gln Gly Gly
                325                 330                 335

Gly Trp Val Gln Gln Val Ala Leu Lys Gln Val Gly Arg Trp Val
            340                 345                 350

Ala Ser Asn Pro Arg Glu Ser Arg Pro Ser Thr Leu Leu Thr Asn Leu
        355                 360                 365

Asp Arg Gly Thr Pro Gly
    370

<210> SEQ ID NO 28
<211> LENGTH: 51
<212> TYPE: PRT
<213> ORGANISM: Human

<400> SEQUENCE: 28

Arg Ala Ala Pro Tyr Gly Val Arg Leu Cys Gly Arg Glu Phe Ile Arg
1               5                   10                  15
```

```
Ala Val Ile Phe Thr Cys Gly Gly Ser Arg Trp Asp Val Leu Ala Gly
            20                  25                  30

Leu Ser Ser Ser Cys Cys Lys Trp Gly Cys Ser Lys Ser Glu Ile Ser
            35                  40                  45

Ser Leu Cys
        50

<210> SEQ ID NO 29
<211> LENGTH: 373
<212> TYPE: PRT
<213> ORGANISM: Monkey

<400> SEQUENCE: 29

Met Pro Thr Leu Asn Thr Ser Ala Ser Pro Pro Thr Phe Trp Ala Asn
1               5                   10                  15

Ala Ser Gly Gly Ser Val Leu Ser Ala Asp Asp Ala Pro Met Pro Val
            20                  25                  30

Lys Phe Leu Ala Leu Arg Leu Met Val Ala Leu Ala Tyr Gly Leu Val
            35                  40                  45

Gly Ala Val Gly Leu Leu Gly Asn Leu Ala Val Leu Trp Val Leu Ser
        50                  55                  60

Asn Cys Ala Arg Arg Ala Pro Gly Pro Pro Ser Asp Thr Phe Val Phe
65                  70                  75                  80

Asn Leu Ala Leu Ala Asp Leu Gly Leu Ala Leu Thr Leu Pro Phe Trp
                85                  90                  95

Ala Ala Glu Ser Ala Leu Asp Phe His Trp Pro Phe Gly Gly Ala Leu
            100                 105                 110

Cys Lys Met Val Leu Thr Ala Thr Val Leu Asn Val Tyr Ala Ser Ile
            115                 120                 125

Phe Leu Ile Thr Ala Leu Ser Val Ala Arg Tyr Trp Val Val Ala Met
        130                 135                 140

Ala Ala Gly Pro Gly Thr His Leu Ser Leu Phe Trp Ala Arg Ile Ala
145                 150                 155                 160

Thr Leu Ala Val Trp Ala Ala Ala Ala Leu Val Thr Val Pro Thr Ala
                165                 170                 175

Val Phe Gly Val Glu Gly Glu Val Cys Gly Val Arg Leu Cys Leu Leu
            180                 185                 190

Arg Phe Pro Ser Arg Tyr Trp Leu Gly Ala Tyr Gln Leu Gln Arg Val
            195                 200                 205

Val Leu Ala Phe Met Val Pro Leu Gly Val Ile Thr Thr Ser Tyr Leu
        210                 215                 220

Leu Leu Leu Ala Phe Leu Gln Gln Arg Gln Arg Arg Gln Gln Asp Ser
225                 230                 235                 240

Arg Val Val Ala Arg Ser Val Arg Ile Leu Val Ala Ser Phe Phe Leu
                245                 250                 255

Cys Trp Phe Pro Asn His Val Val Thr Leu Trp Gly Val Leu Val Lys
            260                 265                 270

Phe Asp Leu Val Pro Trp Asn Ser Thr Phe Tyr Thr Ile Gln Thr Tyr
            275                 280                 285

Val Leu Pro Val Thr Thr Cys Leu Ala His Ser Asn Ser Cys Leu Asn
        290                 295                 300

Pro Val Leu Tyr Cys Leu Leu Arg Arg Glu Pro Arg Gln Ala Leu Ala
305                 310                 315                 320

Asp Thr Phe Arg Asp Leu Arg Ser Arg Leu Trp Pro Gln Gly Gly Gly
```

```
                    325                 330                 335
Trp Val Gln Val Ala Leu Lys Gln Val Gly Arg Arg Trp Val Ala
            340                 345                 350
Ser Asn Pro Pro Glu Ser Arg Pro Ser Thr Leu Leu Thr Asn Leu Asp
        355                 360                 365
Gly Gly Thr Pro Gly
    370

<210> SEQ ID NO 30
<211> LENGTH: 373
<212> TYPE: PRT
<213> ORGANISM: Cow

<400> SEQUENCE: 30

Met Pro Thr Pro Asn Thr Ser Ala Pro Leu Pro Ala Phe Trp Val Asn
1               5                   10                  15

Ala Ser Gly Gly Ser Val Leu Ser Ala Ala Asp Ala Thr Met Pro Val
            20                  25                  30

Gly Phe Leu Ala Leu Arg Val Ser Val Ala Leu Ala Tyr Gly Leu Val
        35                  40                  45

Gly Ala Val Gly Leu Leu Gly Asn Ser Ala Val Leu Trp Val Leu Gly
    50                  55                  60

Asn Cys Ala Gln Arg Ala Pro Cys Pro Pro Ser Asp Thr Phe Val Phe
65                  70                  75                  80

Asn Leu Ala Leu Ala Asp Leu Gly Leu Ala Leu Thr Leu Pro Phe Trp
                85                  90                  95

Ala Ala Glu Ser Ala Leu Asp Phe His Trp Pro Phe Gly Gly Ala Leu
            100                 105                 110

Cys Lys Met Val Leu Thr Ala Thr Val Leu Asn Ile Tyr Ala Ser Ile
        115                 120                 125

Phe Leu Ile Thr Ala Leu Ser Val Ala Arg Tyr Trp Val Val Ala Met
    130                 135                 140

Ala Ala Gly Pro Gly Thr His Leu Ser Leu Phe Trp Ala Arg Val Ala
145                 150                 155                 160

Thr Leu Ala Met Trp Val Ala Ala Ser Leu Val Thr Val Pro Thr Ala
                165                 170                 175

Val Phe Gly Ala Glu Gly Glu Val Ser Gly Val Arg Leu Cys Leu Leu
            180                 185                 190

Arg Phe Pro Ser Arg Tyr Trp Leu Gly Ala Tyr Gln Leu Gln Arg Val
        195                 200                 205

Val Leu Ala Phe Met Val Pro Leu Ser Ile Ile Thr Thr Ser Tyr Leu
    210                 215                 220

Leu Leu Leu Ala Phe Leu Arg Arg Arg Arg Arg Trp Arg Asp Ser
225                 230                 235                 240

Arg Gly Val Ala His Ser Ile Arg Ile Leu Leu Ala Ser Phe Phe Leu
                245                 250                 255

Cys Trp Phe Pro Asn His Val Val Thr Leu Trp Gly Val Leu Val Lys
            260                 265                 270

Phe Asp Leu Val Pro Trp Asp Ser Thr Phe Tyr Thr Val His Thr Tyr
        275                 280                 285

Val Phe Pro Val Thr Thr Cys Leu Ala His Thr Asn Ser Cys Leu Asn
    290                 295                 300

Pro Val Leu Tyr Cys Leu Leu Arg Gln Glu Pro Arg Gln Ala Leu Ala
305                 310                 315                 320
```

-continued

```
Asp Thr Phe Arg Asp Leu Arg Ala Arg Leu Trp Pro Gln Gly Arg Gly
            325                 330                 335

Trp Val Glu Gln Val Ala Leu Lys Glu Met Gly Arg Arg Trp Thr Glu
        340                 345                 350

Ser Thr Pro Gln Glu Gly Gly Leu Ser Thr Met Leu Thr Asn Leu Asp
    355                 360                 365

Lys Gly Asn Pro Gly
        370

<210> SEQ ID NO 31
<211> LENGTH: 373
<212> TYPE: PRT
<213> ORGANISM: Pig

<400> SEQUENCE: 31

Met Pro Thr Pro Asn Thr Ser Ala Pro Leu Pro Ala Phe Trp Val Asn
1               5                   10                  15

Ala Ser Gly Gly Ser Val Leu Ser Ala Asp Asp Ala Thr Met Pro Val
            20                  25                  30

Gly Phe Leu Ala Leu Arg Val Met Val Ala Leu Ala Tyr Gly Leu Val
        35                  40                  45

Gly Ala Val Gly Leu Leu Gly Asn Leu Ala Val Leu Trp Val Leu Gly
    50                  55                  60

Asn Cys Ala Arg Arg Ala Pro Cys Pro Pro Ser Asp Thr Phe Val Phe
65                  70                  75                  80

Asn Leu Ala Leu Ala Asp Leu Gly Leu Ala Leu Thr Leu Pro Phe Trp
                85                  90                  95

Ala Ala Glu Ser Ala Leu Asp Phe His Trp Pro Phe Gly Gly Ala Leu
            100                 105                 110

Cys Lys Met Ile Leu Thr Ala Thr Val Leu Asn Ile Tyr Ala Ser Ile
        115                 120                 125

Phe Leu Ile Thr Ala Leu Ser Val Ala Arg Tyr Trp Val Val Ala Met
    130                 135                 140

Ala Gly Gly Pro Gly Thr His Leu Ser Leu Phe Trp Ala Arg Val Ala
145                 150                 155                 160

Thr Leu Ala Val Trp Val Ala Ala Leu Val Thr Val Pro Thr Ala
                165                 170                 175

Val Phe Gly Ala Glu Gly Glu Leu Cys Gly Val Arg Leu Cys Leu Leu
            180                 185                 190

Arg Phe Pro Ser Arg Tyr Trp Leu Gly Ala Tyr Gln Leu Gln Arg Val
        195                 200                 205

Val Leu Ala Phe Met Val Pro Leu Gly Ile Ile Thr Thr Ser Tyr Leu
    210                 215                 220

Leu Leu Leu Ala Phe Leu Arg Arg Arg Gln Arg Arg Gln Asp Asn
225                 230                 235                 240

Arg Val Val Ala Arg Ser Ile Arg Ile Leu Leu Ala Ser Phe Phe Leu
                245                 250                 255

Cys Trp Phe Pro Asn His Val Val Thr Phe Trp Gly Val Leu Val Lys
            260                 265                 270

Phe Asp Leu Val Pro Trp Asp Ser Thr Phe Tyr Thr Ile His Thr Tyr
        275                 280                 285

Val Phe Pro Val Thr Thr Cys Leu Ala His Ser Asn Ser Cys Leu Asn
    290                 295                 300

Pro Val Leu Tyr Cys Leu Leu Arg Glu Pro Arg Arg Ala Leu Glu
305                 310                 315                 320
```

```
Val Thr Phe Arg Asp Leu Arg Ala Arg Leu Trp Pro Gln Gly Arg Gly
            325                 330                 335

Trp Val Glu Gln Val Ala Leu Lys Glu Val Gly Arg Arg Trp Glu Glu
            340                 345                 350

Ile Thr Pro Arg Asp Gly Gly Pro Ser Ala Met Pro Thr Asn Arg Asp
            355                 360                 365

Lys Gly Thr Ala Gly
        370

<210> SEQ ID NO 32
<211> LENGTH: 34
<212> TYPE: DNA
<213> ORGANISM: Artificial
<220> FEATURE:
<223> OTHER INFORMATION: Human Relaxin-3 5' forward PCR primer

<400> SEQUENCE: 32
actagactgc aggccgccat gctgaccgca gcgt                               34

<210> SEQ ID NO 33
<211> LENGTH: 111
<212> TYPE: DNA
<213> ORGANISM: Artificial
<220> FEATURE:
<223> OTHER INFORMATION: Human Relaxin-1 3' reverse PCR primer

<400> SEQUENCE: 33
actagaggat cctcagcaat atttagcaag agacctttg gtacaaccaa ttaggcaaca    60
tttctcaaac agtgccacgt agggtcgtcg tcggccccga agaacccag g             111

<210> SEQ ID NO 34
<211> LENGTH: 111
<212> TYPE: DNA
<213> ORGANISM: Artificial
<220> FEATURE:
<223> OTHER INFORMATION: Human Relaxin-2 3' reverse PCR primer

<400> SEQUENCE: 34
actagaggat cctcagcaaa atctagcaag agatcttttg gtacaaccaa catggcaaca   60
tttattagcc aatgcactgt agagttgtcg tcggccccga agaacccag g             111

<210> SEQ ID NO 35
<211> LENGTH: 98
<212> TYPE: DNA
<213> ORGANISM: Artificial
<220> FEATURE:
<223> OTHER INFORMATION: Human INSL3 3' reverse primer

<400> SEQUENCE: 35
acgataggat cctcagcaca gggtcagcag gtcctgctgg gtgcagccgg acaggcagca   60
gtagcgggcg gggtttcgtc ggccccgaag aaccccag                          98

<210> SEQ ID NO 36
<211> LENGTH: 96
<212> TYPE: DNA
<213> ORGANISM: Artificial
<220> FEATURE:
<223> OTHER INFORMATION: Human INSL4 3' reverse primer

<400> SEQUENCE: 36
atgacaggat cctcagcaca gcttcacgga ggtgccgtcg tcgcagatca cctcgcagca   60
```

```
gaaggggtcg aatcgtcggc cccgaagaac cccagg                                      96

<210> SEQ ID NO 37
<211> LENGTH: 108
<212> TYPE: DNA
<213> ORGANISM: Artificial
<220> FEATURE:
<223> OTHER INFORMATION: Human INSL5 3' reverse primer

<400> SEQUENCE: 37
atagaaggat ccttagcaaa gagcactcaa atcagtcatg aacagccat cagtgcaaca          60 caaagtttgt aaatcttgtc gtcggccccg aagaacccca ggggttcc                      108

<210> SEQ ID NO 38
<211> LENGTH: 98
<212> TYPE: DNA
<213> ORGANISM: Artificial
<220> FEATURE:
<223> OTHER INFORMATION: Human INSL6 3' reverse PCR primer

<400> SEQUENCE: 38
atgacaggat cctcagcagg cgatggacag ctcctccttg gtgcagccgg tcaggcagca          60
cttctcggag tagcctcgtc ggccccgaag aaccccag                                 98

<210> SEQ ID NO 39
<211> LENGTH: 98
<212> TYPE: DNA
<213> ORGANISM: Artificial
<220> FEATURE:
<223> OTHER INFORMATION: Human Insulin 3' reverse PCR primer

<400> SEQUENCE: 39
acgataggat cctcagcagt agttctccag ctggtacagg gagcagatgg aggtgcagca          60
ctgctccacg atgcctcgtc ggccccgaag aaccccag                                 98

<210> SEQ ID NO 40
<211> LENGTH: 98
<212> TYPE: DNA
<213> ORGANISM: Artificial
<220> FEATURE:
<223> OTHER INFORMATION: Artificial A chain 3' reverse PCR primer

<400> SEQUENCE: 40
acgataggat cctcagcagg ccttctcgat ctcgtagtcg tcgcagatgg acaggcagca          60
gttctcgtac aggcctcgtc ggccccgaag aaccccag                                 98

<210> SEQ ID NO 41
<211> LENGTH: 45
<212> TYPE: DNA
<213> ORGANISM: Artificial
<220> FEATURE:
<223> OTHER INFORMATION: Human LGR7 5' forward PCR primer

<400> SEQUENCE: 41
agatgagaat tcgccaccat gacatctggt tctgtcttct tctac                         45

<210> SEQ ID NO 42
<211> LENGTH: 41
<212> TYPE: DNA
<213> ORGANISM: Artificial
<220> FEATURE:
<223> OTHER INFORMATION: Human LGR7 3' reverse PCR primer

<400> SEQUENCE: 42
```
tagagagcgg ccgctcatga ataggaattg agtctcgttg a                                41

<210> SEQ ID NO 43
<211> LENGTH: 48
<212> TYPE: DNA
<213> ORGANISM: Artificial
<220> FEATURE:
<223> OTHER INFORMATION: Human LGR8 5' forward PCR primer

<400> SEQUENCE: 43
tagacagaat tcgccaccat gattgttttt ctggttttta aacatctc                         48

<210> SEQ ID NO 44
<211> LENGTH: 41
<212> TYPE: DNA
<213> ORGANISM: Artificial
<220> FEATURE:
<223> OTHER INFORMATION: Human LGR8 3' reverse primer

<400> SEQUENCE: 44
atgatagcgg ccgcctagga aactggtttc attatactgt c                                41

<210> SEQ ID NO 45
<211> LENGTH: 472
<212> TYPE: PRT
<213> ORGANISM: Mouse

<400> SEQUENCE: 45

```
Met Gln Val Ala Ser Ala Thr Pro Ala Ala Thr Val Arg Lys Ala Ala
1               5                   10                  15

Ala Gly Asp Glu Leu Ser Glu Phe Phe Ala Leu Thr Pro Asp Leu Leu
            20                  25                  30

Glu Val Ala Asn Ala Ser Gly Asn Ala Ser Leu Gln Leu Gln Asp Leu
        35                  40                  45

Trp Trp Glu Leu Gly Leu Glu Leu Pro Asp Gly Ala Pro Gly His
    50                  55                  60

Pro Pro Gly Gly Gly Gly Ala Glu Ser Thr Asp Thr Glu Ala Arg Val
65                  70                  75                  80

Arg Ile Leu Ile Ser Ala Val Tyr Trp Val Cys Ala Leu Gly Leu
            85                  90                  95

Ala Gly Asn Leu Leu Val Leu Tyr Leu Met Lys Ser Lys Gln Gly Trp
            100                 105                 110

Arg Lys Ser Ser Ile Asn Leu Phe Val Thr Asn Leu Ala Leu Thr Asp
        115                 120                 125

Phe Gln Phe Val Leu Thr Leu Pro Phe Trp Ala Val Glu Asn Ala Leu
    130                 135                 140

Asp Phe Lys Trp Pro Phe Gly Lys Ala Met Cys Lys Ile Val Ser Met
145                 150                 155                 160

Val Thr Ser Met Asn Met Tyr Ala Ser Val Phe Phe Leu Thr Ala Met
            165                 170                 175

Ser Val Ala Arg Tyr His Ser Val Ala Ser Ala Leu Lys Ser His Arg
        180                 185                 190

Thr Arg Gly Arg Gly Arg Gly Asp Cys Cys Gly Gln Ser Leu Arg Glu
    195                 200                 205

Ser Cys Cys Phe Ser Ala Lys Val Leu Cys Gly Leu Ile Trp Ala Ser
    210                 215                 220

Ala Ala Leu Ala Ser Leu Pro Asn Ala Ile Phe Ser Thr Thr Ile Arg
225                 230                 235                 240
```

-continued

```
Val Leu Gly Glu Glu Leu Cys Leu Met His Phe Pro Asp Lys Leu Leu
                245                 250                 255
Gly Trp Asp Arg Gln Phe Trp Leu Gly Leu Tyr His Leu Gln Lys Val
            260                 265                 270
Leu Leu Gly Phe Leu Leu Pro Leu Ser Ile Ile Ser Leu Cys Tyr Leu
        275                 280                 285
Leu Leu Val Arg Phe Ile Ser Asp Arg Arg Val Val Gly Thr Thr Asp
    290                 295                 300
Ala Val Gly Ala Ala Ala Pro Gly Gly Leu Ser Thr Ala Ser
305                 310                 315                 320
Ala Arg Arg Arg Ser Lys Val Thr Lys Ser Val Thr Ile Val Val Leu
                325                 330                 335
Ser Phe Phe Leu Cys Trp Leu Pro Asn Gln Ala Leu Thr Thr Trp Ser
            340                 345                 350
Ile Leu Ile Lys Phe Asn Ala Val Pro Phe Ser Gln Glu Tyr Phe Gln
        355                 360                 365
Cys Gln Val Tyr Ala Phe Pro Val Ser Val Cys Leu Ala His Ser Asn
    370                 375                 380
Ser Cys Leu Asn Pro Ile Leu Tyr Cys Leu Val Arg Arg Glu Phe Arg
385                 390                 395                 400
Lys Ala Leu Lys Asn Leu Leu Trp Arg Ile Ala Ser Pro Ser Leu Thr
                405                 410                 415
Asn Met Arg Pro Phe Thr Ala Thr Thr Lys Pro Glu Pro Glu Asp His
            420                 425                 430
Gly Leu Gln Ala Leu Ala Pro Leu Asn Ala Ala Ala Glu Pro Asp Leu
        435                 440                 445
Ile Tyr Tyr Pro Pro Gly Val Val Tyr Ser Gly Gly Arg Tyr Asp
    450                 455                 460
Leu Leu Pro Ser Ser Ser Ala Tyr
465                 470

<210> SEQ ID NO 46
<211> LENGTH: 476
<212> TYPE: PRT
<213> ORGANISM: Rat

<400> SEQUENCE: 46

Met Pro Lys Ala His Leu Ser Met Gln Val Ala Ser Ala Thr Thr Ala
1               5                   10                  15
Ala Pro Met Ser Lys Ala Ala Gly Asp Glu Leu Ser Gly Phe Phe
            20                  25                  30
Gly Leu Ile Pro Asp Leu Leu Glu Val Ala Asn Arg Ser Ser Asn Ala
        35                  40                  45
Ser Leu Gln Leu Gln Asp Leu Trp Trp Glu Leu Gly Leu Glu Leu Pro
    50                  55                  60
Asp Gly Ala Ala Pro Gly His Pro Pro Gly Ser Gly Gly Ala Glu Ser
65                  70                  75                  80
Ala Asp Thr Glu Ala Arg Val Arg Ile Leu Ile Ser Ala Val Tyr Trp
                85                  90                  95
Val Val Cys Ala Leu Gly Leu Ala Gly Asn Leu Leu Val Leu Tyr Leu
            100                 105                 110
Met Lys Ser Lys Gln Gly Trp Arg Lys Ser Ser Ile Asn Leu Phe Val
        115                 120                 125
Thr Asn Leu Ala Leu Thr Asp Phe Gln Phe Val Leu Thr Leu Pro Phe
```

```
                130                 135                 140
Trp Ala Val Glu Asn Ala Leu Asp Phe Lys Trp Pro Phe Gly Lys Ala
145                 150                 155                 160

Met Cys Lys Ile Val Ser Met Val Thr Ser Met Asn Met Tyr Ala Ser
                165                 170                 175

Val Phe Phe Leu Thr Ala Met Ser Val Ala Arg Tyr His Ser Val Ala
                180                 185                 190

Ser Ala Leu Lys Ser His Arg Thr Arg Gly His Gly Arg Gly Asp Cys
                195                 200                 205

Cys Gly Gln Ser Leu Gly Glu Ser Cys Cys Phe Ser Ala Lys Val Leu
210                 215                 220

Cys Gly Leu Ile Trp Ala Ser Ala Ile Ala Ser Leu Pro Asn Val
225                 230                 235                 240

Ile Phe Ser Thr Thr Ile Asn Val Leu Gly Glu Leu Cys Leu Met
                245                 250                 255

His Phe Pro Asp Lys Leu Leu Gly Trp Asp Arg Gln Phe Trp Leu Gly
                260                 265                 270

Leu Tyr His Leu Gln Lys Val Leu Leu Gly Phe Leu Leu Pro Leu Ser
                275                 280                 285

Ile Ile Ser Leu Cys Tyr Leu Leu Leu Val Arg Phe Ile Ser Asp Arg
290                 295                 300

Arg Val Val Gly Thr Thr Asp Gly Ala Thr Ala Pro Gly Gly Ser Leu
305                 310                 315                 320

Ser Thr Ala Gly Ala Arg Arg Arg Ser Lys Val Thr Lys Ser Val Thr
                325                 330                 335

Ile Val Val Leu Ser Phe Phe Leu Cys Trp Leu Pro Asn Gln Ala Leu
                340                 345                 350

Thr Thr Trp Ser Ile Leu Ile Lys Phe Asn Val Val Pro Phe Ser Gln
                355                 360                 365

Glu Tyr Phe Gln Cys Gln Val Tyr Ala Phe Pro Val Ser Val Cys Leu
                370                 375                 380

Ala His Ser Asn Ser Cys Leu Asn Pro Ile Leu Tyr Cys Leu Val Arg
385                 390                 395                 400

Arg Glu Phe Arg Lys Ala Leu Lys Asn Leu Leu Trp Arg Ile Ala Ser
                405                 410                 415

Pro Ser Leu Thr Ser Met Arg Pro Phe Thr Ala Thr Lys Pro Glu
                420                 425                 430

Pro Glu Asp His Gly Leu Gln Ala Leu Ala Pro Leu Asn Ala Thr Ala
                435                 440                 445

Glu Pro Asp Leu Ile Tyr Tyr Pro Pro Gly Val Val Val Tyr Ser Gly
450                 455                 460

Gly Arg Tyr Asp Leu Leu Pro Ser Ser Ser Ala Tyr
465                 470                 475

<210> SEQ ID NO 47
<211> LENGTH: 469
<212> TYPE: PRT
<213> ORGANISM: Rat

<400> SEQUENCE: 47

Met Gln Val Ala Ser Ala Thr Thr Ala Ala Pro Met Ser Lys Ala Ala
1               5                   10                  15

Ala Gly Asp Glu Leu Ser Gly Phe Phe Gly Leu Ile Pro Asp Leu Leu
                20                  25                  30
```

-continued

```
Glu Val Ala Asn Arg Ser Ser Asn Ala Ser Leu Gln Leu Gln Asp Leu
             35                  40                  45

Trp Trp Glu Leu Gly Leu Glu Leu Pro Asp Gly Ala Ala Pro Gly His
 50                  55                  60

Pro Pro Gly Ser Gly Gly Ala Glu Ser Ala Asp Thr Glu Ala Arg Val
 65                  70                  75                  80

Arg Ile Leu Ile Ser Ala Val Tyr Trp Val Cys Ala Leu Gly Leu
                 85                  90                  95

Ala Gly Asn Leu Leu Val Leu Tyr Leu Met Lys Ser Lys Gln Gly Trp
            100                 105                 110

Arg Lys Ser Ser Ile Asn Leu Phe Val Thr Asn Leu Ala Leu Thr Asp
            115                 120                 125

Phe Gln Phe Val Leu Thr Leu Pro Phe Trp Ala Val Glu Asn Ala Leu
130                 135                 140

Asp Phe Lys Trp Pro Phe Gly Lys Ala Met Cys Lys Ile Val Ser Met
145                 150                 155                 160

Val Thr Ser Met Asn Met Tyr Ala Ser Val Phe Phe Leu Thr Ala Met
                165                 170                 175

Ser Val Ala Arg Tyr His Ser Val Ala Ser Ala Leu Lys Ser His Arg
            180                 185                 190

Thr Arg Gly His Gly Arg Gly Asp Cys Cys Gly Gln Ser Leu Gly Glu
            195                 200                 205

Ser Cys Cys Phe Ser Ala Lys Val Leu Cys Gly Leu Ile Trp Ala Ser
    210                 215                 220

Ala Ala Ile Ala Ser Leu Pro Asn Val Ile Phe Ser Thr Thr Ile Asn
225                 230                 235                 240

Val Leu Gly Glu Glu Leu Cys Leu Met His Phe Pro Asp Lys Leu Leu
                245                 250                 255

Gly Trp Asp Arg Gln Phe Trp Leu Gly Leu Tyr His Leu Gln Lys Val
            260                 265                 270

Leu Leu Gly Phe Leu Leu Pro Leu Ser Ile Ile Ser Leu Cys Tyr Leu
            275                 280                 285

Leu Leu Val Arg Phe Ile Ser Asp Arg Arg Val Val Gly Thr Thr Asp
290                 295                 300

Gly Ala Thr Ala Pro Gly Gly Ser Leu Ser Thr Ala Gly Ala Arg Arg
305                 310                 315                 320

Arg Ser Lys Val Thr Lys Ser Val Thr Ile Val Val Leu Ser Phe Phe
                325                 330                 335

Leu Cys Trp Leu Pro Asn Gln Ala Leu Thr Thr Trp Ser Ile Leu Ile
            340                 345                 350

Lys Phe Asn Val Val Pro Phe Ser Gln Glu Tyr Phe Gln Cys Gln Val
            355                 360                 365

Tyr Ala Phe Pro Val Ser Val Cys Leu Ala His Ser Asn Ser Cys Leu
370                 375                 380

Asn Pro Ile Leu Tyr Cys Leu Val Arg Arg Glu Phe Arg Lys Ala Leu
385                 390                 395                 400

Lys Asn Leu Leu Trp Arg Ile Ala Ser Pro Ser Leu Thr Ser Met Arg
                405                 410                 415

Pro Phe Thr Ala Thr Thr Lys Pro Glu Pro Glu Asp His Gly Leu Gln
            420                 425                 430

Ala Leu Ala Pro Leu Asn Ala Thr Ala Glu Pro Asp Leu Ile Tyr Tyr
            435                 440                 445

Pro Pro Gly Val Val Tyr Ser Gly Gly Arg Tyr Asp Leu Leu Pro
```

Ser Ser Ser Ala Tyr
465

<210> SEQ ID NO 48
<211> LENGTH: 426
<212> TYPE: DNA
<213> ORGANISM: Mouse

<400> SEQUENCE: 48

| | | | | | |
|---|---|---|---|---|---|
| atggcaatgc | tcgggctgct | gctgctggct | tcctgggctc | tcctcggggc | tctggggctg | 60 |
| caggccgagg | cgaggccggc | gccctacggg | gtgaagctct | gcggtcggga | gttcatccgc | 120 |
| gcggtcatct | tcacttgcgg | aggctcacga | tggcgccggg | cggacatctt | ggcccacgaa | 180 |
| tctctggggg | acttcttcgc | tgatggagaa | gccaatacag | accacctggc | cagcgagctg | 240 |
| gatgaagcgg | tgggctccag | cgagtggctg | gccctaacca | aatcccccca | ggctttctac | 300 |
| ggtggtcgag | ccagctggca | agggtcacct | ggagtggttc | ggggcagcag | agatgtgttg | 360 |
| gctggccttt | ccagcagttg | ctgcgagtgg | ggctgtagca | agagccaaat | tagcagcttg | 420 |
| tgctag | | | | | | 426 |

<210> SEQ ID NO 49
<211> LENGTH: 141
<212> TYPE: PRT
<213> ORGANISM: Mouse

<400> SEQUENCE: 49

Met Ala Met Leu Gly Leu Leu Leu Ala Ser Trp Ala Leu Leu
1               5                   10                  15
Ala Leu Gly Leu Gln Ala Glu Ala Arg Pro Ala Pro Tyr Gly Val Lys
                20                  25                  30
Leu Cys Gly Arg Glu Phe Ile Arg Ala Val Ile Phe Thr Cys Gly Gly
            35                  40                  45
Ser Arg Trp Arg Arg Ala Asp Ile Leu Ala His Glu Ser Leu Gly Asp
        50                  55                  60
Phe Phe Ala Asp Gly Glu Ala Asn Thr Asp His Leu Ala Ser Glu Leu
65                  70                  75                  80
Asp Glu Ala Val Gly Ser Ser Glu Trp Leu Ala Leu Thr Lys Ser Pro
                85                  90                  95
Gln Ala Phe Tyr Gly Gly Arg Ala Ser Trp Gln Gly Ser Pro Gly Val
                100                 105                 110
Val Arg Gly Ser Arg Asp Val Leu Ala Gly Leu Ser Ser Ser Cys Cys
            115                 120                 125
Glu Trp Gly Cys Ser Lys Ser Gln Ile Ser Ser Leu Cys
        130                 135                 140

<210> SEQ ID NO 50
<211> LENGTH: 423
<212> TYPE: DNA
<213> ORGANISM: Rat

<400> SEQUENCE: 50

| | | | | | |
|---|---|---|---|---|---|
| atggcaactc | gggggctgct | gctggcttcc | tgggctctcc | tcggggctct | ggtgctgcag | 60 |
| gccgaggcga | ggcccgcgcc | ctatggggtg | aagctctgcg | gtcgggagtt | catccgcgcg | 120 |
| gtcatcttca | cctgcggggg | ctcacgatgg | cgcgggcgg | acatcttggc | ccacgaccct | 180 |
| ctgggggaat | tcttcgctga | tggagaagcc | aatacagacc | acctggccag | cgaactggac | 240 |

```
gaagctgtgg gctccagcga gtggctggcc ctgaccaaat ccccccaggt cttctatggg    300
ggtcgatcca gctggcaagg gtctcccgga gtggttcggg gcagcagaga tgtgctggct    360
ggcctttcca gcagctgttg cgagtggggc tgtagtaaga gccaaattag cagcttgtgc    420
tag                                                                  423
```

```
<210> SEQ ID NO 51
<211> LENGTH: 140
<212> TYPE: PRT
<213> ORGANISM: Rat

<400> SEQUENCE: 51
```

| Met | Ala | Thr | Arg | Gly | Leu | Leu | Leu | Ala | Ser | Trp | Ala | Leu | Leu | Gly | Ala |
|---|---|---|---|---|---|---|---|---|---|---|---|---|---|---|---|
| 1 | | | | 5 | | | | | 10 | | | | | 15 | |

| Leu | Val | Leu | Gln | Ala | Glu | Ala | Arg | Pro | Ala | Pro | Tyr | Gly | Val | Lys | Leu |
|---|---|---|---|---|---|---|---|---|---|---|---|---|---|---|---|
| | | | 20 | | | | | 25 | | | | | 30 | | |

| Cys | Gly | Arg | Glu | Phe | Ile | Arg | Ala | Val | Ile | Phe | Thr | Cys | Gly | Gly | Ser |
|---|---|---|---|---|---|---|---|---|---|---|---|---|---|---|---|
| | | | 35 | | | | | 40 | | | | | 45 | | |

| Arg | Trp | Arg | Arg | Ala | Asp | Ile | Leu | Ala | His | Asp | Pro | Leu | Gly | Glu | Phe |
|---|---|---|---|---|---|---|---|---|---|---|---|---|---|---|---|
| | 50 | | | | | 55 | | | | | 60 | | | | |

| Phe | Ala | Asp | Gly | Glu | Ala | Asn | Thr | Asp | His | Leu | Ala | Ser | Glu | Leu | Asp |
|---|---|---|---|---|---|---|---|---|---|---|---|---|---|---|---|
| 65 | | | | | 70 | | | | | 75 | | | | | 80 |

| Glu | Ala | Val | Gly | Ser | Ser | Glu | Trp | Leu | Ala | Leu | Thr | Lys | Ser | Pro | Gln |
|---|---|---|---|---|---|---|---|---|---|---|---|---|---|---|---|
| | | | | 85 | | | | | 90 | | | | | 95 | |

| Val | Phe | Tyr | Gly | Gly | Arg | Ser | Ser | Trp | Gln | Gly | Ser | Pro | Gly | Val | Val |
|---|---|---|---|---|---|---|---|---|---|---|---|---|---|---|---|
| | | | 100 | | | | | 105 | | | | | 110 | | |

| Arg | Gly | Ser | Arg | Asp | Val | Leu | Ala | Gly | Leu | Ser | Ser | Cys | Cys | Glu |
|---|---|---|---|---|---|---|---|---|---|---|---|---|---|---|
| | | | 115 | | | | | 120 | | | | | 125 | |

| Trp | Gly | Cys | Ser | Lys | Ser | Gln | Ile | Ser | Ser | Leu | Cys |
|---|---|---|---|---|---|---|---|---|---|---|---|
| | 130 | | | | | 135 | | | | | 140 |

```
<210> SEQ ID NO 52
<211> LENGTH: 558
<212> TYPE: DNA
<213> ORGANISM: Human

<400> SEQUENCE: 52
atgcctcgcc tgttcttgtt ccacctgcta gaattctgtt tactactgaa ccaattttcc     60
agagcagtcg cggccaaatg gaaggacgat gttattaaat tatgcggccg cgaattagtt    120
cgcgcgcaga ttgccatttg cggcatgagc acctggagca aaaggtctct gagccaggaa    180
gatgctcctc agacacctag accagtggca gaaattgtac catccttcat caacaaagat    240
acagaaacta taattatcat gttggaattc attgctaatt tgccaccgga gctgaaggca    300
gccctatctg agaggcaacc atcattacca gagctacagc agtatgtacc tgcattaaag    360
gattccaatc ttagctttga agaatttaag aaacttattc gcaataggca agtgaagcc    420 gcagacagca tccttcaga attaaaatac ttaggcttgg atactcattc tcaaaaaaag    480
agacgaccct acgtggcact gtttgagaaa tgttgcctaa ttggttgtac caaaggtct    540 cttgctaaat attgctga                                                  558
```

```
<210> SEQ ID NO 53
<211> LENGTH: 185
<212> TYPE: PRT
<213> ORGANISM: Human

<400> SEQUENCE: 53
```

```
Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
                180                 185

<210> SEQ ID NO 54
<211> LENGTH: 558
<212> TYPE: DNA
<213> ORGANISM: Human

<400> SEQUENCE: 54
atgcctcgcc tgttttttt ccacctgcta ggagtctgtt tactactgaa ccaattttcc      60
agagcagtcg cggactcatg gatggaggaa gttattaaat tatgcggccg cgaattagtt     120
cgcgcgcaga ttgccatttg cggcatgagc acctggagca aaggtctct gagccaggaa      180 gatgctcctc agacacctag accagtggca gaaattgtgc catccttcat caacaaagat     240
acagaaacca taaatatgat gtcagaattt gttgctaatt tgccacagga gctgaagtta     300
accctgtctg agatgcagcc agcattacca cagctacaac aacatgtacc tgtattaaaa     360
gattccagtc ttctctttga agaatttaag aaacttattc gcaatagaca aagtgaagcc     420
gcagacagca gtccttcaga attaaaatac ttaggcttgg atactcattc tcgaaaaaag     480
agacaactct acagtgcatt ggctaataaa tgttgccatg ttggttgtac caaaagatct     540
cttgctagat tttgctga                                                   558

<210> SEQ ID NO 55
<211> LENGTH: 185
<212> TYPE: PRT
<213> ORGANISM: Human

<400> SEQUENCE: 55

Met Pro Arg Leu Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30
```

Lys Leu Cys Gly Arg Glu Leu Val Arg Ala Gln Ile Ala Ile Cys Gly
         35                  40                  45

Met Ser Thr Trp Ser Lys Arg Ser Leu Ser Gln Glu Asp Ala Pro Gln
 50                  55                  60

Thr Pro Arg Pro Val Ala Glu Ile Val Pro Ser Phe Ile Asn Lys Asp
 65                  70                  75                  80

Thr Glu Thr Ile Asn Met Met Ser Glu Phe Val Ala Asn Leu Pro Gln
                 85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185

<210> SEQ ID NO 56
<211> LENGTH: 549
<212> TYPE: DNA
<213> ORGANISM: Pig

<400> SEQUENCE: 56
atgccgcgcc tgttctccta cctcctaggt gtctggctgc tcctgagcca acttcccaga      60
gaaatcccag gccagagtac gaacgatttt attaaggcat gcggccgaga attagtccgt     120
ctgtgggtgg agatctgtgg ctccgtctcc tggggaagaa ctgctctcag cctggaagag     180
cctcagctgg aaactggacc cccggcagaa accatgccat cctccatcac caaagatgca     240
gaaatcttaa agatgatgtt ggaatttgtt cctaatttgc cacaggagct gaaggcaaca     300
ttgtctgaga ggcaaccatc actgagagag ctacaacaat ctgcatcaaa ggattcgaat     360
cttaactttg aagaatttaa gaaaattatt cttaacagac aaaatgaagc agaagacaaa     420
agtcttttag aattaaaaaa cttaggttta gataaacatt ccagaaaaaa gagactgttc     480
cgtatgacac tgagcgagaa atgttgtcaa gtaggttgta tcagaaaaga tattgctaga     540
ttatgctga                                                            549

<210> SEQ ID NO 57
<211> LENGTH: 182
<212> TYPE: PRT
<213> ORGANISM: Pig

<400> SEQUENCE: 57

Met Pro Arg Leu Phe Ser Tyr Leu Leu Gly Val Trp Leu Leu Leu Ser
 1               5                  10                  15

Gln Leu Pro Arg Glu Ile Pro Gly Gln Ser Thr Asn Asp Phe Ile Lys
            20                  25                  30

Ala Cys Gly Arg Glu Leu Val Arg Leu Trp Val Glu Ile Cys Gly Ser
        35                  40                  45

Val Ser Trp Gly Arg Thr Ala Leu Ser Leu Glu Glu Pro Gln Leu Glu
    50                  55                  60

Thr Gly Pro Pro Ala Glu Thr Met Pro Ser Ser Ile Thr Lys Asp Ala

```
              65                  70                  75                  80
Glu Ile Leu Lys Met Met Leu Glu Phe Val Pro Asn Leu Pro Gln Glu
                    85                  90                  95

Leu Lys Ala Thr Leu Ser Glu Arg Gln Pro Ser Leu Arg Glu Leu Gln
                100                 105                 110

Gln Ser Ala Ser Lys Asp Ser Asn Leu Asn Phe Glu Glu Phe Lys Lys
                115                 120                 125

Ile Ile Leu Asn Arg Gln Asn Glu Ala Glu Asp Lys Ser Leu Leu Glu
        130                 135                 140

Leu Lys Asn Leu Gly Leu Asp Lys His Ser Arg Lys Lys Arg Leu Phe
145                 150                 155                 160

Arg Met Thr Leu Ser Glu Lys Cys Cys Gln Val Gly Cys Ile Arg Lys
                165                 170                 175

Asp Ile Ala Arg Leu Cys
                180

<210> SEQ ID NO 58
<211> LENGTH: 558
<212> TYPE: DNA
<213> ORGANISM: Mouse

<400> SEQUENCE: 58
atgtccagca gattttttgct ccagctcctg gggttctggc tattgctgag ccagccttgc      60
aggacgcgag tctcggagga gtggatggac ggattcattc ggatgtgcgg ccgtgaatat     120
gcccgtgaat tgatcaaaat ctgcggggcc tccgtgggaa gattggcttt gagccaggag     180
gagccagctc tgcttgccag gcaagccact gaagttgtgc catccttcat caacaaagat     240
gcagagcctt tcgatacgac gctgaaatgc cttccaaatt tgtctgaaga gctcaaggca     300
gtactgtctg aggctcaggc ctcgctccca gagctacaac acgcacctgt gttgagcgat     360
tctgttgtta gcttggaagg ctttaagaaa actctccatg ataaactggg tgaagcagaa     420
gacggcagtc ctccagggct aaatacttg caatcagata cccattcacg gaaaaagagg      480
gagtctggtg gattgatgag ccagcaatgt tgccacgtcg ttgtagcag aagatctatt      540 gctaaactct attgctga                                                   558

<210> SEQ ID NO 59
<211> LENGTH: 185
<212> TYPE: PRT
<213> ORGANISM: Mouse

<400> SEQUENCE: 59

Met Ser Ser Arg Phe Leu Leu Gln Leu Leu Gly Phe Trp Leu Leu Leu
1               5                   10                  15

Ser Gln Pro Cys Arg Thr Arg Val Ser Glu Glu Trp Met Asp Gly Phe
                20                  25                  30

Ile Arg Met Cys Gly Arg Glu Tyr Ala Arg Glu Leu Ile Lys Ile Cys
            35                  40                  45

Gly Ala Ser Val Gly Arg Leu Ala Leu Ser Gln Glu Glu Pro Ala Leu
        50                  55                  60

Leu Ala Arg Gln Ala Thr Glu Val Val Pro Ser Phe Ile Asn Lys Asp
65                  70                  75                  80

Ala Glu Pro Phe Asp Thr Thr Leu Lys Cys Leu Pro Asn Leu Ser Glu
                85                  90                  95

Glu Leu Lys Ala Val Leu Ser Glu Ala Gln Ala Ser Leu Pro Glu Leu
                100                 105                 110
```

Gln His Ala Pro Val Leu Ser Asp Ser Val Val Ser Leu Glu Gly Phe
                115                 120                 125

Lys Lys Thr Leu His Asp Lys Leu Gly Glu Ala Glu Asp Gly Ser Pro
            130                 135                 140

Pro Gly Leu Lys Tyr Leu Gln Ser Asp Thr His Ser Arg Lys Lys Arg
145                 150                 155                 160

Glu Ser Gly Gly Leu Met Ser Gln Gln Cys Cys His Val Gly Cys Ser
                165                 170                 175

Arg Arg Ser Ile Ala Lys Leu Tyr Cys
            180                 185

<210> SEQ ID NO 60
<211> LENGTH: 561
<212> TYPE: DNA
<213> ORGANISM: Rat

<400> SEQUENCE: 60
atgtccagca gactcttgct ccagctcctg gggttctggc tgttcctgag ccagccttgc      60
agggcgcgag tctcggagga gtggatggac caagtcattc aggtgtgcgg ccgtggatat     120
gcccgcgcat ggatcgaagt ctgcggggcc tccgtgggaa gactggcttt gagccaggag     180
gagccagctc cgctagccag gcaagccact gcagaagttg tgccatcctt catcaacaaa     240
gatgcggagc ctttcgatat gacgttgaaa tgccttccaa atttgtctga ggagcggaag     300
gcagcactgt ctgaggggcg agcaccgttc ccagagctac aacaacacgc accgcgttg      360 agcgattccg ttgttagctt ggaaggattt aagaaaactt tccacaatca gctgggtgaa     420
gcagaagatg gcggtcctcc agagctcaaa tacttaggct cagatgctca gtcacggaaa     480
aagaggcagt ctggcgcact gctcagtgag cagtgttgcc acatcggttg taccagaaga     540
tccattgcta aactctgctg a                                              561

<210> SEQ ID NO 61
<211> LENGTH: 186
<212> TYPE: PRT
<213> ORGANISM: Rat

<400> SEQUENCE: 61

Met Ser Ser Arg Leu Leu Leu Gln Leu Leu Gly Phe Trp Leu Phe Leu
1               5                   10                  15

Ser Gln Pro Cys Arg Ala Arg Val Ser Glu Glu Trp Met Asp Gln Val
            20                  25                  30

Ile Gln Val Cys Gly Arg Gly Tyr Ala Arg Ala Trp Ile Glu Val Cys
        35                  40                  45

Gly Ala Ser Val Gly Arg Leu Ala Leu Ser Gln Glu Glu Pro Ala Pro
    50                  55                  60

Leu Ala Arg Gln Ala Thr Ala Glu Val Val Pro Ser Phe Ile Asn Lys
65                  70                  75                  80

Asp Ala Glu Pro Phe Asp Met Thr Leu Lys Cys Leu Pro Asn Leu Ser
                85                  90                  95

Glu Glu Arg Lys Ala Ala Leu Ser Glu Gly Arg Ala Pro Phe Pro Glu
            100                 105                 110

Leu Gln Gln His Ala Pro Ala Leu Ser Asp Ser Val Val Ser Leu Glu
        115                 120                 125

Gly Phe Lys Lys Thr Phe His Asn Gln Leu Gly Glu Ala Glu Asp Gly
    130                 135                 140

Gly Pro Pro Glu Leu Lys Tyr Leu Gly Ser Asp Ala Gln Ser Arg Lys
145                 150                 155                 160

Lys Arg Gln Ser Gly Ala Leu Leu Ser Glu Gln Cys Cys His Ile Gly
            165                 170                 175

Cys Thr Arg Arg Ser Ile Ala Lys Leu Cys
            180                 185

<210> SEQ ID NO 62
<211> LENGTH: 396
<212> TYPE: DNA
<213> ORGANISM: Human

<400> SEQUENCE: 62 atggacccccc gtctgcccgc ctgggcactg gtgctgctgg ccctgccct ggtgttcgcg      60 ttgggccccg cgcccacccc agagatgcgt gagaagttgt gcggccacca cttcgtacgc    120
gcgctagtgc gcgtgtgcgg gggccccgc tggtccaccg aagccaggag gcctgcggcc      180
ggaggcgacc gtgagttgct acagtggctg agagacgac atctgctcca tgggctggtg     240
gccgacagta atctcacgct gggacctggc ctgcagcccc tgccccagac ctctcaccat    300
caccgccacc accgtgcagc tgccaccaac cctgcacgct actgctgcct cagtggctgt    360
acccaacaag acctgctgac cctctgtccc tactga                              396

<210> SEQ ID NO 63
<211> LENGTH: 131
<212> TYPE: PRT
<213> ORGANISM: Human

<400> SEQUENCE: 63

Met Asp Pro Arg Leu Pro Ala Trp Ala Leu Val Leu Leu Gly Pro Ala
1               5                   10                  15

Leu Val Phe Ala Leu Gly Pro Ala Pro Thr Pro Glu Met Arg Glu Lys
            20                  25                  30

Leu Cys Gly His His Phe Val Arg Ala Leu Val Arg Val Cys Gly Gly
        35                  40                  45

Pro Arg Trp Ser Thr Glu Ala Arg Arg Pro Ala Ala Gly Gly Asp Arg
    50                  55                  60

Glu Leu Leu Gln Trp Leu Glu Arg Arg His Leu Leu His Gly Leu Val
65                  70                  75                  80

Ala Asp Ser Asn Leu Thr Leu Gly Pro Gly Leu Gln Pro Leu Pro Gln
                85                  90                  95

Thr Ser His His His Arg His His Arg Ala Ala Ala Thr Asn Pro Ala
            100                 105                 110

Arg Tyr Cys Cys Leu Ser Gly Cys Thr Gln Gln Asp Leu Leu Thr Leu
        115                 120                 125

Cys Pro Tyr
    130

<210> SEQ ID NO 64
<211> LENGTH: 369
<212> TYPE: DNA
<213> ORGANISM: Mouse

<400> SEQUENCE: 64
atgcgcgcgc cgctgctact gatgctcctg gctctggggt ccgcgctgcg ctccccgcag      60
ccccccgagg cacgcgccaa gctctgcggc caccacctgg tgcgcacgct ggtgcgggtg    120
tgcggcggcc cacgctggtc gcccgaggcc acgcagcctg tggagacccg ggaccgggag    180

```
ctgctgcagt ggctagagca gagacatctc ctgcacgcgc tggtggccga cgtggaccca      240
gcgctagacc cgcagcttcc tcggcaggct tctcagcgcc agcgccgcag tgccgccacc      300
aacgctgtgc accgctgctg tcttactggc tgcacccagc aagacctgtt gggtctgtgt      360
ccccactga                                                              369

<210> SEQ ID NO 65
<211> LENGTH: 122
<212> TYPE: PRT
<213> ORGANISM: Mouse

<400> SEQUENCE: 65

Met Arg Ala Pro Leu Leu Leu Met Leu Leu Ala Leu Gly Ser Ala Leu
1               5                   10                  15

Arg Ser Pro Gln Pro Pro Glu Ala Arg Ala Lys Leu Cys Gly His His
                20                  25                  30

Leu Val Arg Thr Leu Val Arg Val Cys Gly Gly Pro Arg Trp Ser Pro
            35                  40                  45

Glu Ala Thr Gln Pro Val Glu Thr Arg Asp Arg Glu Leu Leu Gln Trp
        50                  55                  60

Leu Glu Gln Arg His Leu Leu His Ala Leu Val Ala Asp Val Asp Pro
65                  70                  75                  80

Ala Leu Asp Pro Gln Leu Pro Arg Gln Ala Ser Gln Arg Gln Arg Arg
                85                  90                  95

Ser Ala Ala Thr Asn Ala Val His Arg Cys Cys Leu Thr Gly Cys Thr
                100                 105                 110

Gln Gln Asp Leu Leu Gly Leu Cys Pro His
        115                 120

<210> SEQ ID NO 66
<211> LENGTH: 387
<212> TYPE: DNA
<213> ORGANISM: Rat

<400> SEQUENCE: 66
atgcacgcac tgctgctact gctgctcctg gctctagggt ccgcgctgcg ctccccgcag      60
cccccggagg cgcgcgccaa gctctgtggt caccacctgg tgcgtgcgct ggtgcgggtg      120
tgcggtggcc cgcgttggtc acccgaggcc acgcagcctg tggacacccg cgaccgggag      180
ctgctgcagt ggctggagca cgacatctc ctgcacgcgc tcgtggccga tgcggatccc      240
gcgctagacc cggaccccgc gctggacccg cagcttcctc accaggcttc tcagcgccag      300
cgccgcagtg tggccaccaa cgctgtgcac cgctgctgtc tcactggctg cacccagcaa      360
gacctttggg gtctgtgtcc ccactga                                          387

<210> SEQ ID NO 67
<211> LENGTH: 128
<212> TYPE: PRT
<213> ORGANISM: Rat

<400> SEQUENCE: 67

Met His Ala Leu Leu Leu Leu Leu Leu Ala Leu Gly Ser Ala Leu
1               5                   10                  15

Arg Ser Pro Gln Pro Pro Glu Ala Arg Ala Lys Leu Cys Gly His His
                20                  25                  30

Leu Val Arg Ala Leu Val Arg Val Cys Gly Gly Pro Arg Trp Ser Pro
            35                  40                  45
```

```
Glu Ala Thr Gln Pro Val Asp Thr Arg Asp Arg Glu Leu Leu Gln Trp
        50                  55                  60

Leu Glu Gln Arg His Leu Leu His Ala Leu Val Ala Asp Ala Asp Pro
65                  70                  75                  80

Ala Leu Asp Pro Asp Pro Ala Leu Asp Pro Gln Leu Pro His Gln Ala
                85                  90                  95

Ser Gln Arg Gln Arg Arg Ser Val Ala Thr Asn Ala Val His Arg Cys
            100                 105                 110

Cys Leu Thr Gly Cys Thr Gln Gln Asp Leu Leu Gly Leu Cys Pro His
            115                 120                 125

<210> SEQ ID NO 68
<211> LENGTH: 420
<212> TYPE: DNA
<213> ORGANISM: Human

<400> SEQUENCE: 68
atggccagcc tgttccggtc ctatctgcca gcaatctggc tgctgctgag ccaactcctt      60
agagaaagcc tagcagcaga gctgagggga tgtggtcccc gatttggaaa acacttgctg    120
tcatattgcc ccatgcctga agacattc accaccaccc aggagggtg gctgctggaa       180 tctggacgtc ccaagaaat ggtgtcaacc tccaacaaca agatggaca agccttaggt      240 acgacatcag aattcattcc taatttgtca ccagagctga agaaaccact gtctgaaggg    300
cagccatcat tgaagaaaat aatactttcc cgcaaaaaga gaagtggacg tcacagattt    360
gatccattct gttgtgaagt aatttgtgac gatggaactt cagttaaatt atgtacatag    420

<210> SEQ ID NO 69
<211> LENGTH: 139
<212> TYPE: PRT
<213> ORGANISM: Human

<400> SEQUENCE: 69

Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
            20                  25                  30

Pro Arg Phe Gly Lys His Leu Leu Ser Tyr Cys Pro Met Pro Glu Lys
        35                  40                  45

Thr Phe Thr Thr Thr Pro Gly Gly Trp Leu Leu Glu Ser Gly Arg Pro
    50                  55                  60

Lys Glu Met Val Ser Thr Ser Asn Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
        115                 120                 125

Cys Asp Asp Gly Thr Ser Val Lys Leu Cys Thr
    130                 135

<210> SEQ ID NO 70
<211> LENGTH: 408
<212> TYPE: DNA
<213> ORGANISM: Human
```

-continued

<400> SEQUENCE: 70

```
atgaagggct ccattttcac tctgttttta ttctctgtcc tatttgccat ctcagaagtg      60
cggagcaagg agtctgtgag actctgtggg ctagaataca tacgacagt catctatatc      120 tgtgctagct ccaggtggag aaggcatctg gaggggatcc ctcaagctca gcaagctgag     180
acaggaaact ccttccagct cccacataaa cgtgagtttt ctgaggaaaa tccagcgcaa     240
aaccttccga aggtggatgc ctcaggggaa gaccgtcttt ggggtggaca gatgcccact     300
gaagagcttt ggaagtcaaa gaagcattca gtgatgtcaa gacaagattt acaaactttg     360
tgttgcactg atggctgttc catgactgat ttgagtgctc tttgctaa                  408
```

<210> SEQ ID NO 71
<211> LENGTH: 135
<212> TYPE: PRT
<213> ORGANISM: Human

<400> SEQUENCE: 71

```
Met Lys Gly Ser Ile Phe Thr Leu Phe Leu Phe Ser Val Leu Phe Ala
1               5                   10                  15

Ile Ser Glu Val Arg Ser Lys Glu Ser Val Arg Leu Cys Gly Leu Glu
            20                  25                  30

Tyr Ile Arg Thr Val Ile Tyr Ile Cys Ala Ser Ser Arg Trp Arg Arg
        35                  40                  45

His Leu Glu Gly Ile Pro Gln Ala Gln Gln Ala Glu Thr Gly Asn Ser
    50                  55                  60

Phe Gln Leu Pro His Lys Arg Glu Phe Ser Glu Glu Asn Pro Ala Gln
65                  70                  75                  80

Asn Leu Pro Lys Val Asp Ala Ser Gly Glu Asp Arg Leu Trp Gly Gly
                85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
        115                 120                 125

Thr Asp Leu Ser Ala Leu Cys
    130                 135
```

<210> SEQ ID NO 72
<211> LENGTH: 408
<212> TYPE: DNA
<213> ORGANISM: Mouse

<400> SEQUENCE: 72

```
atgaagggcc ccactcttgc tctgtttctc ctcttagttc tgttggctgt ggtggaagta     60
agaagcaggc agactgtgaa gctctgtggc ctggactacg tgagaacagt tatctacatc    120
tgtgccagct cacggtggag agacatctg gaggggcatt ccactctca acaagctgag      180 acaagaaact acctccagct cctagacagg cacgagccat ccaagaaaac tctggagcac    240
agccttccca agacggatct ctcaggacag gagcttgttc gagatccaca ggcacccaag    300
gaaggtcttt gggaactgaa gaagcactca gtggtatcca gacgagatct gcaagctctg    360
tgctgcaggg aaggctgctc catgaaggaa ctcagcaccc tctgttag                 408
```

<210> SEQ ID NO 73
<211> LENGTH: 135
<212> TYPE: PRT
<213> ORGANISM: Mouse

-continued

<400> SEQUENCE: 73

Met Lys Gly Pro Thr Leu Ala Leu Phe Leu Leu Val Leu Leu Ala
1               5                   10                  15

Val Val Glu Val Arg Ser Arg Gln Thr Val Lys Leu Cys Gly Leu Asp
            20                  25                  30

Tyr Val Arg Thr Val Ile Tyr Ile Cys Ala Ser Ser Arg Trp Arg Arg
                35                  40                  45

His Leu Glu Gly His Phe His Ser Gln Gln Ala Glu Thr Arg Asn Tyr
        50                  55                  60

Leu Gln Leu Leu Asp Arg His Glu Pro Ser Lys Lys Thr Leu Glu His
65                  70                  75                  80

Ser Leu Pro Lys Thr Asp Leu Ser Gly Gln Glu Leu Val Arg Asp Pro
                85                  90                  95

Gln Ala Pro Lys Glu Gly Leu Trp Glu Leu Lys Lys His Ser Val Val
            100                 105                 110

Ser Arg Arg Asp Leu Gln Ala Leu Cys Cys Arg Glu Gly Cys Ser Met
        115                 120                 125

Lys Glu Leu Ser Thr Leu Cys
    130                 135

<210> SEQ ID NO 74
<211> LENGTH: 642
<212> TYPE: DNA
<213> ORGANISM: Human

<400> SEQUENCE: 74
atgccgcggc tcctccgctt gtccctgctg tggcttggac tcctgctggt tcggttttct     60
cgtgaactga gcgacatcag cagtgccagg aagctgtgcg gcaggtactt ggtgaaagaa    120
atagaaaaac tctgcggcca tgccaactgg agccagttcc gtttcgagga ggaaaccccct   180
ttctcacggt tgattgcaca ggcctcggag aaggtcgaag cctacagccc ataccagttc    240
gaaagcccgc aaaccgcttc cccggcccgg ggaagaggca caaacccagt gtctacttct    300
tgggaagaag cagtaaacag ttgggaaatg cagtcactac tgagtataa ggataaaaag    360
ggatattcac cccttggtaa dacaagagaa ttttcttcat cacataatat caatgtatat    420
attcatgaga atgcattttt tcagaagaaa cgtagaaaca aaattaaaac cttaagcaat    480
ttgttttggg ggcatcatcc ccaaagaaaa cgcagaggat attcagaaaa gtgttgtctt    540
acaggatgta caaagaagaa acttagcatt gcatgtcttc catatattga ttttaaaagg    600
ctaaaggaaa aaagatcatc acttgtaact aagatatact aa                       642

<210> SEQ ID NO 75
<211> LENGTH: 213
<212> TYPE: PRT
<213> ORGANISM: Human

<400> SEQUENCE: 75

Met Pro Arg Leu Leu Arg Leu Ser Leu Leu Trp Leu Gly Leu Leu
1               5                   10                  15

Val Arg Phe Ser Arg Glu Leu Ser Asp Ile Ser Ser Ala Arg Lys Leu
            20                  25                  30

Cys Gly Arg Tyr Leu Val Lys Glu Ile Glu Lys Leu Cys Gly His Ala
        35                  40                  45

Asn Trp Ser Gln Phe Arg Phe Glu Glu Glu Thr Pro Phe Ser Arg Leu
    50                  55                  60

```
Ile Ala Gln Ala Ser Glu Lys Val Glu Ala Tyr Ser Pro Tyr Gln Phe
 65                  70                  75                  80

Glu Ser Pro Gln Thr Ala Ser Pro Ala Arg Gly Arg Gly Thr Asn Pro
                 85                  90                  95

Val Ser Thr Ser Trp Glu Glu Ala Val Asn Ser Trp Glu Met Gln Ser
            100                 105                 110

Leu Pro Glu Tyr Lys Asp Lys Lys Gly Tyr Ser Pro Leu Gly Lys Thr
        115                 120                 125

Arg Glu Phe Ser Ser Ser His Asn Ile Asn Val Tyr Ile His Glu Asn
    130                 135                 140

Ala Phe Phe Gln Lys Lys Arg Arg Asn Lys Ile Lys Thr Leu Ser Asn
145                 150                 155                 160

Leu Phe Trp Gly His His Pro Gln Arg Lys Arg Arg Gly Tyr Ser Glu
                165                 170                 175

Lys Cys Cys Leu Thr Gly Cys Thr Lys Glu Glu Leu Ser Ile Ala Cys
            180                 185                 190

Leu Pro Tyr Ile Asp Phe Lys Arg Leu Lys Glu Lys Arg Ser Ser Leu
        195                 200                 205

Val Thr Lys Ile Tyr
    210
```

<210> SEQ ID NO 76
<211> LENGTH: 576
<212> TYPE: DNA
<213> ORGANISM: Mouse

<400> SEQUENCE: 76

```
atgaagcagc tgtgctgttc ttgtctgttg tggcttggac tcctactgac tcctttctcc      60
agggaagagg aagaggaatc cagacccagg aagctgtgcg gcaggcacct gctgatagaa     120
gttataaaac tctgtggcca aagtgactgg agccggttcg agatggagga gcaaagtcct     180
atgacacagt tctttcccca ctactcacgc aagggcaaag ccttcaaccc tcacccttct     240
tcctccgcct ggagaagatt acaaacccca gtccctgcag cgtctctca gaagaagga      300
acacacactt gggagcctca gtcactgccc gactatcagt ttgaaaagac ggagttgctt     360
cctaaggcaa gagtgttttc ataccacagt ggcaagccct atgttaagag cgtacaactt     420
cagaagaaaa gcacgaacaa atgaatacc ttcagaagtt tattttgggg gaatcattcc      480
caaaggaaac gcagaggctt tgcagataag tgctgtgtga taggatgcac caaagaagag     540
atggccgtcg cgtgcctccc ctttgttgat ttttaa                              576
```

<210> SEQ ID NO 77
<211> LENGTH: 191
<212> TYPE: PRT
<213> ORGANISM: Mouse

<400> SEQUENCE: 77

```
Met Lys Gln Leu Cys Cys Ser Cys Leu Leu Trp Leu Gly Leu Leu Leu
1               5                   10                  15

Thr Pro Phe Ser Arg Glu Glu Glu Glu Ser Arg Pro Arg Lys Leu
            20                  25                  30

Cys Gly Arg His Leu Leu Ile Glu Val Ile Lys Leu Cys Gly Gln Ser
            35                  40                  45

Asp Trp Ser Arg Phe Glu Met Glu Glu Gln Ser Pro Met Thr Gln Phe
        50                  55                  60

Phe Pro His Tyr Ser Arg Lys Gly Lys Ala Phe Asn Pro His Pro Ser
```

```
                65                  70                  75                  80
Ser Ser Ala Trp Arg Arg Phe Thr Asn Pro Val Pro Ala Gly Val Ser
                    85                  90                  95

Gln Lys Lys Gly Thr His Thr Trp Glu Pro Gln Ser Leu Pro Asp Tyr
                100                 105                 110

Gln Phe Glu Lys Thr Glu Leu Leu Pro Lys Ala Arg Val Phe Ser Tyr
                115                 120                 125

His Ser Gly Lys Pro Tyr Val Lys Ser Val Gln Leu Gln Lys Lys Ser
            130                 135                 140

Thr Asn Lys Met Asn Thr Phe Arg Ser Leu Phe Trp Gly Asn His Ser
145                 150                 155                 160

Gln Arg Lys Arg Arg Gly Phe Ala Asp Lys Cys Cys Val Ile Gly Cys
                165                 170                 175

Thr Lys Glu Glu Met Ala Val Ala Cys Leu Pro Phe Val Asp Phe
                180                 185                 190
```

<210> SEQ ID NO 78
<211> LENGTH: 567
<212> TYPE: DNA
<213> ORGANISM: Rat

<400> SEQUENCE: 78

```
atgaagcagc tgtgctgttc ttgtctgttg tggcttggac tcctactggc tcctttctcc      60
caggaacaag aagaggtcac cagccccacg aagttgtgcg gcagggacct gttggtagaa     120
gttataaaac tctgtggcca aaatgactgg agccggttct cgatggaaga gcaaagtcct     180
atgacagagt tggttcccca atatacacgg aaagtcaaaa ccttcaaccc tcaccggtcc     240
tcctcctcct ggggaagatt cacaaaccca ggcgtctccc agaagaaagc aacacacact     300
tgggaatctc agtcactgcc caactatcag cttaaaaagg aggagctgct tcgaagaca      360
ggagtgcatt cataccacgg tggcaagccc tatgtgaaga gtgtaaaatt tcagaagaaa     420
aacactgaca aaatgagtac cttcagcggc ttattttggg ggaaccatcc ccagaggaag     480
cgcagaggtt cgcagataa atgctgtgct ataggggtgct ccaaagagga gctggccgtc     540
gcatgccttc cgtttgttga ttttttaa                                         567
```

<210> SEQ ID NO 79
<211> LENGTH: 188
<212> TYPE: PRT
<213> ORGANISM: Rat

<400> SEQUENCE: 79

```
Met Lys Gln Leu Cys Cys Ser Cys Leu Leu Trp Leu Gly Leu Leu
1               5                   10                  15

Ala Pro Phe Ser Gln Glu Gln Glu Val Thr Ser Pro Thr Lys Leu
                20                  25                  30

Cys Gly Arg Asp Leu Leu Val Glu Val Ile Lys Leu Cys Gly Gln Asn
                35                  40                  45

Asp Trp Ser Arg Phe Ser Met Glu Glu Gln Ser Pro Met Thr Glu Leu
            50                  55                  60

Val Pro Gln Tyr Thr Arg Lys Val Lys Thr Phe Asn Pro His Arg Ser
65                  70                  75                  80

Ser Ser Ser Trp Gly Arg Phe Thr Asn Pro Gly Val Ser Gln Lys Lys
                85                  90                  95

Ala Thr His Thr Trp Glu Ser Gln Ser Leu Pro Asn Tyr Gln Leu Lys
                100                 105                 110
```

```
Lys Glu Glu Leu Leu Pro Lys Thr Gly Val His Ser Tyr His Gly Gly
            115                 120                 125

Lys Pro Tyr Val Lys Ser Val Lys Phe Gln Lys Lys Asn Thr Asp Lys
            130                 135                 140

Met Ser Thr Phe Ser Gly Leu Phe Trp Gly Asn His Pro Gln Arg Lys
145                 150                 155                 160

Arg Arg Gly Phe Ala Asp Lys Cys Cys Ala Ile Gly Cys Ser Lys Glu
            165                 170                 175

Glu Leu Ala Val Ala Cys Leu Pro Phe Val Asp Phe
            180                 185

<210> SEQ ID NO 80
<211> LENGTH: 52
<212> TYPE: PRT
<213> ORGANISM: Human

<400> SEQUENCE: 80

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser Arg Pro Tyr Val
            20                  25                  30

Ala Leu Phe Glu Lys Cys Cys Leu Ile Gly Cys Thr Lys Arg Ser Leu
        35                  40                  45

Ala Lys Tyr Cys
    50

<210> SEQ ID NO 81
<211> LENGTH: 53
<212> TYPE: PRT
<213> ORGANISM: Human

<400> SEQUENCE: 81

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Gln Leu Tyr
            20                  25                  30

Ser Ala Leu Ala Asn Lys Cys Cys His Val Gly Cys Thr Lys Arg Ser
        35                  40                  45

Leu Ala Arg Phe Cys
    50

<210> SEQ ID NO 82
<211> LENGTH: 51
<212> TYPE: PRT
<213> ORGANISM: Human

<400> SEQUENCE: 82

Pro Thr Pro Glu Met Arg Glu Lys Leu Cys Gly His His Phe Val Arg
1               5                   10                  15

Ala Leu Val Arg Val Cys Gly Gly Pro Arg Trp Ser Thr Glu Ala Asn
            20                  25                  30

Pro Ala Arg Tyr Cys Cys Leu Ser Gly Cys Thr Gln Gln Asp Leu Leu
        35                  40                  45

Thr Leu Cys
    50

<210> SEQ ID NO 83
<211> LENGTH: 52
```

```
<212> TYPE: PRT
<213> ORGANISM: Human

<400> SEQUENCE: 83

Glu Ser Leu Ala Ala Glu Leu Arg Gly Cys Gly Pro Arg Phe Gly Lys
1               5                   10                  15

His Leu Leu Ser Tyr Cys Pro Met Pro Glu Lys Ser Gly Arg His Arg
            20                  25                  30

Phe Asp Pro Phe Cys Cys Glu Val Ile Cys Asp Asp Gly Thr Ser Val
        35                  40                  45

Lys Leu Cys Thr
    50

<210> SEQ ID NO 84
<211> LENGTH: 45
<212> TYPE: PRT
<213> ORGANISM: Human

<400> SEQUENCE: 84

Lys Glu Ser Val Arg Leu Cys Gly Leu Glu Tyr Ile Arg Thr Val Ile
1               5                   10                  15

Tyr Ile Cys Ala Ser Ser Arg Trp Gln Asp Leu Gln Thr Leu Cys Cys
            20                  25                  30

Thr Asp Gly Cys Ser Met Thr Asp Leu Ser Ala Leu Cys
        35                  40                  45

<210> SEQ ID NO 85
<211> LENGTH: 57
<212> TYPE: PRT
<213> ORGANISM: Human

<400> SEQUENCE: 85

Ile Ser Ser Ala Arg Lys Leu Cys Gly Arg Tyr Leu Val Lys Glu Ile
1               5                   10                  15

Glu Lys Leu Cys Gly His Ala Asn Trp Ser Gln Phe Gly Tyr Ser Glu
            20                  25                  30

Lys Cys Cys Leu Thr Gly Cys Thr Lys Glu Glu Leu Ser Ile Ala Cys
        35                  40                  45

Leu Pro Tyr Ile Asp Phe Lys Arg Leu
    50                  55

<210> SEQ ID NO 86
<211> LENGTH: 51
<212> TYPE: PRT
<213> ORGANISM: Human

<400> SEQUENCE: 86

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn
        35                  40                  45

Tyr Cys Asn
    50

<210> SEQ ID NO 87
<211> LENGTH: 70
<212> TYPE: PRT
<213> ORGANISM: Human
```

<400> SEQUENCE: 87

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 88
<211> LENGTH: 67
<212> TYPE: PRT
<213> ORGANISM: Human

<400> SEQUENCE: 88

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 89
<211> LENGTH: 27
<212> TYPE: PRT
<213> ORGANISM: Human

<400> SEQUENCE: 89

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
                20                  25

<210> SEQ ID NO 90
<211> LENGTH: 24
<212> TYPE: PRT
<213> ORGANISM: Human

<400> SEQUENCE: 90

Asp Val Leu Ala Gly Leu Ser Ser Ser Cys Cys Lys Trp Gly Cys Ser
1               5                   10                  15

Lys Ser Glu Ile Ser Ser Leu Cys
                20

<210> SEQ ID NO 91
<211> LENGTH: 24
<212> TYPE: PRT
<213> ORGANISM: Human

<400> SEQUENCE: 91

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 92
<211> LENGTH: 24
<212> TYPE: PRT
<213> ORGANISM: Human

<400> SEQUENCE: 92

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 93
<211> LENGTH: 22
<212> TYPE: PRT
<213> ORGANISM: Human

<400> SEQUENCE: 93

Ala Thr Asn Pro Ala Arg Tyr Cys Cys Leu Ser Gly Cys Thr Gln Gln
1               5                   10                  15

Asp Leu Leu Thr Leu Cys
            20

<210> SEQ ID NO 94
<211> LENGTH: 19
<212> TYPE: PRT
<213> ORGANISM: Human

<400> SEQUENCE: 94

Phe Asp Pro Phe Cys Cys Glu Val Ile Cys Asp Asp Gly Thr Ser Val
1               5                   10                  15

Lys Leu Cys

<210> SEQ ID NO 95
<211> LENGTH: 20
<212> TYPE: PRT
<213> ORGANISM: Human

<400> SEQUENCE: 95

Asp Leu Gln Thr Leu Cys Cys Thr Asp Gly Cys Ser Met Thr Asp Leu
1               5                   10                  15

Ser Ala Leu Cys
            20

<210> SEQ ID NO 96
<211> LENGTH: 20
<212> TYPE: PRT
<213> ORGANISM: Human

<400> SEQUENCE: 96

Gly Tyr Ser Glu Lys Cys Cys Leu Thr Gly Cys Thr Lys Glu Glu Leu
1               5                   10                  15

Ser Ile Ala Cys
            20

<210> SEQ ID NO 97
<211> LENGTH: 20
<212> TYPE: PRT
<213> ORGANISM: Human

```
<400> SEQUENCE: 97

Gly Ile Val Glu Gln Cys Cys Thr Ser Ile Cys Ser Leu Tyr Gln Leu
1               5                   10                  15

Glu Asn Tyr Cys
            20

<210> SEQ ID NO 98
<211> LENGTH: 20
<212> TYPE: PRT
<213> ORGANISM: Artificial Sequence
<220> FEATURE:
<223> OTHER INFORMATION: Random alpha chain sequence containing
      conserved methionine residues

<400> SEQUENCE: 98

Gly Leu Tyr Glu Asn Cys Cys Leu Ser Ile Cys Asp Asp Tyr Glu Ile
1               5                   10                  15

Glu Lys Ala Cys
            20
```